(12) United States Patent
Zhang et al.

(10) Patent No.: US 10,583,306 B2
(45) Date of Patent: Mar. 10, 2020

(54) DETECTION OF ELECTROMAGNETIC INTERFERENCE IN A CARDIAC ELECTRICAL SIGNAL BY AN IMPLANTABLE MEDICAL DEVICE

(71) Applicant: Medtronic, Inc., Minneapolis, MN (US)

(72) Inventors: Xusheng Zhang, Shoreview, MN (US); Saul E. Greenhut, Aurora, CO (US); Michael W. Heinks, New Brighton, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 15/416,827

(22) Filed: Jan. 26, 2017

(65) Prior Publication Data

US 2018/0207437 A1 Jul. 26, 2018

(51) Int. Cl.
| | |
|---|---|
| *A61N 1/39* | (2006.01) |
| *A61N 1/362* | (2006.01) |
| *A61N 1/37* | (2006.01) |
| *A61N 1/365* | (2006.01) |
| *A61N 1/08* | (2006.01) |

(52) U.S. Cl.
CPC ............ *A61N 1/3962* (2013.01); *A61N 1/08* (2013.01); *A61N 1/3621* (2013.01); *A61N 1/36507* (2013.01); *A61N 1/3718* (2013.01); *A61N 1/3925* (2013.01); *A61N 1/3987* (2013.01)

(58) Field of Classification Search
CPC .... A61N 1/3962; A61N 1/08; A61N 1/36507; A61N 1/3925; A61N 1/3718; A61N 1/3621
See application file for complete search history.

(56) References Cited

U.S. PATENT DOCUMENTS

| | | | |
|---|---|---|---|
| 5,188,117 A | 2/1993 | Steinhaus et al. | |
| 5,191,884 A * | 3/1993 | Gilli | A61N 1/3962 607/5 |
| 5,354,316 A | 10/1994 | Keimel | |

(Continued)

FOREIGN PATENT DOCUMENTS

EP  1932563 A1  6/2008

OTHER PUBLICATIONS (PCT/US2018/014648) PCT Notification of Transmittal of the International Search Report and the Written Opinion of the International Searching Authority, dated May 8, 2018, 12 pages.

(Continued)

*Primary Examiner* — Catherine M Voorhees
*Assistant Examiner* — Roland Dinga

(57) ABSTRACT

An implantable cardioverter defibrillator (ICD) starts a timer set to a time interval in response to a cardiac electrical signal crossing a noise threshold amplitude and resets the timer to the time interval in response to each crossing of the noise threshold amplitude by the cardiac electrical signal that occurs prior to the time interval expiring. A control circuit of the ICD determines a parameter of the behavior of the timer and identifies a sensed cardiac event as an electromagnetic interference (EMI) event based on the parameter. The ICD may detect EMI in response to the EMI event and withhold a tachyarrhythmia detection or therapy in response to EMI detection.

21 Claims, 20 Drawing Sheets

(56) References Cited

U.S. PATENT DOCUMENTS

| | | |
|---|---|---|
| 5,545,186 A | 8/1996 | Olson et al. |
| 5,647,379 A | 7/1997 | Meltzer |
| 5,766,227 A | 6/1998 | Nappholz et al. |
| 6,112,119 A | 8/2000 | Schuelke et al. |
| 6,393,316 B1 | 5/2002 | Gillberg et al. |
| 6,424,234 B1 | 7/2002 | Stevenson |
| 7,031,771 B2 | 4/2006 | Brown et al. |
| 7,403,813 B1 | 7/2008 | Farazzi et al. |
| 7,496,409 B2 | 2/2009 | Greenhut et al. |
| 7,567,835 B2 | 7/2009 | Gunderson et al. |
| 7,623,913 B2 | 11/2009 | Phillips |
| 7,715,906 B2 | 5/2010 | Krause et al. |
| 7,734,333 B2 | 6/2010 | Ghanem et al. |
| 7,734,336 B2 | 6/2010 | Ghanem et al. |
| 7,742,812 B2 | 6/2010 | Ghanem et al. |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,894,894 B2 | 2/2011 | Stadler et al. |
| 7,904,153 B2 | 3/2011 | Greenhut et al. |
| 7,907,993 B2 | 3/2011 | Ghanem et al. |
| 7,941,214 B2 | 5/2011 | Kleckner et al. |
| 7,991,471 B2 | 8/2011 | Ghanem et al. |
| 8,068,901 B2 | 11/2011 | Ghanem et al. |
| 8,150,514 B2 | 4/2012 | Mollerus |
| 8,160,684 B2 | 4/2012 | Ghanem et al. |
| 8,306,618 B2 | 11/2012 | Ghanem et al. |
| 8,435,185 B2 | 5/2013 | Ghanem et al. |
| 8,437,842 B2 | 5/2013 | Zhang et al. |
| 8,548,573 B2 | 10/2013 | Keefe |
| 8,694,097 B2 | 4/2014 | Cao et al. |
| 8,744,555 B2 | 6/2014 | Allavatam et al. |
| 8,744,556 B2 | 6/2014 | Mahajan et al. |
| 8,825,145 B1 | 9/2014 | Zhang |
| 8,868,170 B2 | 10/2014 | Bonan et al. |
| 8,983,586 B2 | 3/2015 | Zhang |
| 9,026,198 B2 | 5/2015 | Lian et al. |
| 9,174,062 B2 | 11/2015 | Stadler et al. |
| 2007/0156190 A1 | 7/2007 | Cinbis |
| 2007/0233198 A1 | 10/2007 | Ghanem et al. |
| 2007/0239046 A1 | 10/2007 | Ghanem et al. |
| 2008/0300497 A1 | 12/2008 | Krause et al. |
| 2010/0312131 A1 | 12/2010 | Naware et al. |
| 2011/0196247 A1 | 8/2011 | Cao et al. |
| 2015/0230723 A1 | 8/2015 | Stadler et al. |
| 2015/0272460 A1 | 10/2015 | Stadler et al. |
| 2015/0306375 A1 | 10/2015 | Marshall et al. |
| 2015/0306410 A1 | 10/2015 | Marshall et al. |
| 2016/0106989 A1* | 4/2016 | Stadler .................. A61N 1/368 607/4 |
| 2016/0158567 A1 | 6/2016 | Marshall et al. |

OTHER PUBLICATIONS

Zhang et al., "System and Method for Sensing and Detection in an Extra-Cardiovascular Implantable Cardioverter Defibrillator", U.S. Appl. No. 15/140,802, filed Apr. 28, 2016, 77 pages.

Greenhut et al., "Cardiac Electrical Signal Noise Detection for Tachyarrhythmia Episode Rejection", U.S. Appl. No. 62/367,170, filed Jul. 27, 2016, 94 pages.

Zhang et al., "Cardiac Electrical Signal Gross Morphology-Based Noise Detection for Rejection of Ventricular Tachyarrhythmia Detection", U.S. Appl. No. 62/367,166, filed Jul. 27, 2016, 93 pages.

Cao et al., "Cardiac Electrical Signal Morphology and Pattern-Based T-Wave Oversensing Rejection", U.S. Appl. No. 62/367,1221, filed Jul. 27, 2016, 92 pages.

Cao et al., "Multi-Threshold Sensing of Cardiac Electrical Signals in an Extracardiovascular Implantable Cardioverter Defibrillator", U.S. Appl. No. 15/142,171, filed Apr. 29, 2016, 71 pages.

* cited by examiner

DETECTION OF ELECTROMAGNETIC INTERFERENCE IN A CARDIAC ELECTRICAL SIGNAL BY AN IMPLANTABLE MEDICAL DEVICE

TECHNICAL FIELD

The disclosure relates generally to an implantable medical device system and method for detecting electromagnetic interference (EMI) in a cardiac electrical signal and withholding tachyarrhythmia therapy in response to detecting EMI.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events.

SUMMARY

In general, the disclosure is directed to techniques for detecting EMI in a cardiac electrical signal received by an implantable medical device, which may be an extra-cardiovascular ICD system. In some examples, an ICD system operating according to the techniques disclosed herein may operate a quiet timer and determine one or more parameters representing the timer behavior since a sensed cardiac event for identifying a next sensed cardiac event as an EMI event based on the timer behavior parameters. The ICD may withhold a tachyarrhythmia detection and therapy when EMI is detected. The ICD may determine an EMI index and generate an alert when EMI is detected.

In one example, the disclosure provides an ICD including a therapy delivery circuit, a sensing circuit and a control circuit coupled to the sensing circuit and the therapy delivery circuit. The therapy delivery circuit is configured to deliver a tachyarrhythmia therapy to a patient's heart via a pacing electrode vector coupleable to the therapy delivery circuit. The sensing circuit is configured to receive a cardiac electrical signal via a sensing electrode vector coupleable to the sensing circuit and to sense a cardiac event in response to a first crossing of a sensing threshold amplitude by the cardiac electrical signal and sense a second cardiac event in response to a second crossing of the sensing threshold amplitude by the cardiac electrical signal. The control circuit is configured to start a timer set to a time interval in response to the cardiac electrical signal crossing a noise threshold amplitude; reset the timer to the time interval in response to each crossing of the noise threshold amplitude by the cardiac electrical signal that occurs prior to the time interval expiring; and determine a parameter of a behavior of the timer. In response to the sensing circuit sensing the second cardiac event, the control circuit is configured to compare the parameter to EMI event criteria; identify the second cardiac event as an EMI event in response to the EMI event criteria being satisfied; update an EMI event count in response to identifying the second cardiac event as an EMI event; and compare a value of the updated EMI event count to EMI detection criteria. The control circuit is further configured to withhold the tachyarrhythmia therapy in response to the value of the updated EMI event count satisfying the EMI detection criteria.

In another example, the disclosure provides a method including sensing a first cardiac event by a sensing circuit in response to a first crossing of a sensing threshold amplitude by a cardiac electrical signal and sense a second cardiac event in response to a second crossing of the sensing threshold amplitude by the cardiac electrical signal; starting a timer set to a time interval in response to the cardiac electrical signal crossing a noise threshold amplitude; resetting the timer to the time interval in response to each crossing of the noise threshold amplitude by the cardiac electrical signal that occurs prior to the time interval expiring; determining by a control circuit of the ICD a parameter of a behavior of the timer; in response to sensing the second cardiac event, comparing the parameter to EMI event criteria; identifying the second cardiac event as an EMI event in response to the EMI event criteria being satisfied. The method may further include updating an EMI event count in response to identifying the second cardiac event as an EMI event; comparing a value of the updated EMI event count to EMI detection criteria; and withholding a tachyarrhythmia therapy in response to the value of the updated EMI event count satisfying the EMI detection criteria.

In another example, the disclosure provides a non-transitory, computer-readable storage medium comprising a set of instructions which, when executed by a control circuit of an ICD, cause the ICD to A non-transitory, computer-readable storage medium comprising a set of instructions which, when executed by a control circuit of an implantable cardioverter defibrillator (ICD), cause the ICD to sense a first cardiac event by a sensing circuit in response to a first crossing of a sensing threshold amplitude by a cardiac electrical signal and sense a second cardiac event in response to a second crossing of the sensing threshold amplitude by the cardiac electrical signal; start a timer set to a time interval in response to the cardiac electrical signal crossing a noise threshold amplitude; reset the timer to the time interval in response to each crossing of the noise threshold amplitude by the cardiac electrical signal that occurs prior to the time interval expiring; determine a parameter of a behavior of the timer; in response to sensing the second cardiac event, compare the parameter to electromagnetic interference (EMI) event criteria; identify the second cardiac event as an EMI event in response to the EMI event criteria being satisfied; update an EMI event count in response to identifying the second cardiac event as an EMI event; compare a value of the updated EMI event count to EMI detection criteria; and withhold a tachyarrhythmia therapy in response to the value of the updated EMI event count satisfying the EMI detection criteria.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting noise contamination of a cardiac electrical signal in cardiac medical device or system and withholding detection of a tachyarrhythmia in response to detecting noise. In one example, such a cardiac medical system may be an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide for detecting EMI in cardiac electrical signals acquired using extra-cardiovascular electrodes and withhold detection of tachyarrhythmia, e.g., ventricular tachycardia (VT) and ventricular fibrillation (VF), when EMI is detected.

The techniques are described in conjunction with an implantable medical lead carrying extra-cardiovascular electrodes, but aspects disclosed herein may be utilized in conjunction with other cardiac medical devices or systems. For example, the techniques for detecting EMI as described in conjunction with the accompanying drawings may be implemented in any implantable or external medical device enabled for sensing cardiac electrical signals, including implantable pacemakers, ICDs or cardiac monitors coupled to transvenous, pericardial or epicardial leads carrying sensing electrodes; leadless pacemakers, ICDs or cardiac monitors having housing-based sensing electrodes; and external or wearable pacemakers, defibrillators, or cardiac monitors coupled to external, surface or skin electrodes.

Figure 1A:
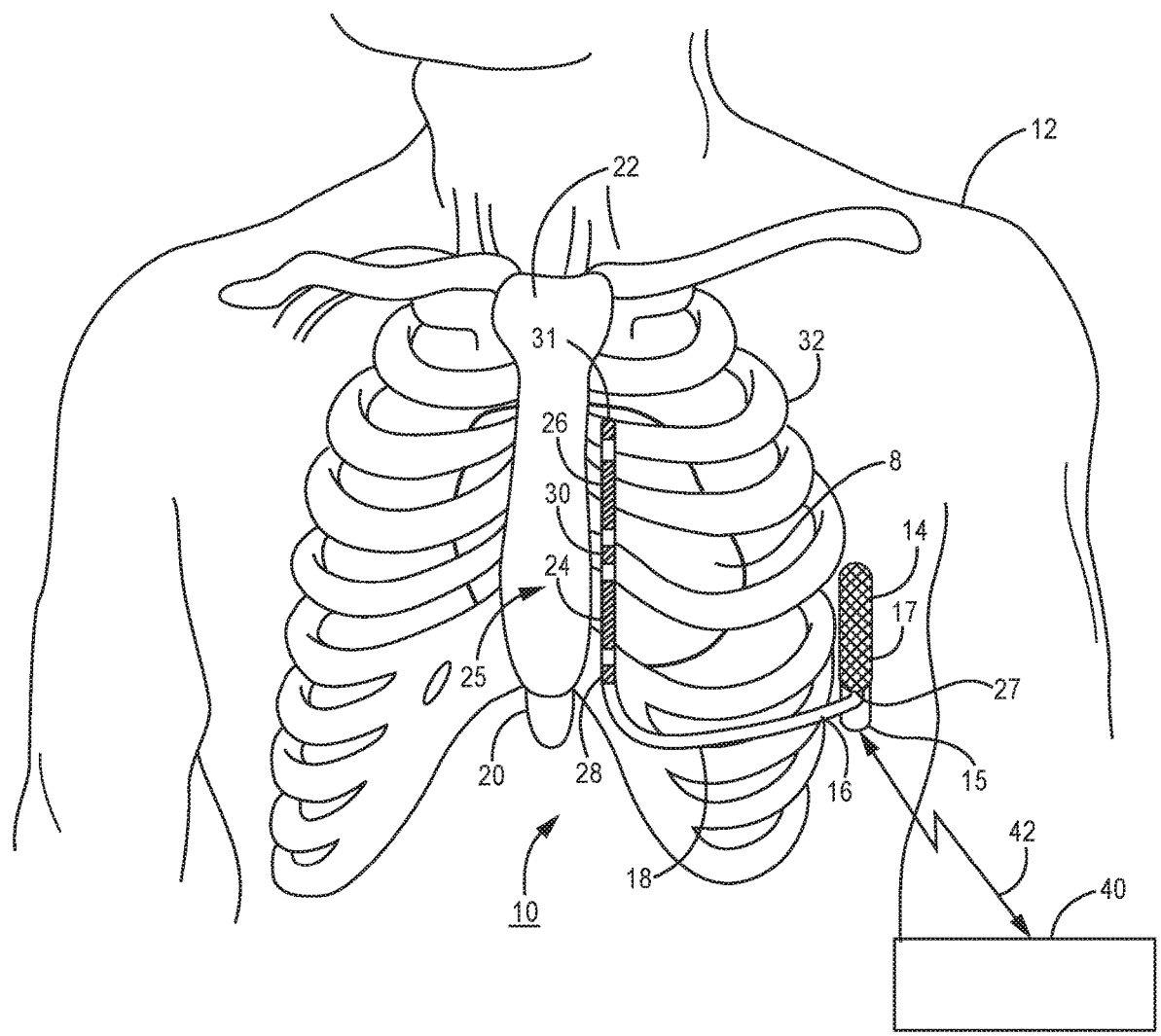
FIGS. 1A and 1B are conceptual diagrams of an extra-cardiovascular ICD system according to one example.
Figure 1B:
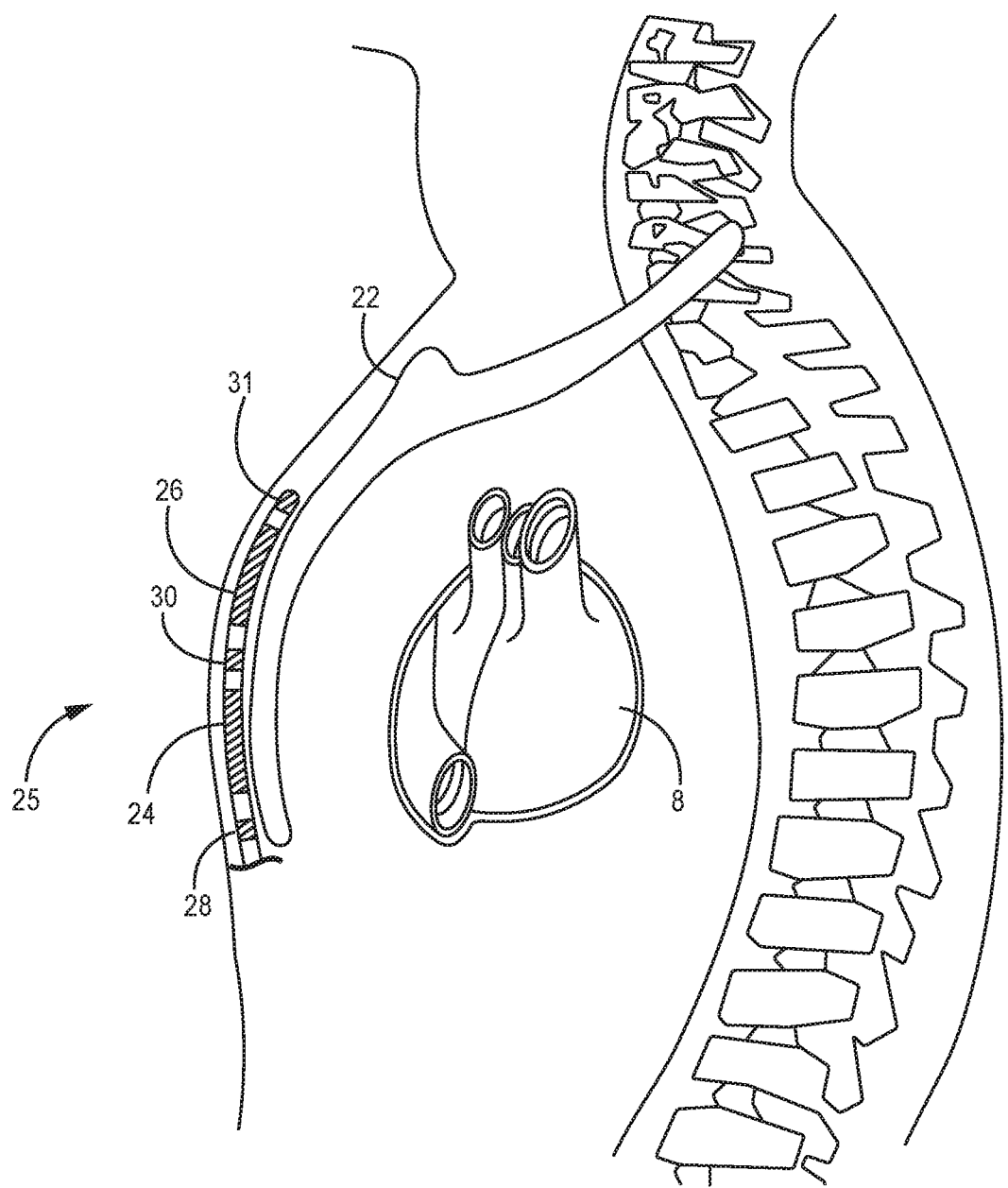

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and for sensing cardiac electrical signals in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect VT and VF.

Electrodes 28, 30 and 31 are relatively smaller surface area electrodes which are available for use in sensing electrode vectors for sensing cardiac electrical signals and may be used for delivering low voltage pacing pulses in some configurations. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

ICD 14 may obtain cardiac electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15. Various sensing electrode vectors utilizing combinations of electrodes 24, 26, 28, 30 and 31 and housing 15 are described below for acquiring first and second cardiac electrical signals using first and second sensing electrode vectors, respectively, selected by sensing circuitry including in ICD 14.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16 and are not limited to the positions shown. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31, which may be separate respective insulated conductors within the lead body. The respective conductors electrically couple the electrodes 24, 26, 28, 30 and 31 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 analyzes the cardiac electrical signals received from one or more of the sensing electrode vectors to monitor for abnormal rhythms, such as bradycardia, VT or VF. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead body 18. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the EMI detection techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
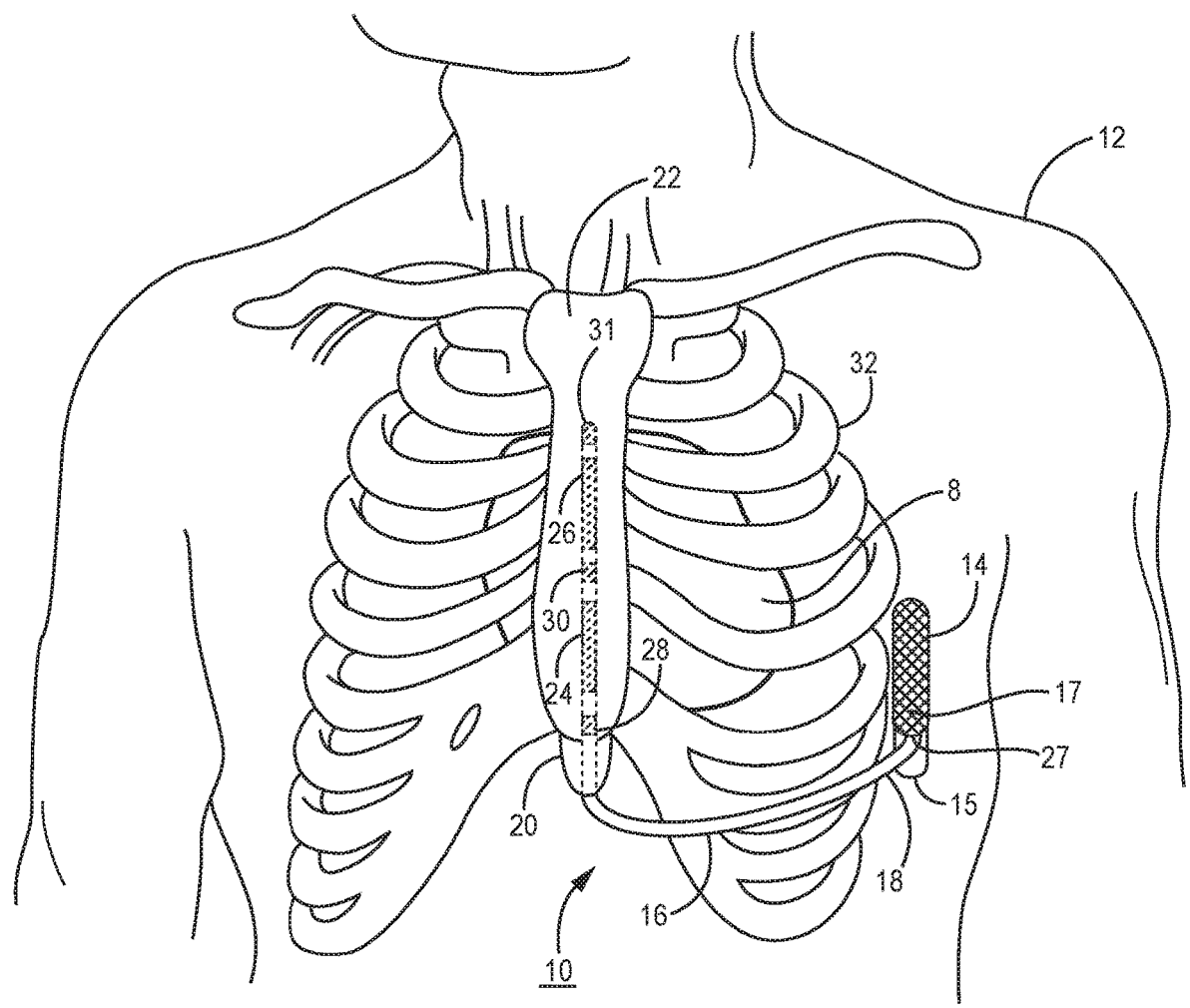
FIGS. 2A-2C are conceptual diagrams of a patient implanted with the extra-cardiovascular ICD system of FIG. 1A in a different implant configuration.
Figure 2B:
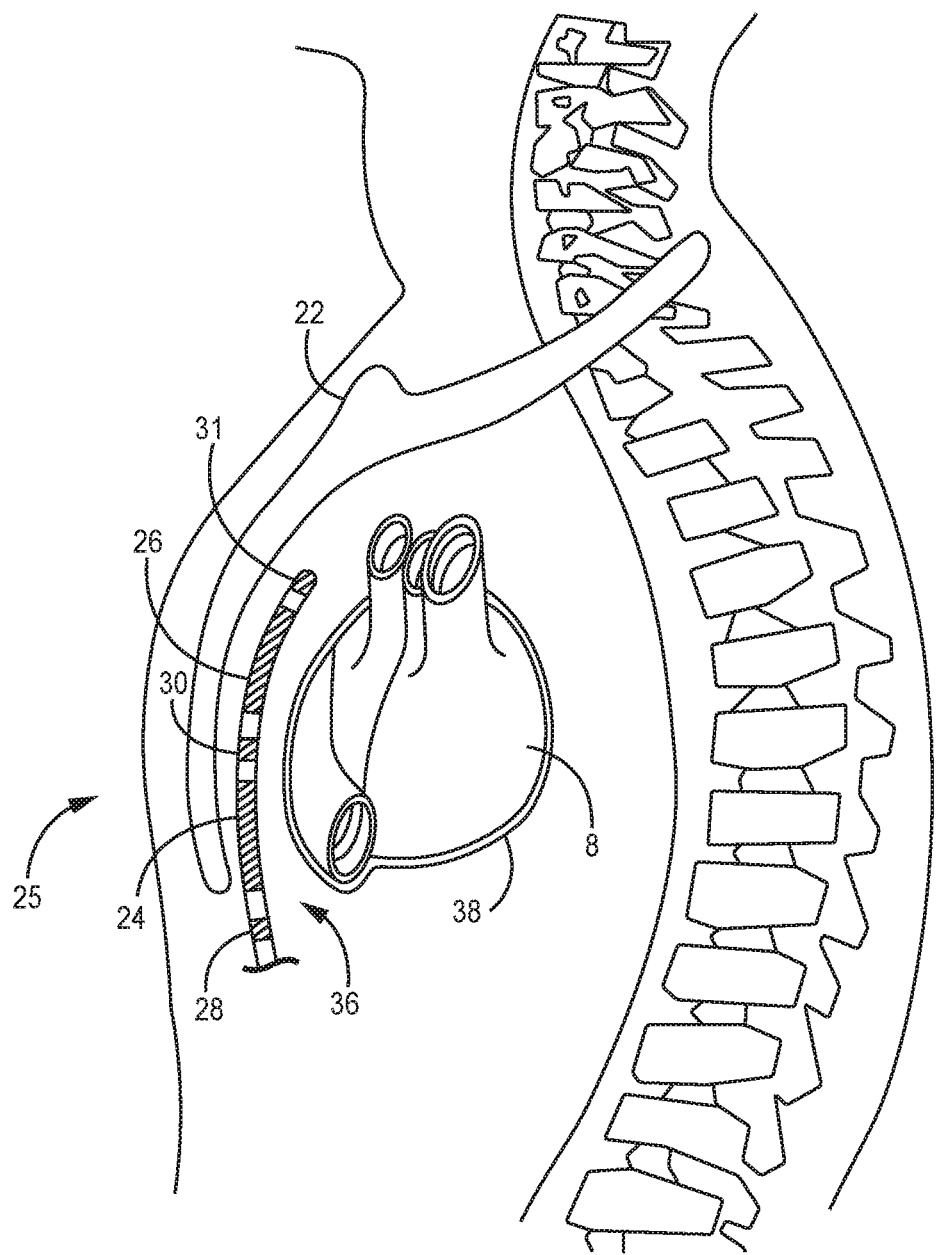
Figure 2C:
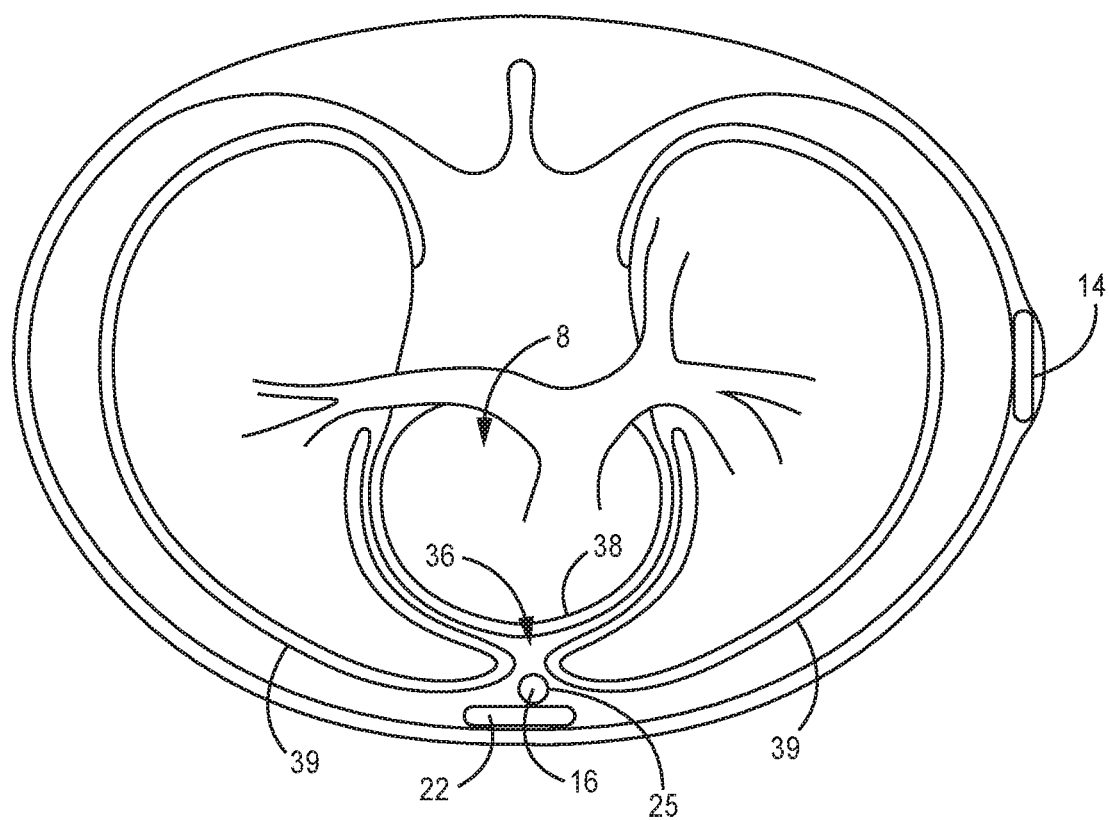

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the EMI detection techniques described herein are generally disclosed in the above-incorporated references.

Figure 3:
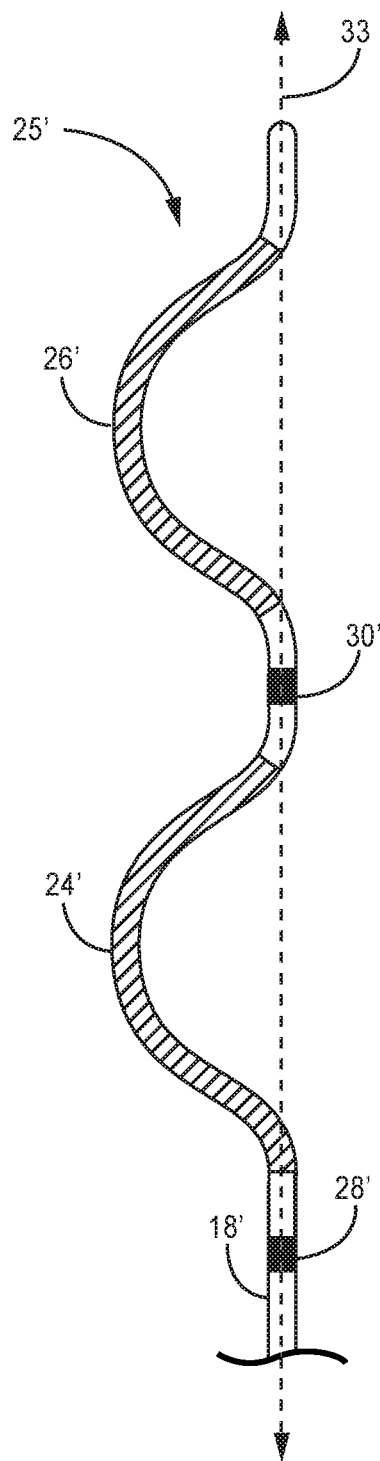
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, undulating or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in pending U.S. Pat. Publication No. 2016/0158567 (Marshall, et al.), incorporated herein by reference in its entirety.

Figure 4:
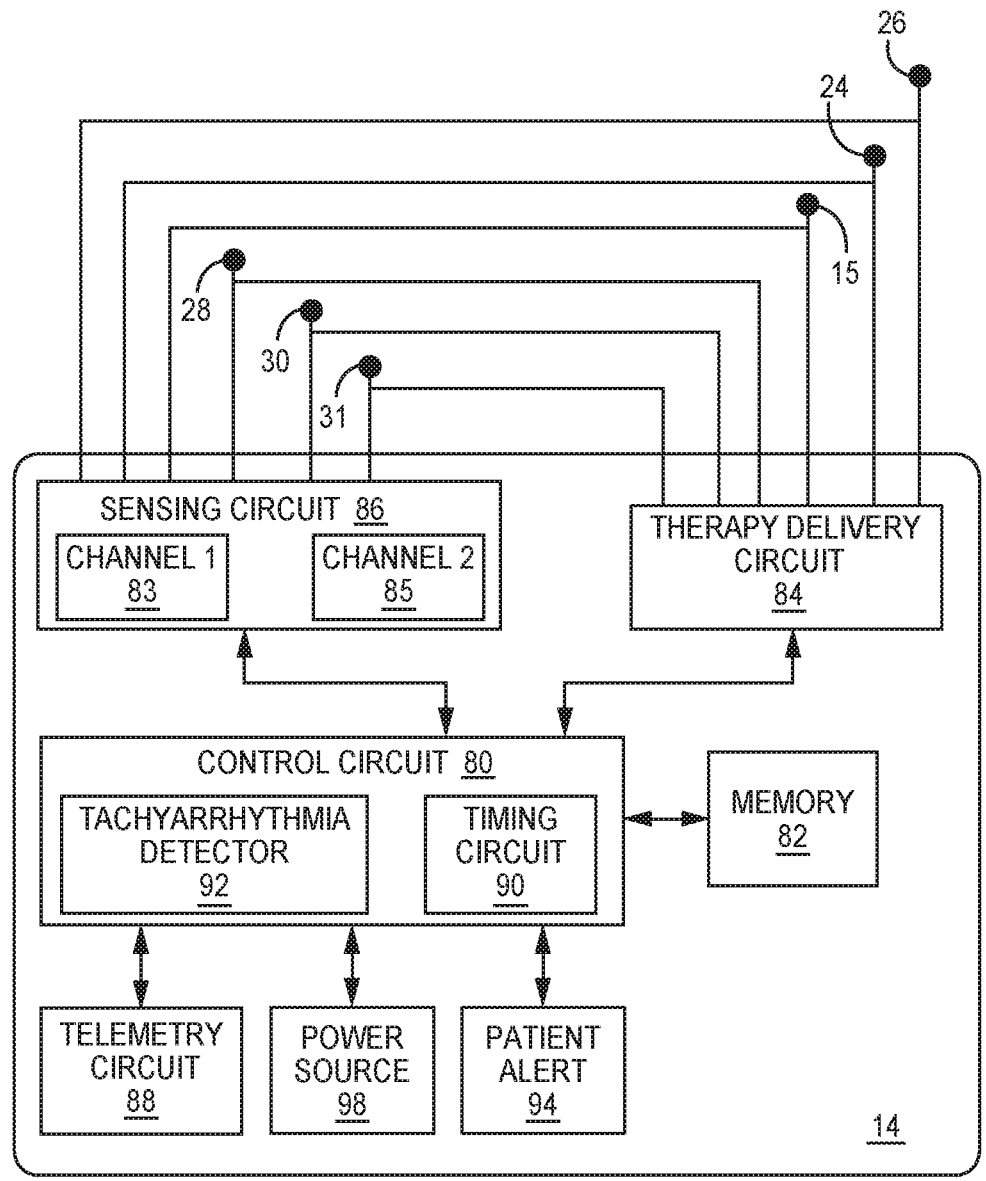
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT from VF for determining when ATP or CV/DF shocks are required. ICD 14 is coupled to an extra-cardiovascular lead, such as lead 16 carrying extra-cardiovascular electrodes 24, 26, 28, 30 and 31 (if present), for delivering electrical stimulation pulses to the patient's heart and for sensing cardiac electrical signals.

ICD 14 includes a control circuit 80, memory 82, therapy delivery circuit 84, sensing circuit 86, and telemetry circuit 88 and may include a patient alert circuit 94 in some examples. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol, such as for bradycardia pacing, post-shock pacing, ATP and/or CV/DF shock pulses. Power source 98 is also coupled to components of sensing circuit 86, such as sense amplifiers, analog-to-digital converters, switching circuitry, etc. as needed.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware or software components. Rather, functionality associated with one or more components may be performed by separate hardware, firmware or software components, or integrated within common hardware, firmware or software components. For example, cardiac event sensing and tachyarrhythmia detection operations may be performed by sensing circuit 86 under the control of control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 and 31 (if present as shown in FIGS. 1A and 2A) carried by lead 16 (e.g., as shown in FIGS. 1A-3) and the housing 15, which may function as a common or ground electrode or as an active can electrode for delivering CV/DF shock pulses or cardiac pacing pulses.

Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 may be enabled to selectively receive cardiac electrical signals from at least two sensing electrode vectors from the available electrodes 24, 26, 28, 30, 31 and housing 15. At least two cardiac electrical signals from two different sensing electrode vectors may be received simultaneously by sensing circuit 86, and sensing circuit 86 may monitor one or both or the cardiac electrical signals at a time for sensing cardiac electrical events. For example, sensing circuit 86 may include switching circuitry for selecting which of electrodes 24, 26, 28, 30, 31 and housing 15 are coupled to other components or circuits of sensing circuit 86. Switching circuitry may include a switch array, switch matrix, multiplexer, or any other type of switching device suitable to selectively couple components of sensing circuit 86 to selected electrodes.

In some examples, sensing circuit 86 includes multiple sensing channels 83 and 85 for acquiring cardiac electrical signals from multiple sensing vectors selected from electrodes 24, 26, 28, 30, 31 and housing 15 via the switching circuitry. Each sensing channel 83 and 85 may be configured to amplify, filter and digitize the cardiac electrical signal received from selected electrodes coupled to the respective sensing channel to improve the signal quality for detecting cardiac events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIGS. 5 and 11. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

For example, each sensing channel 83 and 85 may include a pre-filter and amplifier for filtering and amplifying a signal received from a selected pair of electrodes. The resulting raw cardiac electrical signal may be passed from the pre-filter and amplifier to cardiac event detection circuitry in at least one sensing channel 83 for sensing cardiac events from the received cardiac electrical signal in real time. As disclosed herein, the first sensing channel 83 may be configured to sense cardiac events such as R-waves based on a cardiac event sensing threshold, and the second sensing channel 85 may be configured to pass a digitized cardiac electrical signal obtained from a different sensing electrode vector to control circuit 80 for use in confirming a cardiac event sensed by first sensing channel 83.

Upon detecting a cardiac event based on a sensing threshold crossing, first sensing channel 83 may produce a sensed event signal, such as an R-wave sensed event signal, that is passed to control circuit 80. In some examples, the sensed event signal may be used by control circuit 80 to trigger storage of a time segment of the second cardiac electrical signal for post-processing and analysis for confirming the R-wave sensed event signal, for example as described in conjunction with FIG. 12.

The R-wave sensed event signals are also used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured RRIs, counts or other data for analysis by the tachyarrhythmia detector 92. Memory 82 may be configured to store a predetermined number of cardiac electrical signal segments in circulating buffers under the control of control circuit 80, e.g., at least one, two or other number of cardiac electrical signal segments. Each segment may be written to memory 82 over a time interval extending before and after the R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection.

When noise, such as EMI is present in the cardiac electrical signal(s) received by sensing circuit 86, false R-wave sensed event signals may be produced and passed to control circuit 80 when EMI noise spikes cross the R-wave sensing threshold. As described below in conjunction with FIG. 5, at least one sensing channel, e.g., sensing channel 83, may include a quiet timer that is started in response to the cardiac electrical signal crossing a noise threshold. In some examples, e.g., as described below in conjunction with FIGS. 8A and 8B, the quiet timer is started in response to each R-wave sensing threshold crossing that occurs outside a post-sense blanking period. The quiet timer is set to a quiet time interval which begins to count down to zero but is reset to the quiet time interval if the R-wave sensing threshold is crossed by the cardiac electrical signal again prior to the expiration of the quiet time interval. Aspects of the quiet timer disclosed in pending U.S. Publication No. 2015/0305642 (Reinke, et al.), incorporated herein by reference in its entirety, may be implemented in the quiet timer included in sensing circuit 86.

Figure 9:
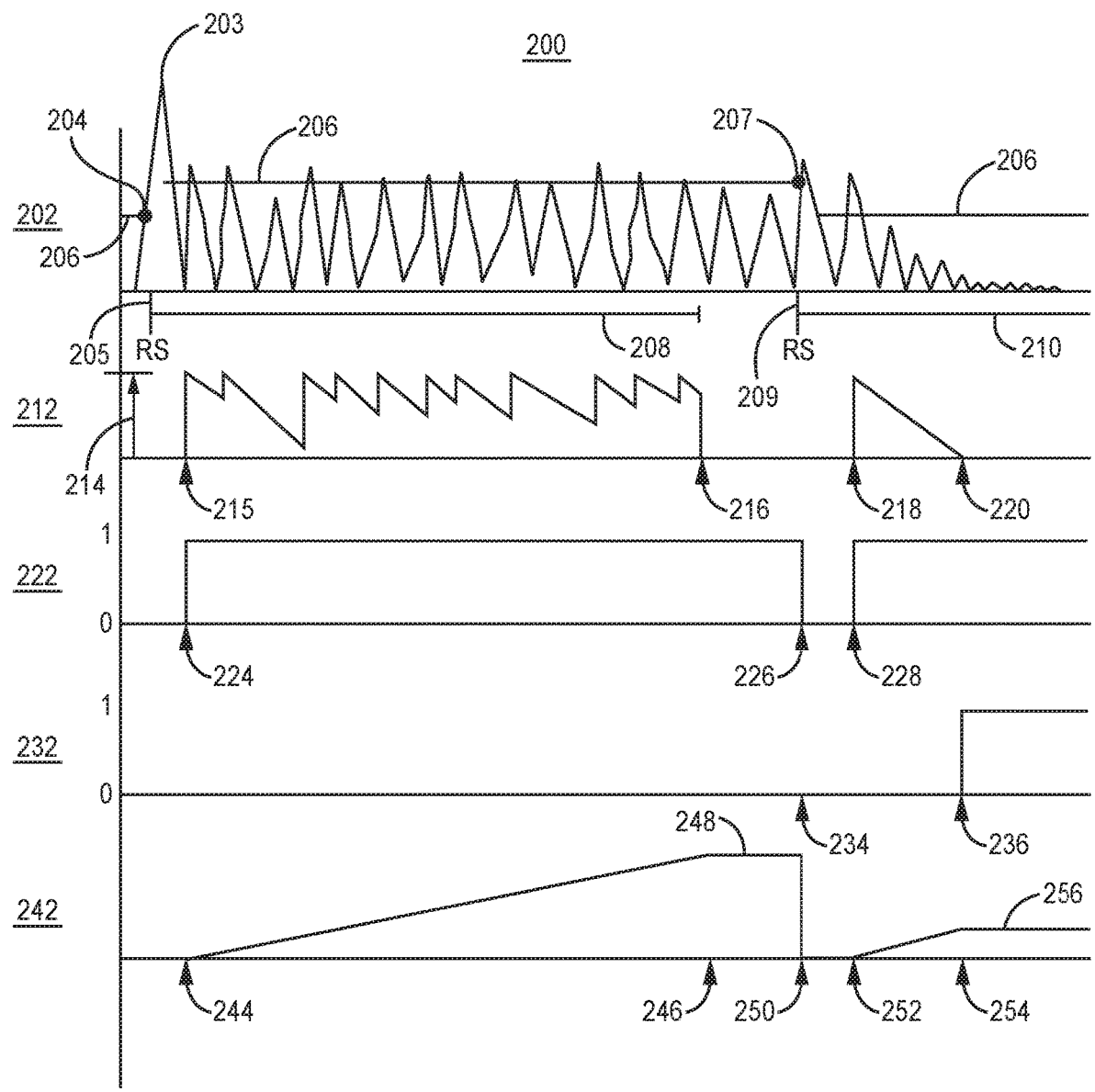
FIG. 9 is a schematic diagram of the operation of a quiet timer and corresponding quiet timer behavior parameters according to another example.
Figure 10:
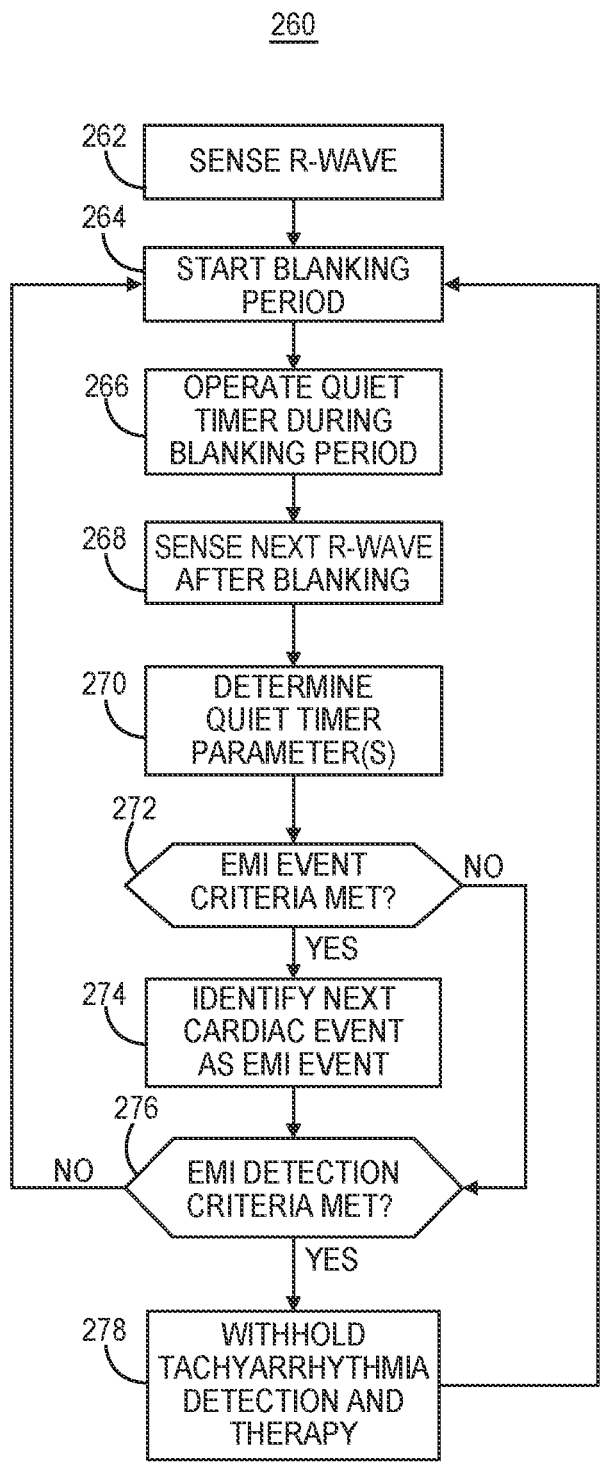
FIG. 10 is a flow chart of a method for detecting EMI for withholding tachyarrhythmia detection according to another example.

In other examples, e.g., as described in conjunction with FIGS. 9 and 10, the quiet timer is enabled to operate during an EMI monitoring interval. During the monitoring interval, the quiet timer is started in response to the cardiac electrical signal crossing a noise threshold. The noise threshold may be set equal to the R-wave sensing threshold, and the EMI monitoring interval may be the post-sense blanking period set by sensing circuit 86 after an R-wave is sensed. The quiet timer is started by setting the timer to a quiet time interval that counts down on each sampling interval and will time out if the cardiac electrical signal does not cross the noise threshold again during the quiet time interval. If another noise threshold crossing occurs before the quiet time interval expires, however, the quiet timer is reset to the quiet time interval, so the quiet timer starts counting down from the quiet time interval again.

Depending on the frequency of EMI that may be present, the quiet timer may be reset to the quiet time interval multiple times after being started. During the post-sense blanking period, the sensing circuit 86 does not produce R-wave sensed event signals in response to R-wave sensing threshold crossing. When the post-sense blanking period ends, the next R-wave sensing threshold crossing may result in an R-wave sensed event signal being produced and passed to control circuit 80. According to techniques disclosed herein, control circuit 80 may determine one or more quiet timer parameters indicative of the behavior of the quiet timer since the last sensed R-wave or during an EMI monitoring interval (which may be the most recent post-sense blanking period) that preceded the currently sensed R-wave. Behavior of the quiet timer prior to the currently sensed R-wave may be indicative of EMI.

For example, quiet timer parameters that may be determined by control circuit 80 may include a quiet timer status indicating the status of the quiet timer at the time of or just prior to the next sensed R-wave or upon expiration of the EMI monitoring interval. The quiet timer status may be set to a first value indicating that the quiet timer is still running and has not expired and set to a second value indicating that the quiet time interval expired and the quiet timer has timed out.

Another example of a quiet timer parameter that may be determined by control circuit 80 is a quiet timer time out status. The time out status indicates whether or not the quiet timer timed out. When the quiet timer times out, a time out interrupt signal may be produced by sensing circuit 86. The time out status may be set high in response to the interrupt signal and set low if no time out interrupt signal has been received since the quiet timer was started.

In the presence of EMI, the quiet timer may be reset multiple times such that the quiet time interval does not expire prior to the next sensed R-wave. Another example of a quiet timer parameter that may be determined by control circuit 80 is a quiet timer count or quiet timer ON time value indicating the total time the quiet timer was running until timing out (or until the time of the next sensed R-wave if the quiet timer has not yet timed out). Various examples of quiet timer parameters and how they are determined are described below in conjunction with the timing diagrams of FIGS. 8A, 8B and 9 and the flow charts of FIGS. 6, 7 and 10.

Quiet timer parameters may be determined by control circuit 80 and used to detect EMI for withholding a tachyarrhythmia detection made by tachyarrhythmia detector 92. Tachyarrhythmia detector 92 is configured to analyze signals received from sensing circuit 86 for detecting tachyarrhythmia episodes. Tachyarrhythmia detector 92 may be implemented in control circuit 80 as software, hardware and/or firmware that processes and analyzes signals received from sensing circuit 86 for detecting VT and/or VF. In some examples, tachyarrhythmia detector 92 may include comparators and counters for counting RRIs determined by timing circuit 92 that fall into various rate detection zones for determining a ventricular rate or performing other rate- or interval-based assessments for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. When an interval counter reaches a detection threshold, a ventricular tachyarrhythmia may be detected by tachyarrhythmia detector 92. Tachyarrhythmia detector 92 may be configured to perform other signal analysis for determining if other detection criteria are satisfied before detecting VT or VF, such as R-wave morphology criteria, onset criteria, and noise and oversensing rejection criteria. As disclosed herein, tachyarrhythmia detector 92 may withhold a VT or VF detection when an interval counter is reached in response to an R-wave sensed event signal that is identified as an EMI event based on quiet timer parameters.

Examples of other parameters that may be determined from cardiac electrical signals received by sensing circuit 86 for determining the status of tachyarrhythmia detection rejection rules that may cause withholding to a VT or VF detection are described in provisional U.S. Patent Application 62/367,166, provisional U.S. Patent Application 62/367,170, provisional U.S. Patent Application 62/367,221, all filed on Jul. 27, 2016, and in pending U.S. patent application Ser. No. 15/140,802 (Zhang et al., filed Apr. 28, 2016), all of which are incorporated herein by reference in their entirety. To support additional cardiac signal analyses performed by tachyarrhythmia detector 92, sensing circuit 86 may pass a digitized cardiac electrical signal to control circuit 80 for morphology analysis performed by tachyarrhythmia detector 92 for detecting and discriminating heart rhythms. A cardiac electrical signal from the selected sensing vector, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82. Memory 82 may include one or more circulating buffers to temporarily store digital cardiac electrical signal segments for analysis performed by control circuit 80 to confirm R-waves sensed by sensing channel 83. In some examples, morphology analysis is performed to determine signal morphology parameters used in combination with quiet timer parameters for detecting EMI, e.g., as described below in conjunction with FIG. 12.

Control circuit 80 may include a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. Examples of devices and algorithms that may be adapted to utilize techniques for EMI detection described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Timing circuit 90 of control circuit 80 may include various timers or counters that control when ATP or other cardiac pacing pulses are delivered. For example, timing circuit 90 may include programmable digital counters set by a microprocessor of the control circuit 80 for controlling the basic time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, ATP and/or CV/DF therapy may be delivered. ATP therapy can be delivered by loading a regimen from the microprocessor included in control circuit 80 into timing circuit 90 according to the type and rate of tachycardia detected. In response to detecting VT or VF, CV/DF therapy can be delivered by initiate charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line passed to therapy delivery circuit 84, terminating charging. The CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. Therapy delivery and control circuitry generally disclosed in any of the above-incorporated patents may be implemented in ICD 14.

Furthermore it is recognized that the methods disclosed herein may be implemented in an implantable medical device that is used for monitoring cardiac electrical signals by sensing circuit 86 and control circuit 80 without having therapy delivery capabilities or in an implantable medical device that monitors cardiac electrical signals and delivers cardiac pacing therapies by therapy delivery circuit 84, without high voltage therapy capabilities, such as cardioversion/defibrillation shock capabilities.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Control circuit may control telemetry circuit 88 to transmit an EMI alert signal in response to detecting EMI events and updating an EMI index that meets EMI alert criteria. In other examples, ICD 14 may include a patient alert circuit 94 that may be controlled by control circuit 80 to generate an alert signal, such as a vibration or audible tone, which is perceivable by the patient. For example, patient alert 94 may include a vibrating circuit that is activated by control circuit 80 in response to determining that an index of EMI events meets patient alert criteria. The patient may be prospectively instructed to move away from an EMI environment upon perceiving the patient alert. Determining an EMI index and generating an EMI alert by ICD 14 is further described below in conjunction with FIG. 15.

Figure 5:
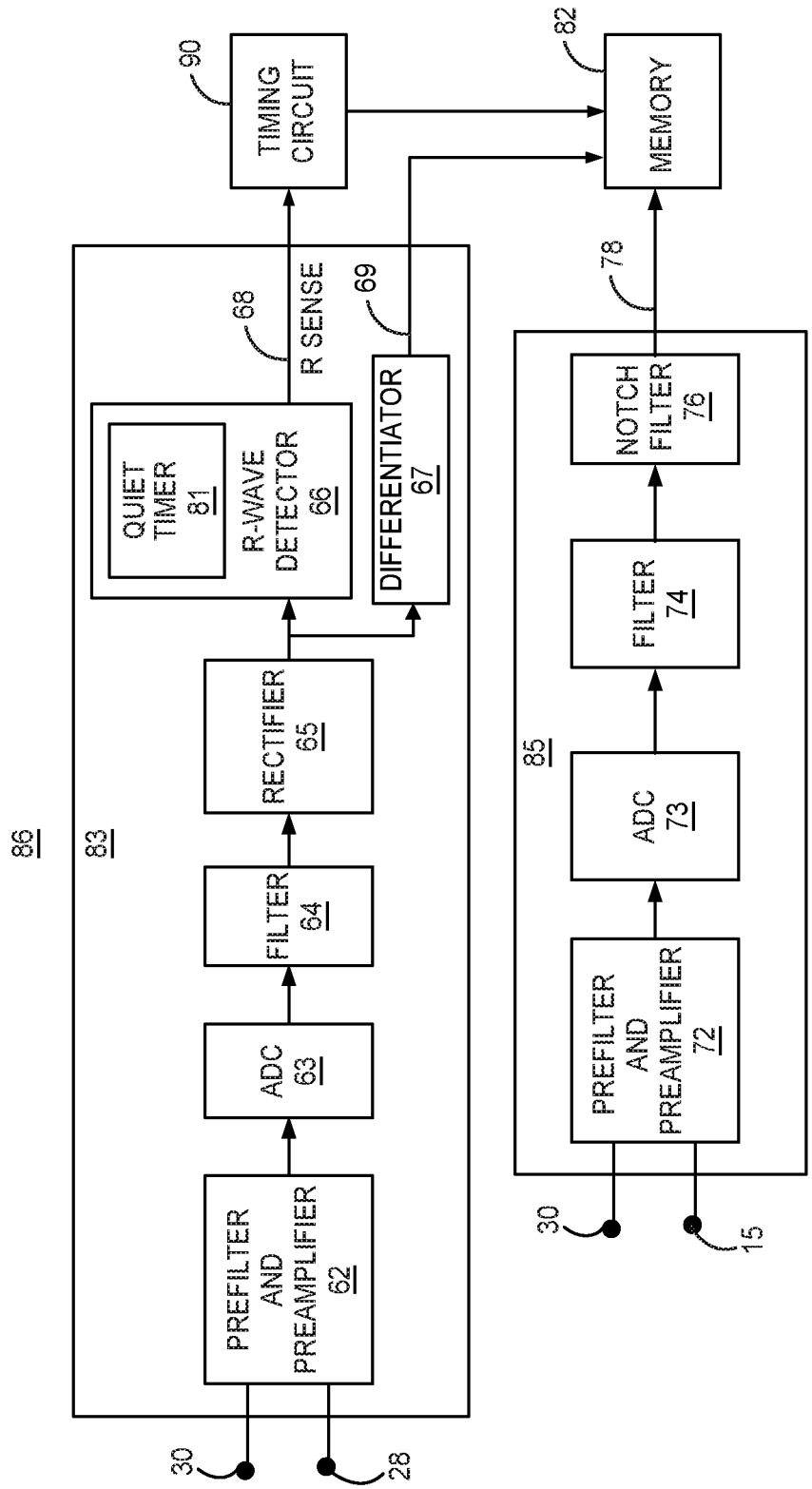
FIG. 5 is diagram of circuitry included in the sensing circuit of FIG. 4 according to one example.

FIG. 5 is a diagram of circuitry included in first sensing channel 83 and second sensing channel 85 of sensing circuit 86 according to one example. First sensing channel 83 may be selectively coupled via switching circuitry (not shown) to a first sensing electrode vector including electrodes carried by extra-cardiovascular lead 16 as shown in FIGS. 1A-2C for receiving a first cardiac electrical signal. First sensing channel 83 may be coupled to a sensing electrode vector that is a short bipole, having a relatively shorter inter-electrode distance or spacing than the second electrode vector coupled to second sensing channel 85. In the example shown, the first sensing electrode vector may include pace/sense electrodes 28 and 30. In other examples, the first sensing electrode vector coupled to sensing channel 83 may include pace/sense electrodes 30 and 31 and in some cases pace/sense electrodes 28 and 31 depending on the inter-electrode spacing and position of the distal portion 25 of lead 16. In some cases, the first sensing channel 83 may be selectively coupled to a sensing electrode vector including a defibrillation electrode 24 and/or 26, e.g., a sensing electrode vector between pace/sense electrode 28 and defibrillation electrode 24, between pace/sense electrode 30 and either of defibrillation electrodes 24 or 26, or between pace/sense electrode 26 and 31. In still other examples, the first sensing electrode vector may be between defibrillation electrodes 24 and 26.

In some patients, a bipole between electrodes carried by lead 16 may result in patient body posture dependent changes in the cardiac electrical signal as the sensing vector of the bipole relative to the cardiac axis changes with changes in patient body posture or body motion. Accordingly, the sensing electrode vector coupled to the first sensing channel 83 may include housing 15 and any of the electrodes 24, 26, 28, 30 and 31 carried by lead 16. A relatively longer bipole including housing 15 and a lead-based electrode may be less sensitive to positional changes but may be more susceptible to EMI. The techniques disclosed herein may be used to detect EMI to avoid oversensing of EMI leading to false detection of VT and VF and unnecessary electrical stimulation therapies.

Sensing circuit 86 includes a second sensing channel 85 that receives a second cardiac electrical signal from a second sensing vector, for example from a vector that includes electrode 30 and housing 15, as shown, or a vector that includes electrode 28 and housing 15. Second sensing channel 85 may be selectively coupled to other sensing electrode vectors, which may form a relatively long bipole having an inter-electrode distance or spacing that is greater than the sensing electrode vector coupled to first sensing channel 83 in some examples. As described below, the second cardiac electrical signal received by second sensing channel 85 via a long bipole may be used by control circuit 80 for morphology analysis (including noise rejection and other analyses, for example as described in conjunction with FIG. 12). In other examples, any vector selected from the available electrodes, e.g., electrodes 24, 26, 28, 30 and/or 31 and/or housing 15 may be included in a sensing electrode vector coupled to second sensing channel 85. The sensing electrode vectors coupled to first sensing channel 83 and second sensing channel 85 are typically different sensing electrode vectors, which may have no common electrodes or only one common electrode but not both.

In the illustrative example shown in FIG. 5, the electrical signals developed across input electrodes 28 and 30 are received by sensing channel 83 and electrical signals developed across electrodes 30 and 15 are received by sensing channel 85. The electrode vectors are shown for the sake of illustration and different sensing vectors may be selectively coupled to sensing channels 83 and 85. The cardiac electrical signals are provided as differential input signals to the pre-filter and pre-amplifiers 62 and 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

In sensing channel 83, the digital output of ADC 63 is passed to filter 64 which may be a digital bandpass filter having a bandpass of approximately 10 Hz to 30 Hz for passing cardiac electrical signals such as R-waves typically occurring in this frequency range. The bandpass filtered signal is passed from filter 64 to rectifier 65 then to R-wave detector 66. R-wave detector 66 may include an auto-adjusting sense amplifier, comparator and/or other detection circuitry that compares the filtered and rectified first cardiac electrical signal to an R-wave sensing threshold in real time and produces an R-wave sensed event signal 68 when the cardiac electrical signal crosses the R-wave sensing threshold outside of a post-sense blanking period.

The R-wave sensing threshold, controlled by sensing circuit 86 and/or control circuit 80, may be a multi-level sensing threshold as disclosed in pending U.S. patent application Ser. No. 15/142,171 (Cao, et al., filed on Apr. 29, 2016), incorporated herein by reference in its entirety. Briefly, the multi-level sensing threshold may have a starting sensing threshold value held for a time interval equal to a tachycardia detection interval, then drops to a second sensing threshold value held until a drop time interval expires, which may be 1 to 2 seconds long. The sensing threshold drops to a minimum sensing threshold after the drop time interval. The starting sensing threshold value may be the lower of a predetermined percentage of the most recent, preceding sensed R-wave peak amplitude and a maximum sensing threshold limit determined using a sensitivity-dependent gain and the programmed sensitivity setting. In other examples, the R-wave sensing threshold used by R-wave detector 66 may be set to a starting value based on a preceding R-wave peak amplitude and decay linearly or exponentially over time until reaching a minimum sensing threshold. However, the techniques of this application are not limited to a specific behavior of the sensing threshold. Instead, other decaying, step-wise adjusted or other automatically adjusted sensing thresholds may be utilized.

The R-wave detector 66 of first sensing channel 83, configured for sensing R-waves in real time in the example shown, may include a quiet timer 81 that is monitored by control circuit 80 for use in detecting EMI. The quiet timer 81 may be set to a quiet time interval of 10 ms, 20 ms, 25 ms, 30 ms, 40 ms, or other predetermined time interval in response to the sensed R-wave. The quiet time interval may be set according to the lowest frequency of noise signals that are to be detected as EMI. R-wave detector 66 may set a post-sense blanking period following a sensed R-wave. The post-sense blanking period may be 100 to 180 ms long in some examples R-wave sensing threshold crossings that may occur during the post-sense blanking period are not sensed as R-waves, and no R-wave sensed event signal is generated. An R-wave sensing threshold crossing during the blanking period, however, may cause quiet timer 81 to be reset to the predetermined quiet time interval. In some instances, if an R-wave sensing threshold crossing occurs before the quiet timer expires, the quiet timer 81 is reset to the predetermined quiet time interval. In other examples, the quiet timer may be started and reset in response to the cardiac electrical signal crossing a noise threshold amplitude set by control circuit 80 that is different than the R-wave sensing threshold used to sense R-waves.

For example, the starting R-wave sensing threshold after the post-sense blanking period may be set to a percentage of the maximum peak amplitude determined during a peak tracking time interval following the R-wave sensing threshold crossing, during the post-sense blanking period. The noise threshold for resetting the quiet timer during the post-sense blanking period may be held at the amplitude at which the sensing threshold crossing occurred or set to a percentage of the maximum peak amplitude of the most recently sensed signal. For instance, a starting R-wave sensing threshold may be 53% of the maximum peak amplitude during a peak tracking time interval which overlaps at least a portion of the post-sense blanking period, and the noise threshold used to reset the quiet timer during the post-sense blanking period may be set to 35% of a maximum amplitude of the sensed event or a percentage (e.g., 50%, 100%, etc.) of the amplitude at which the R-wave sensing threshold crossing occurred causing an R-wave sensed event signal. The quiet timer 81 may be started in response to sensing an R-wave based on the R-wave sensing threshold and may be reset in response to the cardiac electrical signal crossing the noise threshold during the post-sensing blanking period.

In the presence of EMI, the quiet timer 81 may be started one or more times and, once started, may be reset one or more times due to multiple EMI noise spikes. An R-wave may be sensed early after the post-sense blanking period, starting the next post-sense blanking period, during which the quiet timer 81 may be reset again one or more times. As described below, control circuit 80 may determine one or more quiet timer parameters that represent the behavior of the quiet timer since the most recent sensed R-wave. For example, control circuit 80 may determine if the quiet timer 81 timed out since being started in response to a sensed R-wave or if the quiet timer 81 was started and/or timed out during an EMI monitoring interval. The quiet timer 81 times out when the timer counts down from the quiet time interval to zero without being reset to the quiet time interval due to an R-wave sensing threshold (or other noise threshold) crossing.

In some examples, the filtered, digitized cardiac electrical signal from sensing channel 83, e.g., output of filter 64, may be stored in memory 82 for signal processing by control circuit 80 for use in detecting tachyarrhythmia episodes. In one example, the output of rectifier 65 is passed to differentiator 67 which determines an Nth order differential signal 69 that is passed to memory 82. The differential signal 69 is also sometimes referred to as a "difference signal" because each sample point of the differential signal 69 may be determined as the difference between the ith input sample point and a corresponding i-N input sample point. Control circuit 80 may retrieve the stored signal from memory 82 for performing signal analysis by tachyarrhythmia detector 92 according to implemented tachyarrhythmia detection algorithms.

The second cardiac electrical signal, digitized by ADC 73 of sensing channel 85, may be passed to filter 74 for bandpass filtering. In some examples, filter 74 is a wideband filter for passing frequencies from 1 to 30 Hz or from 1 to 100 Hz. In some examples, sensing channel 85 includes notch filter 76. Notch filter 76 may be implemented in firmware or hardware and is provided to attenuate 50-60 Hz electrical noise, muscle noise, EMI or electrical noise/artifacts in the second cardiac electrical signal. Cardiac electrical signals acquired using extra-cardiovascular electrodes as shown, for example in FIGS. 1A-3, may be more likely to be contaminated by 50-60 Hz electrical noise, muscle noise and other EMI, electrical noise/artifacts than intra-cardiac electrodes. As such, notch filter 76 may be provided to significantly attenuate the magnitude of signals in the range of 50-60 Hz with minimum attenuation of signals in the range of approximately 1-30 Hz, corresponding to typical cardiac electrical signal frequencies.

The output signal 78 of notch filter 76 may be passed from sensing circuit 86 to memory 82 under the control of control circuit 80 for storing segments of the second cardiac electrical signal 78 in temporary buffers of memory 82. For example, timing circuit 90 of control circuit 80 may set a time interval or number of sample points relative to an R-wave sensed event signal 68 received from first sensing channel 83, over which the second cardiac electrical signal 78 is stored in memory 82. The buffered, second cardiac electrical signal segment may be analyzed by control circuit 80 on a triggered, as needed basis, as described in conjunction with FIG. 12, to confirm R-waves sensed by the first sensing channel 83 or for detecting EMI events falsely sensed as R-waves.

Notch filter 76 may be implemented as a digital filter for real-time filtering performed by firmware as part of sensing channel 85 or by control circuit 80 for filtering the buffered digital output of filter 74. In some examples, the output of filter 74 of sensing channel 85 may be stored in memory 82 in time segments defined relative to an R-wave sense event signal 68 prior to filtering by notch filter 76. When control circuit 80 is triggered to analyze the stored, second cardiac electrical signal for confirming an R-wave sensed event signal, for example as described in conjunction with FIG. 12, the notch filter 76 may be applied to the stored segment of the second cardiac electrical signal before further processing and analysis of the stored segment. In this way, if analysis of the stored signal segment is not required for confirming an R-wave sensed by first sensing channel 83, firmware implemented to perform the operation of notch filter 76 need not be executed.

The configuration of sensing channels 83 and 85 shown in FIG. 5 is illustrative in nature and should not be considered limiting of the techniques described herein. The sensing channels 83 and 85 of sensing circuit 86 may include more or fewer components than illustrated and described in FIG. 5. First sensing channel 83 may be configured to detect R-waves in real time, e.g., in hardware implemented components, from a first cardiac electrical signal based on crossings of an R-wave sensing threshold by the first cardiac electrical signal, and second sensing channel 85 may be configured to provide a second cardiac electrical signal for storage in memory 82 for post-processing and analysis by control circuit 80 for confirming R-wave sensed event signals produced by the first sensing channel 83 as needed. In other examples, such as the example in FIG. 13, both sensing channels 83 and 85 may be capable of sensing R-waves in real time and operating a quiet timer for detecting EMI events.

The examples provided herein generally relate to R-wave sensing by an extra-cardiovascular ICD, e.g., ICD 14, for determining RRIs in a ventricular tachyarrhythmia detection algorithm. It is to be understood, however, that EMI may be detected in a cardiac electrical signal during P-wave sensing to avoid oversensing of EMI during atrial rhythm detection algorithms. For example, an ICD or other implantable device may be configured for sensing P-waves and detecting atrial tachyarrhythmias. In that case, sensing circuit 86 may be configured with a P-wave detector instead of or in addition to R-wave detector 66.

Figure 6:
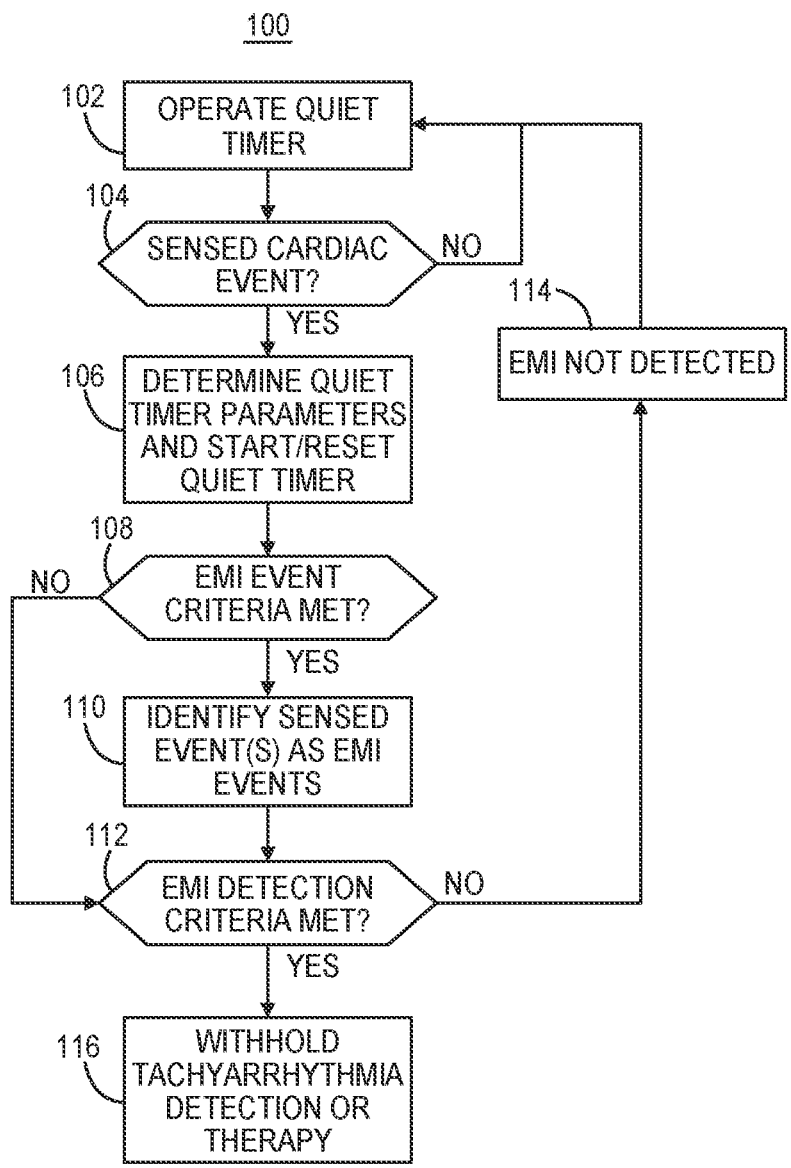
FIG. 6 is a flow chart of a method performed by an extra-cardiovascular ICD for detecting EMI according to one example.

FIG. 6 is a flow chart 100 of a method performed by ICD 14 for detecting EMI according to one example. Quiet timer operation is generally described herein based on sensing R-waves and identifying a sensed R-wave as an EMI event based on the behavior of the quiet timer 81. It is contemplated, however, that the process of flow chart 100 and other flow charts presented herein for detecting EMI may be performed during P-wave sensing, in which case the quiet timer 81 may be started in response to a sensed P-wave and reset in response to a cardiac electrical signal crossing a P-wave sensing threshold prior to the quiet time interval expiring.

At block 102, control circuit 80 controls sensing circuit 86 to receive a cardiac electrical signal for sensing cardiac events and operating quiet timer 81. In one example, the operation of quiet timer 81 includes starting quiet timer 81 in response to a cardiac event sensed outside a blanking period. The quiet timer 81 is started by setting the quiet timer 81 to a quiet time interval. Operation of quiet timer 81 at block 102 may further include resetting the quiet timer to the quiet time interval in response to each crossing of a noise threshold that occurs prior to the quiet timer timing out. The noise threshold may be equal to the cardiac event sensing threshold, e.g., an R-wave sensing threshold. If the quiet timer 81 times out before the next noise threshold crossing, sensing circuit 86 may generate a quiet timer time out interrupt signal that is passed to control circuit 80.

In some examples, the quiet timer 81 is operated continuously in that it is enabled to be started in response to each sensed cardiac event. In other examples, control circuit 80 enables sensing circuit 86 to operate the quiet timer 81 in response to detecting a threshold number of cardiac event intervals that are less than an interval threshold such as a tachyarrhythmia detection interval. As long as tachyarrhythmia intervals are not being detected, identifying EMI events and detection of EMI may not be necessary. Once a threshold number of tachyarrhythmia intervals are detected, however, EMI detection based on quiet timer behavior may be enabled in order to reduce the likelihood of false tachyarrhythmia detection based on EMI events.

In one example, the quiet timer operation is controlled based on the same cardiac electrical signal from which the cardiac events are sensed. For example, first sensing channel 83 may sense R-waves by R-wave detector 66 from a first cardiac electrical signal received by first sensing channel 83. The quiet timer 81 may be started in response to the sensed R-wave and may be reset to the quiet time interval in response to the first cardiac electrical signal crossing the R-wave sensing threshold before the quiet timer times out. In other examples, the quiet timer 81 may be included in the second sensing channel 85 and may be started (and reset) when the second cardiac electrical signal received by the second sensing channel crosses a noise threshold amplitude.

At block 104, a cardiac event is sensed. In the illustrative examples presented herein, the cardiac event is an R-wave sensed by R-wave detector 66 of sensing channel 83. As indicated above, however, that the process of flow chart 100 for detecting EMI may be performed during P-wave sensing, in which case the sensed cardiac event at block 104 is a P-wave.

At block 106, control circuit 80 determines one or more quiet timer parameters. A quiet timer parameter may be determined based on the status of the quiet timer just prior to or at the time of the sensing threshold crossing by the cardiac electrical signal which caused the sensed cardiac event at block 104 The quiet timer parameters indicate the behavior of the quiet timer just prior to the sensed cardiac event. For example, the quiet timer parameters may include a bit register that may be set high to indicate the quiet timer 81 is active (has not timed out) or set low indicating the quiet timer is not active (has timed out). In other examples, the quiet timer parameters may include a bit register value indicating whether a time out interrupt was generated in response to the quiet timer 81 timing out. Another example of a quiet timer parameter is a quiet timer ON time parameter indicating how long the quiet timer 81 was running before timing out or before the cardiac event was sensed at block 104. Other quiet timer parameters may indicate if the quiet timer 81 was reset before timing out and/or how many times the quiet timer 81 was reset.

At block 108 the quiet timer parameter(s) is(are) compared to EMI event criteria in response to sensing the cardiac event at block 104 for determining if the sensed event is likely an EMI event. Example EMI event criteria may include the quiet timer status being active (not timed out) at the time of the sensed cardiac event. Additionally or alternatively, EMI event criteria may require that no quiet timer interrupt signal was generated since the last cardiac event was sensed. In other examples, the quiet timer 81 may be required to be on for a threshold ON time interval before timing out. Another example of EMI event criteria may require that the quiet timer 81 be reset at least once or a higher threshold number of times prior to the cardiac event being sensed at block 104. Example techniques for determining quiet timer parameters and applying EMI event criteria are described in greater detail below in conjunction with FIGS. 7 through 10.

If the quiet timer parameter(s) does(do) not satisfy the EMI event criteria at block 108, the event is not identified as EMI. The sensed cardiac event and associated event interval, e.g., RRI, may be used in an ongoing tachyarrhythmia detection algorithm. Control circuit 80 advances to block 112 to determine if EMI detection criteria are being met.

If the EMI event criteria are met at block 108, one or more sensed cardiac events may be identified as EMI events at block 110. In one example, the cardiac event sensed at block 104 is identified as an EMI event after the EMI event criteria are satisfied. In other examples, both the cardiac event sensed at block 104 and the most recent preceding sensed cardiac event are identified as EMI.

In response to identifying whether or not the sensed cardiac event as an EMI event at block 110, control circuit 80 determines if EMI detection criteria are met at block 112. Control circuit 80 may include a counter for counting the number of sensed events identified as EMI events out of a predetermined number of most recent sensed events in an X out of Y manner. If a threshold number of EMI events are identified out of the most recent Y sensed events, EMI may be detected at block 112. For example, if two out of eight most recent sensed events are identified as EMI events, EMI is detected at block 112. Other examples of EMI detection criteria may require at least two, at least three or another threshold number of consecutive EMI events. If EMI detection criteria are not met at block 112, EMI is not detected at block 114, and EMI monitoring continues by returning to block 102.

If EMI is detected at block 112, control circuit 80 withholds tachyarrhythmia detection at block 116. Tachyarrhythmia detection may be withheld until a threshold number of tachyarrhythmia detection intervals is reached and EMI is not being detected. In other examples, tachyarrhythmia detection may be withheld by not counting EMI events that are sensed at a tachyarrhythmia detection interval in a tachyarrhythmia detection interval count. Tachyarrhythmia detection (and subsequently tachyarrhythmia therapy) may be withheld by resetting tachyarrhythmia detection interval counters or setting a higher number of tachyarrhythmia detection intervals required to detect tachyarrhythmia at block 116. For example, the number of intervals required to detect VF may be set to 18 VF intervals out of 24 consecutive RRIs. When EMI is detected at block 112, the number of intervals required to detect VF may be increased from the programmed 18 out of 24 intervals to an adjusted number of intervals such as 30 out of 40, 36 out of 48 or 45 out of 60, for example. By increasing the number of intervals required to detect VT or VF in response to detecting EMI, tachyarrhythmia detection is withheld at block 116 when the programmed number of intervals to detect is reached to minimize inappropriate detection until additional evidence is acquired over a longer period of time, in this case additional VT or VF intervals.

In other examples, additional analyses of the cardiac electrical signal may be performed in order to detect tachyarrhythmia. For instance morphology analysis of the sensed events and/or the second cardiac electrical signal received by the second sensing channel 85 may be analyzed to determine if tachyarrhythmia detection criteria are met despite the detection of EMI.

Tachyarrhythmia therapy is withheld by withholding or delaying the tachyarrhythmia detection at block 116. In other examples, a tachyarrhythmia detection may be made, but if EMI is being detected at block 112 prior to therapy being delivered, the tachyarrhythmia therapy, such as ATP or a CV/DF shock may be withheld at block 116 until additional therapy delivery criteria are met. In some examples, charging of high voltage capacitors used to deliver a cardioversion or defibrillation shock pulse may be withheld if EMI is being detected at the time that other VT or VF detection criteria are satisfied.

Figure 7:
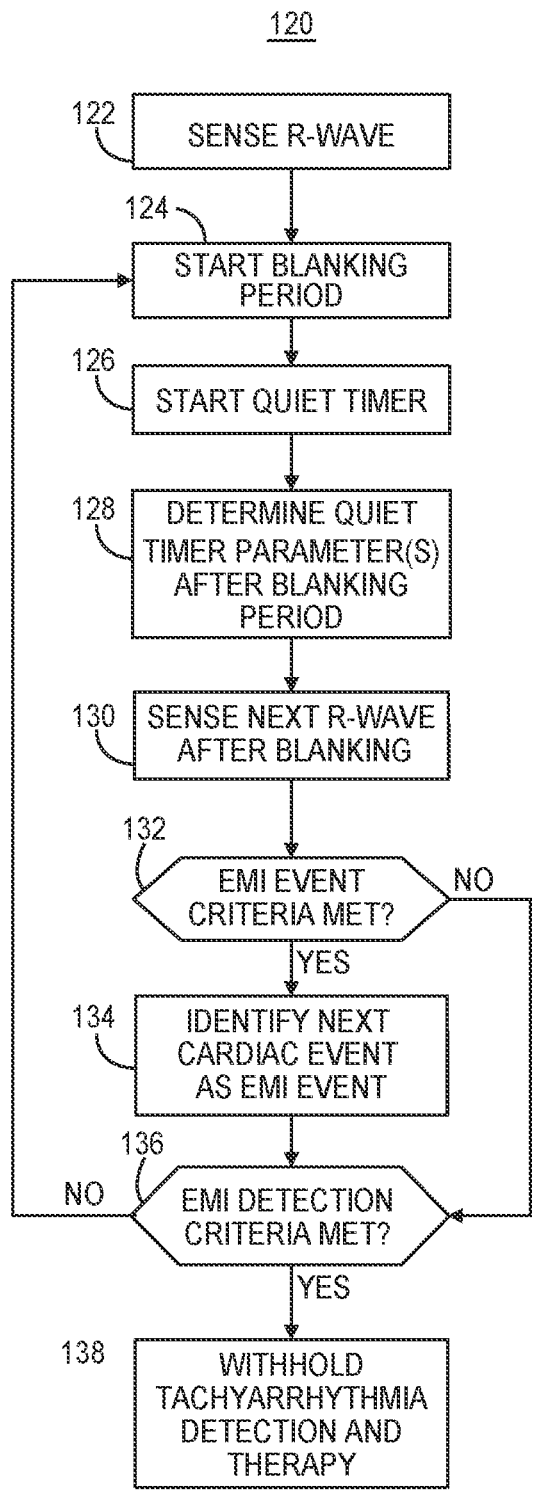
FIG. 7 is a flow chart of a method performed by an extra-cardiovascular ICD for detecting EMI for withholding tachyarrhythmia detection according to another example.

FIG. 7 is a flow chart 120 of a method for detecting EMI for withholding tachyarrhythmia detection according to another example. A cardiac event is sensed by sensing circuit 86 at block 122. The method of flow chart 120 may be performed following each sensed cardiac event so that each event may be identified as an EMI event if EMI event criteria are met on an event-by-event basis. In other examples, the process of flow chart 120 is performed only if the cardiac event sensed at block 122 occurs within a predetermined time interval since the most recent preceding sensed cardiac event or within a predetermined time interval of the expiration of a preceding post-sense blanking period. In still other examples, the method of flow chart 120 is performed only when a tachyarrhythmia detection interval counter has reached a threshold value. For example, the process of flow chart 120 may be performed when a VT detection interval counter, VF detection interval counter or combined VT and VF detection interval counter has reached a value of two, three or other predetermined threshold value.

The sensed cardiac event at block 122 may be an R-wave sensed by R-wave detector 66 of first sensing channel 83.

When the process of flow chart 120 is performed by extra-cardiovascular ICD 14, the sensing circuit 86 may pass an R-wave sensed event signal to control circuit 80 in response to the first cardiac electrical signal received by the first sensing channel 83 crossing an R-wave sensing threshold outside of a post-sense blanking period. In response to the R-wave sensed event signal, control circuit 80 controls sensing circuit 86 to start a post-sense blanking period at block 124.

The post-sense blanking period may be set to 100 to 150 ms in some examples. During the blanking period, sensing circuit 86 does not produce R-wave sensed event signals that are passed to control circuit 80. In other examples, R-wave sensed event signals may be produced but are ignored by control circuit 80 during the post-sense blanking period, at least for the purposes of detecting tachyarrhythmia. The post-sense blanking period may be set to prevent sensing of cardiac events during the physiological refractory period of the myocardium. For example, the post-sense blanking period may be set to avoid sensing an R-wave during the physiological refractory period of the ventricular myocardium since signals during that period are highly unlikely to be true R-waves and may be a T-wave or noise that might be falsely sensed as an R-wave. The post-sense blanking period may be set based on an expected R-T interval in some examples but may be less than an R-T interval and may be a fixed or adjustable blanking period. The post-sense blanking period may be set to be less than an expected fastest tachyarrhythmia interval, for example 200 ms or less.

At block 126, the quiet timer 81 of sensing circuit 86 is started in response to the R-wave sensed at block 122. As described above, the quiet timer 81 is started by being set to a quiet time interval. In this example, quiet timer 81 operates by being set to a quiet time interval in response to the cardiac electrical signal received by the first sensing channel 83 crossing the R-wave sensing threshold set by R-wave detector 86 under the control of control circuit 80.

The quiet timer 81 may be reset to the quiet time interval during (and after) the post-sense blanking period in response to each R-wave sensing threshold crossing that occurs before the quiet timer 81 has timed out. If the quiet timer 81 times out during the post-sense blanking period, the quiet timer 81 is not re-started during the post-sense blanking period in some examples since sensing of a cardiac event during the blanking period is inhibited. The quiet timer 81 is started upon the next sensed cardiac event that occurs outside the blanking period. In other examples, operation of quiet timer 81 may include restarting the quiet timer 81 if it has timed out during the post-sense blanking period and an R-wave sensing threshold crossing occurs during the post-sense blanking period even though a cardiac event is not sensed by sensing circuit 86.

As described below, the R-wave sensing threshold may be held at the amplitude at which the cardiac electrical signal crossed the R-wave sensing threshold for the duration of the post-sense blanking period started at block 124. The R-wave sensing threshold serves as a noise threshold for resetting the quiet timer 81 during the post-sense blanking period. At the expiration of the post-sense blanking period, the R-wave sensing threshold may be adjusted to a percentage of the maximum peak amplitude determined during the post-sense blanking period but not less than the minimum sensitivity setting (e.g., 0.15 mV).

In some examples, the R-wave sensing threshold is the noise threshold used to start and reset the quiet timer 81 at block 126. For example, R-wave detector 66 may sense an R-wave and determine a maximum peak amplitude during a subsequent peak tracking time interval. During a post-sense blanking period, the R-wave sensing threshold may be held at the amplitude at which the sensing threshold crossing occurred resulting in the sensed R-wave. At the end of the post-sense blanking period, R-wave detector 66 may adjust the R-wave sensing threshold from the amplitude held during the blanking period to a percentage of the maximum peak amplitude determined during the peak tracking time interval. For example, the R-wave sensing threshold may be adjusted to 25% to 90% of the maximum peak amplitude. In one example, the R-wave sensing threshold is adjusted to 53% of the maximum peak amplitude and the noise threshold is set equal to the R-wave sensing threshold during and after the post-sense blanking period. Alternatively, the noise threshold amplitude used to start and reset the quiet timer 81 may be set differently than the R-wave sensing threshold.

Control circuit 80 may be configured to detect EMI occurring at or above an EMI cut-off frequency by setting the quiet time interval at block 126 to be equal, or sometimes greater than, half of the EMI cut-off frequency cycle length. If the quiet timer 81 is configured to begin counting down from the quiet time interval immediately upon being started (decreased on the next sampling interval), EMI occurring at a frequency having a half cycle length that is equal to or less than the quiet time interval is detectable by control circuit 80.

However, if the quiet timer 81 is set to the quiet time interval and does not start counting down until the cardiac electrical signal falls below the noise threshold, the quiet time interval is effectively extended. As a result, the lowest EMI cut-off frequency detectable by control circuit 80 is lower than the frequency having a half cycle length equal to the quiet time interval. The EMI cut-off frequency will depend on both the quiet time interval and the noise threshold, as further described in conjunction with FIG. 16. The lower the noise threshold, the longer the cardiac signal is likely to remain above the noise threshold after crossing it. Thus, the lower the noise threshold, the longer the effective quiet time interval becomes, resulting in a lower EMI cut-off frequency. If the noise threshold is set to be the same as the R-wave sensing threshold, as a percentage of a maximum amplitude during the post-sense blanking period, as the percentage approaches 100%, the EMI cut-off frequency approaches the frequency having a half cycle length equal to the quiet time interval. As the percentage decreases, the EMI cut-off frequency is lowered. In some examples, the control circuit 80 may be configured to set or adjust the EMI cut-off frequency by setting or adjusting the noise threshold.

In one example, the quiet time interval that quiet timer 81 is set (and reset) to is 25 ms. If the quiet timer begins counting down immediately after being set to the quiet time interval, the cut-off frequency detectable by control circuit 80 is 20 Hz when the quiet time interval is 25 ms. When the quiet timer is held at the quiet time interval until the cardiac signal falls below the R-wave sensing threshold, however, the cut-off EMI frequency detectable by control circuit 80 will be dependent on both the quiet time interval and the percentage of the maximum peak amplitude used to set the R-wave sensing threshold, when used as the noise threshold. For instance, EMI occurring at a frequency of 10 Hz or more will likely cause the quiet timer 81 to be reset when the R-wave sensing threshold is adjusted to 53% of the maximum peak amplitude determined during the post-sense blanking period and the quiet time interval is 25 ms.

The theoretical cut-off frequency of EMI detectable by control circuit 80 may be computed assuming a sinusoidal noise signal for different noise thresholds. For a quiet time interval of 25 ms, if the R-wave sensing threshold is used as the noise threshold and set to 100% of the maximum amplitude during the post-sense blanking period, the cut-off frequency is 20 Hz (the quiet time interval equals half of the 20 Hz cycle length). If the percentage of the maximum amplitude used to set the R-wave sensing threshold is 95%, the theoretical cut-off frequency is reduced to approximately 16 Hz. The theoretical cut-off frequency is approximately 13 Hz for 85% of the maximum amplitude, approximately 10 Hz for 70% of the maximum amplitude, and approximately 7 Hz for 53%. In practice, the R-wave sensing threshold set to 53% of the maximum amplitude during the post-sense blanking period results in a cut-off frequency between 7 and 9 Hz. Some variation in the cut-off frequency may result when the quiet timer is held at the quiet time interval as long as the cardiac signal remains above the noise threshold. This variation is at least in part due to the signal being a digitally sampled signal.

EMI may occur at 16.7 Hz (the European rail frequency) and muscle noise may occur even lower. However, VF signals are generally less than 8 Hz. As the time interval 214 is increased for detecting lower frequency EMI, true ventricular fibrillation waves may cause the quiet timer 81 to be reset causing the next sensed R-wave to be identified as EMI when it is actually a shockable VF rhythm. Accordingly, the quiet time interval 214 and the noise threshold are optimally selected to detect EMI down to an EMI cut-off frequency while avoid identifying a true tachyarrhythmia cardiac event as EMI due to fibrillation waves causing quiet timer reset. For example, if the quiet timer 81 is controlled to begin counting down the quiet time interval immediately (e.g., the quiet timer is decremented on the next sample point after being set), the quiet time interval may be set to approximately 40 to 50 ms for an EMI cut-off frequency of approximately 10 to 12 Hz, which is above the expected frequency of VF. When the quiet timer 81 is held at the quiet time interval until the cardiac electrical signal falls below the noise threshold before starting to count down, the quiet time interval may be set at approximately 15 ms and the starting R-wave sensing threshold (used as the noise threshold) is set to 53% of the maximum peak amplitude detected during the previous post-sense blanking period to achieve an EMI cut-off frequency of approximately 12 Hz to separate the lowest detectable EMI frequency from the expected VF frequency.

The quiet timer operation at block 126 includes being reset to the quiet time interval in response to each R-wave sensing threshold crossing that occurs prior to expiration of the quiet time interval. If EMI is occurring within the quiet time interval, the quiet timer 81 will be reset. As described below in conjunction with FIGS. 8A and 8B, if the quiet timer 81 times out, a time out interrupt signal may be generated by sensing circuit 86 and used by control circuit 80 for determining a quiet timer parameter.

When the post-sense blanking period expires, the control circuit 80 may determine the quiet timer parameters at block 128 or wait until the next R-wave sensed event signal is received from sensing circuit 86. After the post-sense blanking period expires, sensing circuit 86 senses the next R-wave at block 130. The next R-wave is sensed in response to the earliest occurring R-wave sensing threshold crossing after expiration of the post-sense blanking period.

Control circuit 80 compares the quiet timer parameters to EMI event criteria at block 132 in response to receiving the next R-wave sensed event signal. The quiet timer parameters determined at block 128 indicate the behavior of the quiet timer 81 since the last sensed event (block 122). One quiet timer parameter determined at block 128 may be the status of the quiet timer 81 at the time that the next R-wave sensed event signal is received. The quiet timer status may be indicated by a quiet timer status register set to zero if the quiet timer is not actively running and set to a high value in response to the quiet timer 81 actively running at the time of the next R-wave sensed event signal. After determining the quiet timer status register value, the control circuit 80 may start or reset the quiet timer 81 to the quiet time interval at block 130 in response to the next R-wave sensed event signal.

Control circuit 80 may additionally or alternatively determine a quiet timer time out status at block 128. If the cardiac electrical signal does not cross the R-wave sensing threshold before the quiet time interval expires, the quiet timer 81 times out and sensing circuit 86 may generate an interrupt signal that causes control circuit 80 to set a quiet timer time out register to a high value. The quiet timer time out register value of one indicates that the quiet timer timed out since the last sensed event. A noise signal may have occurred but recurrent noise signals within the quiet time interval are not occurring and causing quiet timer reset, which indicates a relatively low probability of the next R-wave sensed event signal being an EMI event. As such, a quiet timer time out register value of 1 at the time that the next R-wave sensed event signal is received at block 130 is a contraindication of an EMI event. The quiet timer time out register may be reset to zero at the start of the next post-sense blanking period.

The quiet timer 81 may be reset one or more times before the next R-wave sensed event signal in response to R-wave sensing threshold crossings and in some cases may not time out before the next R-wave sensed event signal. If the quiet timer does not time out before the next R-wave sensed event signal, noise signals occurring at less than the quiet time interval may be causing the quiet timer 81 to be repeatedly reset. If a time out interrupt is not generated by sensing circuit 86, the control circuit 80 holds the quiet timer time out register at a value of zero. A zero value of the quiet timer time out register at the time the next R-wave sensed event signal is received at block 130 is a positive indicator of EMI.

Another example of a quiet timer parameter that may be determined at block 128 is a quiet timer ON time. The quiet timer ON time may be determined as the time, e.g., number of sampling intervals, from the time that the quiet timer is started until the quiet timer times out. If the quiet time interval is started once and not reset before timing out, the ON time is the quiet time interval. If the quiet time is reset one or more times before timing out, the ON time may be determined as the total number of sampling intervals or a total time interval for which the quiet timer 81 is running.

In some examples, the quiet timer 81 may time out and be enabled to be restarted during the post-sense blanking period in response to an R-wave sensing threshold crossing even though an R-wave sensed event signal is not produced. When the quiet timer 81 is allowed to be restarted during the post-sense blanking period, the combined time of two or more time periods that the quiet timer 81 is running may be determined at block 128. A quiet timer counter may be included in sensing circuit 86 or control circuit 80 that counts the number of sampling intervals that the quiet timer 81 is running. Control circuit 80 may read the value of the quiet timer counter at block 128 then reset the counter to zero for the start of the next post-sense blanking period. The value of the quiet timer counter may be held in a quiet timer ON time register in response to a quiet timer time out interrupt signal and read by control circuit 80 at the time of the next R-wave sensed event signal. As described below, the quiet timer counter and/or the quiet timer ON time register may be compared to an EMI threshold value for identifying the next R-wave sensed event signal as an EMI event.

Other examples of quiet timer parameters may be determined by control circuit 80 that are indications of the behavior of the quiet timer 81 since the last R-wave sensed event signal that is indicative of EMI. For example, the number of times the quiet timer 81 is reset may be counted. Control circuit 80 may determine one or more quiet timer parameters for comparison to EMI event criteria at block 132.

Control circuit 80 compares the quiet timer parameter(s) to EMI event criteria at block 132 to identify the next R-wave sensed at block 130 as an EMI event. In one example, if the quiet timer status register is "1", indicating that the quiet timer was active and running at the time of the next R-wave sensed event signal (sensed at block 130), the next R-wave sensed event signal is identified as an EMI event at block 134. In other examples, EMI event criteria applied at block 132 may require the quiet timer time out register be "0," indicating that the quiet timer 81 was started and did not time out since the most recent preceding R-wave sensed event signal due to repeated R-wave sensing threshold crossings at intervals shorter than the quiet time interval, causing the quiet timer 81 to be repeatedly reset. If the quiet timer 81 was started and did not time out, the R-wave sensed at block 130 may be identified as an EMI event at block 134.

In still other examples, the quiet timer ON time may be compared to an on time threshold at block 132. If the quiet timer ON time exceeds the on time threshold, the next R-wave sensed at block 130 may be identified as an EMI event at block 134. The ON time threshold applied to the quiet timer ON time register value may correspond to a percentage of the blanking period. For example, if the quiet timer ON time is at least 50% of the post-sense blanking period or all of the post-sense blanking period, the next R-wave sensed at block 130 after the blanking period expires may be identified as an EMI event at block 134. One or a combination of quiet timer parameters may be required to meet EMI event criteria at block 132 in order to identify the next sensed R-wave as an EMI event.

After determining whether or not the next cardiac event is an EMI event (block 132), control circuit 80 determines if EMI detection criteria are met at block 136. In some examples, a single EMI event identified at block 134 may cause EMI to be detected. In other examples, a threshold number of EMI events, consecutive or non-consecutive, may be required to detect EMI at block 136. For instance, control circuit 80 may increase an EMI event counter at block 134 in response to identifying the EMI event and compares the value of the EMI event counter to an EMI detection threshold at block 136. If at least X out of the most recent Y sensed R-waves are identified as EMI events, EMI is detected at block 136. In some cases, X and Y may be equal requiring the X EMI events to be consecutive. In other cases X may be less than Y requiring a threshold number of X EMI events within the most recent Y sensed events, but the X EMI events are not required to be consecutive.

Control circuit 80 is configured to withhold detection of VT or VF or at least withhold tachyarrhythmia therapy at block 168 in response to detecting EMI. Additional tachyarrhythmia detection criteria may be required to be met before detecting VT or VF and delivering a therapy. Tachyarrhythmia detection interval counters may be required to reach a number of intervals to detect tachyarrhythmia when EMI is not being detected in order to detect VT or VF. If EMI is being detected, tachyarrhythmia detector 92 may continue to monitor RRIs and detect VT or VF if EMI detection criteria are no longer met and other tachyarrhythmia detection criteria are being met.

Figure 8A:
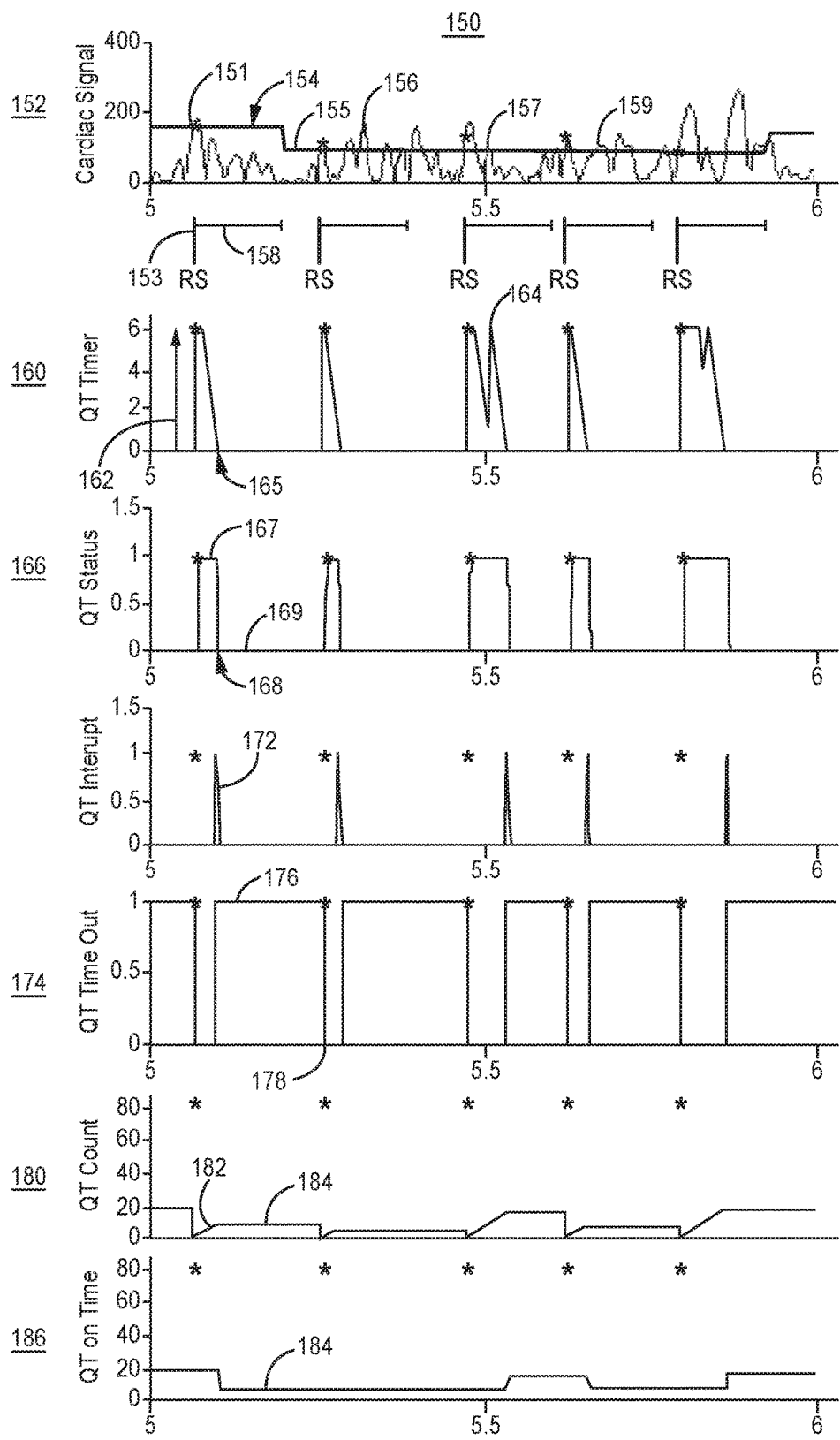
FIG. 8A is a timing diagram depicting the operation of a quiet timer and quiet timer parameter registers that may be included in an ICD for determining quiet timer parameters according to one example.

FIG. 8A is a timing diagram 150 depicting the operation of quiet timer 81 and quiet timer parameter registers that may be included in control circuit 80 for determining quiet timer parameters according to one example. From top to bottom, diagram 150 depicts a cardiac electrical signal 152, quiet timer activity 160 shown as a value of the interval that the quiet timer 81 is at over time, a quiet timer status register 166, quiet timer interrupt signal 172, a quiet timer time out register 174, a quiet timer counter 180, and a quiet timer ON time register 186. Filtered and rectified cardiac signal 152 is an example of a cardiac signal that may be produced by the first sensing channel 83 and passed to R-wave detector 66. In this example, the cardiac signal 152 is acquired during VF. The cardiac signal 152 crosses the R-wave sensing threshold 154 at 151, causing an R-wave sensed event signal 153 to be generated and passed from sensing circuit 86 to control circuit 80. In response to the R-wave sensed event signal 153, the quiet timer 81 is started by being set to a quiet time interval 162 and a post-sense blanking period 158 is started.

R-wave sensing threshold 154 is an auto-adjusting sensing threshold. It is held at the amplitude that cardiac signal 152 crosses at 151 until the post-sense blanking period 158 expires. During the blanking period 158, the R-wave sensing threshold 154 is a noise threshold used for resetting the quiet timer 81. Upon expiration of the post-sense blanking period 158, the R-wave sensing threshold 154 is adjusted to a percentage of the maximum peak amplitude of the cardiac signal 152 during the post-sense blanking period 158. The maximum peak may be the signal that was sensed, for example the maximum peak immediately following the threshold crossing at 151. At other times, the maximum peak amplitude may occur later in the post sense blanking period 158, such as peak 156. In the example shown, the R-wave sensing threshold 154 is adjusted upon expiration of the blanking period 158 to approximately 50% of the maximum peak amplitude determined during a peak amplitude tracking interval, which may be all or a portion of the post-sense blanking period 158. In one example, the maximum peak amplitude during the first 120 ms of the post-sense blanking period is determined and used for setting the starting R-wave sensing threshold at the expiration of the post-sense blanking period.

If the next R-wave sensed event occurs before the R-wave sensing threshold 154 drops from its starting value, the threshold during the next post-sense blanking period is held at the starting value. If the next R-wave sensed event occurs after the R-wave sensing threshold drops or decays from its starting value, the threshold during the next post-sense blanking period is held at whatever value the R-wave sensing threshold has been adjusted to, down to the programmed sensitivity which may be as low as 0.075 to 0.3 mV. When EMI is present, however, the R-wave sensed events are expected to occur early after the post-sense blanking period, while the R-wave sensing threshold is still at its starting value. As such, the noise threshold used during the post-sense blanking period in the presence of EMI is likely to be at or near the starting R-wave sensing threshold, e.g., 53% of the maximum amplitude detected during the immediately preceding post-sense blanking period.

The quiet timer 81 is set to the quiet time interval 162 upon each R-wave sensed event signal 153 and begins to count down sampling intervals (256 Hz in the example shown) or at a frequency that is some multiple of the clock signal produced by control circuit 80. If the cardiac signal 152 crosses the R-wave sensing threshold 154 before the quiet timer 81 times out, for example at threshold crossing 157, the quiet timer 81 is reset to the quiet time interval 162, e.g., at 164. If the quiet timer 81 times out, it is not reset during the post-sense blanking period 158 even if an R-wave sensing threshold crossing occurs, e.g., at 159. The quiet timer activity 160 is at 0 while the quite timer 81 remains "off" until it is restarted in response to the next R-wave sensing threshold crossing that occurs after the post-sense blanking period 158 expires.

In some examples, the quiet timer 81 does not start counting down the quiet time interval until the cardiac signal 152 falls below the R-wave sensing threshold 154. For instance at 163, the quiet timer activity 160 is observed to be set to the quiet time interval 162 and held at the quiet time interval 162 until the cardiac electrical signal 152 falls below the R-wave sensing threshold 154, at which point the quiet timer 81 begins to count down as observed by the decreasing quiet timer activity 160. When the quiet timer 81 is held at the quiet time interval 162 until the cardiac signal 152 falls below the R-wave sensing threshold (or noise threshold), the control circuit 80 may detect EMI occurring at a frequency having a half cycle length that is longer than the quiet time interval 162 since holding the quiet timer 81 at the quiet time interval 162 until the cardiac signal falls below the R-wave sensing threshold effectively extends the quiet time interval 162. In other examples, the quiet timer 81 may begin counting down a soon as it is set to the quiet time interval 162 in response to an R-wave sensed event. In this case, the control circuit is configured to detect EMI having a half cycle length that is equal to or less than the quiet time interval 162. In still another example, the quiet timer 81 may be set to the quiet time interval in response to the first negative-going threshold crossing following the R-wave sensed event and may immediately begin counting down the quiet time interval.

Control circuit 80 may set a quiet timer status register 166 to a high value 167 when the quiet timer 81 is running. If the quiet timer 81 times out, e.g., at 165, the quiet timer status register 166 is set to a low value 169. The value of the quiet timer status register at the time of the R-wave sensed event signal 153 may be determined as a quiet timer parameter for use in identifying sensed events as EMI events. If the quiet timer status register value is high when an R-wave is sensed, indicating the quiet timer 81 is running and has not timed out, the sensed R-wave may be identified as an EMI event. If the quiet timer status register value is low when an R-wave is sensed, indicating the quiet timer 81 is not active and has timed out, the sensed R-wave is not identified as an EMI event.

When the quiet timer 81 times out, e.g., at 165, the sensing circuit 86 may generate a quiet timer interrupt signal 172. Upon receipt of the interrupt signal 172, control circuit 80 may set a quiet timer time out register 174 to a high value 176. Upon the next R-wave sensed event signal, the quiet timer 81 is restarted and the quiet timer time out register value is cleared and reset to a low value 178 until the next quiet timer interrupt signal 172. In some examples, upon expiration of the post-sense blanking period 158 or upon receiving an R-wave sensed event signal 153, control circuit 80 may determine the value of the quiet timer time out register 174. If the value is high, the quiet timer 81 has timed out since the previous R-wave sensed event signal. The currently sensed event is not identified as an EMI event. If the value of the quiet timer time out register is low, a quiet timer interrupt signal 172 has not been generated since the last sensed event indicating that quiet timer 81 has been running and repeatedly reset since the last sensed event. In some examples, if the quiet timer time out register 174 is low at the time of receiving an R-wave sensed event signal 153, the sensed event signal is identified as an EMI event.

Control circuit 80 may include a quiet timer counter 180 that counts the sampling cycles that the quiet timer 81 is active or running. When the quiet timer 81 is started, the quiet timer counter 180 begins to count up as indicated by rising slope 182 and reaches a maximum count value 184 when the quiet timer 81 times out. Control circuit 80 may set a quiet timer ON time register to the maximum count value 184 in response to a quiet timer interrupt signal 172. The maximum count value 184 held by the quiet timer ON time register 186 indicates how long the quiet timer 81 was active before timing out.

Control circuit 80 may determine if the value of the quiet timer counter 180 and/or the quiet timer ON time register 186 is greater than a threshold value when the next R-wave sensed event signal 153 is received. If the value of the quiet timer counter 180 and/or the value of the quiet timer ON time register 186 is/are greater than a threshold value, e.g., equal to or greater than 40 when the sampling interval is 256 Hz which is equivalent to equal to or greater than 156 ms, then the next R-wave sensed event signal may be identified as an EMI event. If the quiet timer 81 does not time out due to the presence of sustained noise, the quiet timer ON time register 186 may not be set to the maximum count reached by the quiet timer counter 180 since no quiet timer time out interrupt signal is generated. As such, a logical OR may be used in comparing the value of the quiet timer counter 180 and the value of the quiet timer ON time register 186 to an EMI event threshold.

In various examples, control circuit 80 may determine the value of the quiet timer status register 166, the quiet timer time out register 174, the quiet timer counter 180 and/or the quiet timer ON time register 186 as quiet timer parameters for comparison to EMI event criteria at block 108 of FIG. 6 or block 132 of FIG. 7. In this example, where the cardiac signal 152 is a VF signal, the quiet timer status register 166 indicates the quiet timer 81 is inactive at the time of each sensed event (and similarly the quiet timer time out register 174 indicates that the quiet timer 81 has timed out prior to each sensed event). As such, EMI is not detected in this example, and VF detection is not withheld.

Figure 8B:
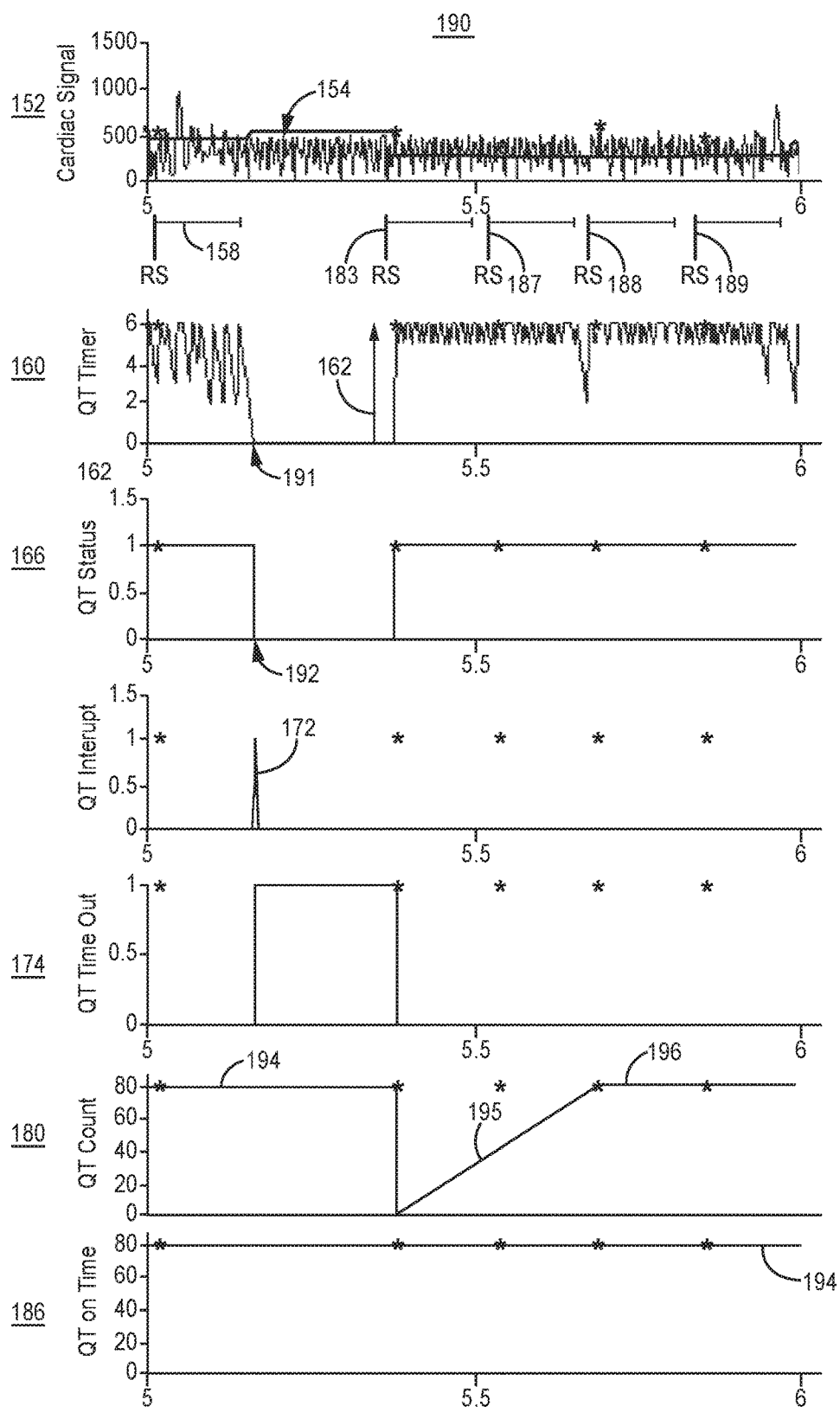
FIG. 8B is a timing diagram of another example of the behavior of a quiet timer and associated quiet timer parameters determined by an ICD.

FIG. 8B is a timing diagram 190 of another example of the behavior of quiet timer 81 and associated quiet timer parameters determined by control circuit 80. In this example, cardiac electrical signal 152 includes sustained EMI at 50 Hz during normal sinus rhythm (at approximately 60 beats per minute). As described above, R-wave sensed event signals 183, 187, 188 and 189 are produced by sensing circuit 86 in response to cardiac signal 152 crossing the R-wave sensing threshold 154 outside of the post-sense blanking period 158. The quiet timer 81 is set to quiet time interval 162 in response to the R-wave sensed event signal 183.

At time 191, the quiet timer 81 times out and the quiet timer status register 166 is cleared or set to a low value. A quiet timer interrupt signal 172 is generated, and the quiet timer time out register 174 is set high in response to the interrupt signal 172. The quiet timer counter 180 has reached a maximum count value 194 that is held by quiet timer quiet timer ON time register 186 in response to interrupt signal 172.

Upon the next R-wave sensed event signal 183, the control circuit 80 compares the quiet timer parameters to EMI event criteria. The quiet timer status 166 is low at the time the R-wave sensed event signal 183 is received, and the quiet timer time out register 174 is high. Based on these parameters, the R-wave sensed event signal 183 may not be identified as an EMI event. The values of the quiet timer counter 180 and the quiet timer ON time register 186, however, are both at maximum values 194 that may exceed an EMI event threshold. In some examples, the EMI event criteria may be satisfied based on the value of the quiet timer counter 180 and/or the quiet time ON time register 186. In other examples, the EMI event criteria may require that at least the quiet timer status register 166 is high or the quiet timer time out register 174 is low when the R-wave sensed event signal is received.

At the time of each of the subsequent R-wave sensed event signals 187, 188 and 189, the quiet timer status register 166 is set to a high value due to repeated resetting of the quiet timer in response to R-wave sensing threshold crossings of the cardiac signal 152 prior to expiration of the quiet time interval 162. Since the quiet timer 81 is repeatedly reset, no time out interrupt signals are generated, and the quiet timer time out register 174 remains set to a low value. Based on the high value of the quiet timer status register 166 or the low value of the quiet timer time out register 174 at the time each of the subsequent R-wave sensed event signals 187, 188 and 189 are received, each of the R-wave sensed event signals 187, 188 and 189 may be identified as EMI events. Identification of the EMI events may appropriately lead to EMI detection and withholding of an inappropriate VT or VF detection in this scenario of normal sinus rhythm in the presence of EMI.

Additionally or alternatively, the EMI event criteria may require that the quiet timer counter 180 or the quiet timer ON time register 186 meet or exceed a threshold value. In the example shown, the quiet timer counter 180 begins counting up from the time of R-wave sensed event signal 183 as indicated by slope 195 and reaches a maximum count value 196. The quiet timer ON time register 186 is not reset to the value of the quiet timer counter 180 after R-wave sensed event signal 183 because no quiet timer interrupt signals are generated. However, the R-wave sensed event signals may be identified as EMI events based on the quiet timer counter value at the time of each of the R-wave sensed event signals 187, 188 and 189.

FIG. 9 is a schematic diagram 200 of the operation of the quiet timer 81 and quiet timer behavior parameters that may be determined by control circuit 80 according to another example. From top to bottom, diagram 200 depicts a cardiac electrical signal 202, the quiet timer activity 212 shown as a value of the interval that the quiet timer is at over time, a quiet timer status register 222, a quiet timer time out register 232, and a quiet timer counter 242. The cardiac electrical signal 202 is a filtered and rectified signal that includes EMI noise. An R-wave sensed event signal 205 is generated upon a crossing 204 of an auto-adjusted R-wave sensing threshold 206 by cardiac electrical signal 202. In response to R-wave sensed event signal 205, control circuit 80 starts a post-sense blanking period 208. The R-wave sensing threshold 206 may be held at the amplitude at which the sensing threshold crossing 204 occurred (e.g., as described above in conjunction with FIG. 8A) or adjusted to a predetermined percentage, e.g., 53%, of the maximum peak amplitude 203 of the sensed event. During the blanking period 208, noise signals cross the R-wave sensing threshold 206 multiple times, but the next R-wave sensed event signal 209 is not produced by sensing circuit 86 until the next R-wave sensing threshold crossing 207 that occurs outside the post-sense blanking period 208.

In this example, control circuit 80 controls the sensing circuit 86 to operate the quiet timer 81 only during the post-sense blanking period 208. The quiet timer activity 212 is at zero, i.e., inactive, until the first R-wave sensing threshold crossing during post-sense blanking period 208. The first R-wave sensing threshold crossing during the post-sense blanking period 208 causes the quiet timer 81 to be started at 215 as indicated by the quiet timer activity 212 being set to a quiet time interval 214. The quiet timer 81 is started at 215 by being set to the starting time interval 214 and begins to count down from the starting time interval 214 (as indicated by negative slope of quiet time activity 212). In response to each crossing of the R-wave sensing threshold 206 by cardiac electrical signal 202 during the post-sense blanking period 208, quiet timer 81 is reset to the quiet time interval 214 and then begins counting down again.

In other examples, a noise threshold may be set during the post-sense blanking period 208 that is different than the R-wave sensing threshold 206. The noise threshold may be set to a percentage of the amplitude at R-wave sensing threshold crossing 204, a percentage of the maximum peak amplitude 203 of the sensed event, or other predetermined noise threshold value.

Since the cardiac electrical signal 202 repeatedly crosses the R-wave sensing threshold 206 at time intervals shorter than the quiet time interval 214, the quiet timer 81 is repeatedly reset to the quiet time interval 214 and does not time out to zero during the blanking period 208. Upon expiration of the blanking period 208, the quiet timer 81 may be terminated at 216 so that the quiet timer activity 212 returns to zero.

The quiet timer status register 222 is set high at 224 in response to the quiet timer 81 being started at 215. The quiet timer status register 222 may be held at the high value until control circuit 80 reads the value status register 222 after expiration of the post-sense blanking period 208. In the example shown, the status register 222 holds the high value until the next R-wave sensed event signal 209. At the time of the next R-wave sensed event signal 209, control circuit 80 fetches the value of status register 222 and resets the register 222 to zero at the beginning of the next post-sense blanking period 210, started in response to the next R-wave sensed event signal 209. As such, if the quiet timer is active (started) during the post-sense blanking period 208, the quiet timer status register value is set and held at "1" until read by control circuit 80, even if the quiet timer 81 times out prior to the expiration of the blanking period 208.

The quiet timer time out register 232 is set high if the quiet timer 81 times out during the post-sense blanking period 208. In the example shown, the quiet timer 81 does not time out during blanking period 208, as observed by the quiet timer activity 212 not returning to zero until the blanking period 208 expires at 216. As such, a time out interrupt signal is not produced by quiet timer 81. The time out register 232 remains low, at a value of "0," throughout the blanking period 208. In response to the next R-wave sensed event signal 209, control circuit 80 fetches the value of the time out register 222 at 234, which is held at zero. If the time out register 232 had been set high, the register would be reset to zero after fetching the value of the register 222 for the start of the next post-sense blanking period 210.

The quiet timer counter 242 starts counting the number of sampling intervals at 244 that the quiet timer 81 is actively running (as indicated by the positive slope) and stops counting if the quiet timer 81 times out or, as in the example shown, is terminated and reset to zero in response to the post-sense blanking period 208 expiring at 246. The value 248 reached at time 246 by quiet timer counter 242 is held until control circuit 80 fetches the value 248 of quiet timer counter 242 at time 250, in response to the next R-wave sensed event 209. In some examples, the value reached by quiet timer counter 242 may be latched to a quiet timer ON time register (not shown in FIG. 9) in response to a time out interrupt signal.

Control circuit 80 determines the quiet timer parameters by fetching the values of the quiet timer status register 222, the quiet timer time out register 232, and the quiet timer counter 242 in response to receiving the next R-wave sensed event signal 209. Control circuit 80 resets each of the registers 222 and 232 and 242 and starts the next post-sense blanking period 210. Control circuit 80 compares the quiet timer parameters to EMI event criteria for determining if R-wave sensed event signal 209 is an EMI event. The R-wave sensed event signal 209 may be identified as an EMI event in response to the quiet timer status register value being "1." In other examples, R-wave sensed event signal 209 may be identified as an EMI event in response to the quiet timer status register being "1" and/or the time out register being "0." In still other examples, R-wave sensed event signal 209 may be identified as an EMI event if the ON time counter value 248 is greater than a predetermined percentage (or all) of the post-sense blanking period 208.

Control circuit 80 enables quiet timer 81 to operate during the next post-sense blanking period 210 following the next R-wave sensed event signal 209 produced in response to the next R-wave sensing threshold crossing 207 after post-sense blanking period 208. The R-wave sensing threshold 206 is adjusted to a predetermined percentage, e.g., 50%, of the maximum peak amplitude of the sensed event, determined following the R-wave sensing threshold crossing 207. Quiet timer 81 is enabled to operate during the post-sense blanking period 210 and is started at 218 by being set to the quiet time interval 214 in response to the cardiac electrical signal 202 crossing the R-wave sensing threshold 206.

In this example, quiet timer 81 begins to count down the quiet time interval 214 immediately upon being set to the quiet time interval 214, as indicated by the downward slope of quiet timer activity 212. The cardiac electrical signal 202 does not cross the R-wave sensing threshold 206 again, and quiet timer 81 times out at 220. The quiet timer status register 222 is set high at 228 in response to the quiet timer 81 being started. As shown, the quiet timer status register 222 holds the high value until the control circuit 80 fetches the status value upon the next sensed event. A high value indicates the quiet timer 81 was started during the post-sense blanking period. In other examples, quiet timer status register 22 may be reset to low if the quiet timer 81 times out. In this case, the quiet timer time out status register 232 may be used to determine if the quiet timer 81 was active during the post-sense blanking period.

The quiet timer time out status register 232 is set high at 236 in response to a time out interrupt signal (not shown in FIG. 9) generated by sensing circuit 86 upon quiet timer 81 timing out at 220. The high value of the time out status register 232 may be held high until control circuit 80 fetches its value upon the next R-wave sensed event signal (not shown). A high value indicates the quiet timer was started during the post-sense blanking period but timed out.

The quiet timer counter 242 starts counting the number of clock cycles the quiet timer 81 is active starting from 252, when the quiet timer is started, until time 254, when the quiet timer 81 times out. The value 256 reached by the quiet timer counter 242 is held until fetched by control circuit 80 and reset to zero for the start of the subsequent post-sense blanking period. As described above, the value reached by the quiet timer counter 242 may be latched to a quiet timer ON time register (not shown in FIG. 9) in response to a time out interrupt signal when the quiet timer times out.

FIG. 10 is a flow chart 260 of a method for detecting EMI for withholding tachyarrhythmia detection according to another example. In this example, the quiet timer 81 is enabled to operate only during an EMI monitoring interval. The EMI monitoring interval may be a predetermined time interval, e.g., 100 ms, 200 ms, 500 ms, 1 second or other predetermined time interval. As shown in the example of FIG. 9, the EMI monitoring interval may be set equal to a post-sense blanking period. The EMI monitoring interval may be a fixed or variable interval that is set equal to or as a portion or percentage of a fixed or an adjustable blanking or refractory period or set to a portion of a most recently determined heart rate interval such as an RRI. In other examples, the EMI monitoring interval is a fixed interval that may be started and set independently of the timing of cardiac events.

The quiet timer is operated during the monitoring interval by starting the quiet timer in response to the cardiac electrical signal received by sensing circuit 86 crossing a noise threshold amplitude. In one example, the quiet timer is operated based on the same cardiac electrical signal from which the cardiac event was sensed at block 102. For example, first sensing channel 83 may sense an R-wave at block 102 from the first cardiac electrical signal received by first sensing channel 83, and the quiet timer 81 may be started in response to the first cardiac electrical signal crossing a noise threshold amplitude during the EMI monitoring interval. In other examples, the quiet timer 81 may be included in the second sensing channel 85 and may be started when the second cardiac electrical signal received by the second sensing channel crosses a noise threshold amplitude during the EMI monitoring interval.

In the example of FIG. 10, a cardiac event is sensed by sensing circuit 86 at block 262. The method of flow chart 260 may be performed on an event-by-event basis or performed only if the cardiac event sensed at block 262 occurs within a predetermined time interval since the most recent preceding sensed cardiac event or within a predetermined time interval of the expiration of a preceding post-sense blanking period. In still other examples, the method of flow chart 260 is performed only when a tachyarrhythmia detection interval counter has reached a threshold value.

The sensed cardiac event at block 262 may be an R-wave sensed by R-wave detector 66 of first sensing channel 83. When the process of flow chart 260 is performed by extra-cardiovascular ICD 14, the sensing circuit 86 may pass an R-wave sensed event signal to control circuit 80 in response to the cardiac electrical signal received by the first sensing channel 83 crossing an R-wave sensing threshold outside of a post-sense blanking period. In response to the R-wave sensed event signal, control circuit 80 controls sensing circuit 86 to start the post-sense blanking period at block 264 and enables quiet timer operation at block 266.

The post-sense blanking period may be set to be less than an expected fastest tachyarrhythmia interval, for example 200 ms or less. During the blanking period, sensing circuit 86 does not produce R-wave sensed event signals that are passed to control circuit 80 (or R-wave sensed event signals are ignored). As described in conjunction with FIG. 9, however, the quiet timer 81 may operate during the post-sense blanking period by being set to a quiet time interval in response to the cardiac electrical signal crossing a noise threshold amplitude. The noise threshold may be set to the value of the R-wave sensing threshold set by R-wave detector 86 under the control of control circuit 80. For example, the noise threshold may be set to the amplitude at which the cardiac electrical signal crossed the R-wave sensing threshold at block 262 as generally described in conjunction with FIG. 8A. Alternatively, as shown in FIG. 9, the noise threshold may be set to a percentage of the maximum peak amplitude of the sensed event.

As described above, control circuit 80 may be configured to detect EMI occurring at or above a desired frequency by setting the quiet time interval to be equal to or less than half of the desired EMI cut-off frequency cycle length when the quiet timer 81 is configured to start counting down the quiet time interval upon being set. A lower EMI cut-off frequency may be detected when the quiet timer 81 is held at the quiet time interval until the cardiac signal amplitude falls below the noise threshold. The quiet timer operation during the post-sense blanking period includes being reset to the quiet time interval in response to each noise threshold crossing that occurs before the quiet time interval expires. If EMI is occurring at a frequency having a half cycle length less than or equal to the EMI cut-off frequency, the quiet timer 81 will be started and may be repeatedly reset during the post-sense blanking period. As described above in conjunction with FIG. 9, if the quiet timer 81 times out during the post-sense blanking period, a time out interrupt signal may be generated by sensing circuit 86 and used by control circuit 80 for determining a quiet timer parameter.

When the post-sense blanking period expires, the quiet timer 81 may be "turned off" (disabled) and any remaining time interval may be terminated (or allowed to time out after the blanking period ends) without generating a time out interrupt signal. After the post-sense blanking period expires, sensing circuit 86 senses the next R-wave at block 268. The next R-wave is sensed in response to the earliest occurring R-wave sensing threshold crossing after expiration of the blanking period.

Control circuit 80 determines quiet timer parameters at block 270. The quiet timer parameters may be determined upon expiration of the post-sense blanking period. The quiet timer parameters may be determined upon expiration of the blanking period so that upon sensing the next R-wave, the next R-wave can be identified as an EMI event (or not). Alternatively the quiet timer parameters may not be determined until the next R-wave is sensed at block 158 and then used to identify the event as an EMI event or not.

The quiet timer parameters determined at block 270 indicate the behavior of the quiet timer 81 during the post-sense blanking period. One quiet timer parameter determined at block 270 may be the status of the quiet timer 81 during the blanking period. The quiet timer status may be indicated by a status register held at zero if the quiet timer is not started at all during the post-sense blanking period, indicating the quiet timer was inactive. The status register may be set and held at a high value in response to the quiet timer 81 being started during the post-sense blanking period. Once set high, the quiet timer status register may be held at the high value until the control circuit 80 retrieves the value at block 270 for determining quiet timer parameters. The control circuit 80 may then clear the quiet timer status register so that it has a zero value at the start of the next post-sense blanking period.

Control circuit 80 may additionally or alternatively determine if the quiet timer timed out during the post-sense blanking period at block 270. If the cardiac electrical signal does not cross the R-wave sensing threshold while the quiet timer 81 is running, i.e., before the quiet time interval expires, the quiet timer 81 times out upon expiration of the quiet time interval. The quiet timer 81 may generate an interrupt signal that causes control circuit 80 to set and hold the quiet timer time out register at a value of one. The quiet timer time out register value of one indicates that the quiet timer 81 timed out during the blanking period. A noise signal may have occurred but recurrent noise signals within the quiet time interval are not occurring during the blanking period, which indicates a relatively low probability of the next R-wave sensed event signal being an EMI event. As such, a quiet timer time out register value of 1 is a contraindication of an EMI event. The time out register may hold the value of "1" until read by the control circuit 80 at block 272. The quiet timer time out register may be reset to zero at the start of the next post-sense blanking period.

The quiet timer may be reset one or more times before the blanking period expires in response to noise threshold crossings and in some cases may not time out before the post-sense blanking period expires. If the quiet timer does not time out before the blanking period expires, a noise signal that may have caused the quiet timer 81 to be started causes a noise threshold crossing during the quiet time interval. If a time out interrupt is not generated by sensing circuit 86, the control circuit 80 holds the quiet timer time out register at a value of zero. A zero value is a positive indicator of EMI when the quiet timer status register is 1, indicating the quiet timer was started during the post-sense blanking period but did not time out.

Another example of a quiet timer parameter that may be determined at block 270 is a quiet timer ON time. The quiet timer ON time may be determined as the time, e.g., number of sampling intervals, from the time that the quiet timer 81 is started until the quiet timer times out (or is terminated at the expiration of the post-sense blanking period). If the quiet time interval is started once and not reset before timing out, the ON time is the quiet time interval. If the quiet time is reset one or more times before timing out, the ON time may be determined as the total number of sampling intervals for which the quiet timer 81 is running. In some examples, the quiet timer 81 may time out and be started a second time during the post-sense blanking period. The combined time of two or more intervals that the quiet timer 81 is running may be determined at block 270. The value of the quiet timer counter 242 (shown in FIG. 9) at the expiration of the post-sense blanking period may be determined by control circuit 80 as the ON time. Control circuit 80 may read the value of the quiet timer counter at block 270 then reset the counter to zero for the start of the next post-sense blanking period.

Other examples of quiet timer parameters that may be determined by control circuit 80 that are indications of the behavior of the quiet timer 81 during the blanking period indicative of EMI may include the number of times the quiet timer 81 is started (if allowed to be started more than once during the post-sense blanking period) and/or the number of times the quiet timer 81 is reset. Control circuit 80 may determine one or more quiet timer parameters for comparison to EMI event criteria at block 272.

Control circuit 80 compares the quiet timer parameter(s) to EMI event criteria at block 272 to determine if the next R-wave sensed at block 268 after the post-sense blanking period is likely an EMI event. In one example, if the quiet timer status is "1", indicating that the quiet timer 81 was started during the post-sense blanking period, the next R-wave (sensed at block 268) is identified as an EMI event at block 274. In other examples, EMI event criteria applied at block 272 may require the quiet timer status register be "1" and the quiet timer time out register be "0," indicating that the quiet timer 81 was started and did not time out during the blanking period due to repeated noise threshold crossings at intervals shorter than the quiet time interval, causing the quiet timer 81 to be repeatedly reset. If the quiet timer 81 was started and did not time out, the R-wave sensed at block 268 may be identified as an EMI event at block 274. If the quiet timer status is "1" but the time out register is "1", indicating the quiet timer was started during the post-sense blanking period but timed out, the next R-wave sensed at block 268 may not be identified as an EMI event.

In still other examples, the quiet timer ON time may be compared to an ON time threshold at block 272. If the quiet timer ON time exceeds the ON time threshold, the next R-wave sensed at block 268 may be identified as an EMI event at block 274. The ON time threshold applied to the quiet timer on time may correspond to a percentage of the blanking period. For example, if the quiet timer ON time is at least 20% of the post-sense blanking period, 30% of the post-sense blanking period, or other predetermined percentage of the post-sense blanking period, the next R-wave sensed at block 268 after the blanking period expires may be identified as an EMI event at block 274. One or a combination of quiet timer parameters may be required to meet EMI event criteria at block 272 in order to identify the next sensed cardiac event as an EMI event.

After determining whether the next sensed R-wave is identified as an EMI event, control circuit 80 determines if EMI detection criteria are met at block 276. In some examples, a single EMI event identified at block 264 may cause EMI to be detected. In other examples, a threshold number of EMI events, consecutive or non-consecutive may be required to detect EMI at block 276. As described above, control circuit 80 is configured to withhold detection of VT or VF and/or withhold tachyarrhythmia therapy at block 278 in response to detecting EMI. The process may return to block 264 to start the next post-sense blanking period and continue monitoring for EMI events. Control circuit 80 may monitor for EMI events by determining the quiet timer parameter(s) on an event-by-event basis. In other examples, as discussed above, control circuit 80 monitors for EMI events only when certain monitoring conditions are met.

In other examples, the EMI monitoring interval may be longer than the post-sense blanking period and one or more R-waves sensed during and/or after the EMI monitoring interval may be identified as EMI events based on quiet timer parameters determined from the behavior of the quiet timer during the EMI monitoring interval.

Figure 11:
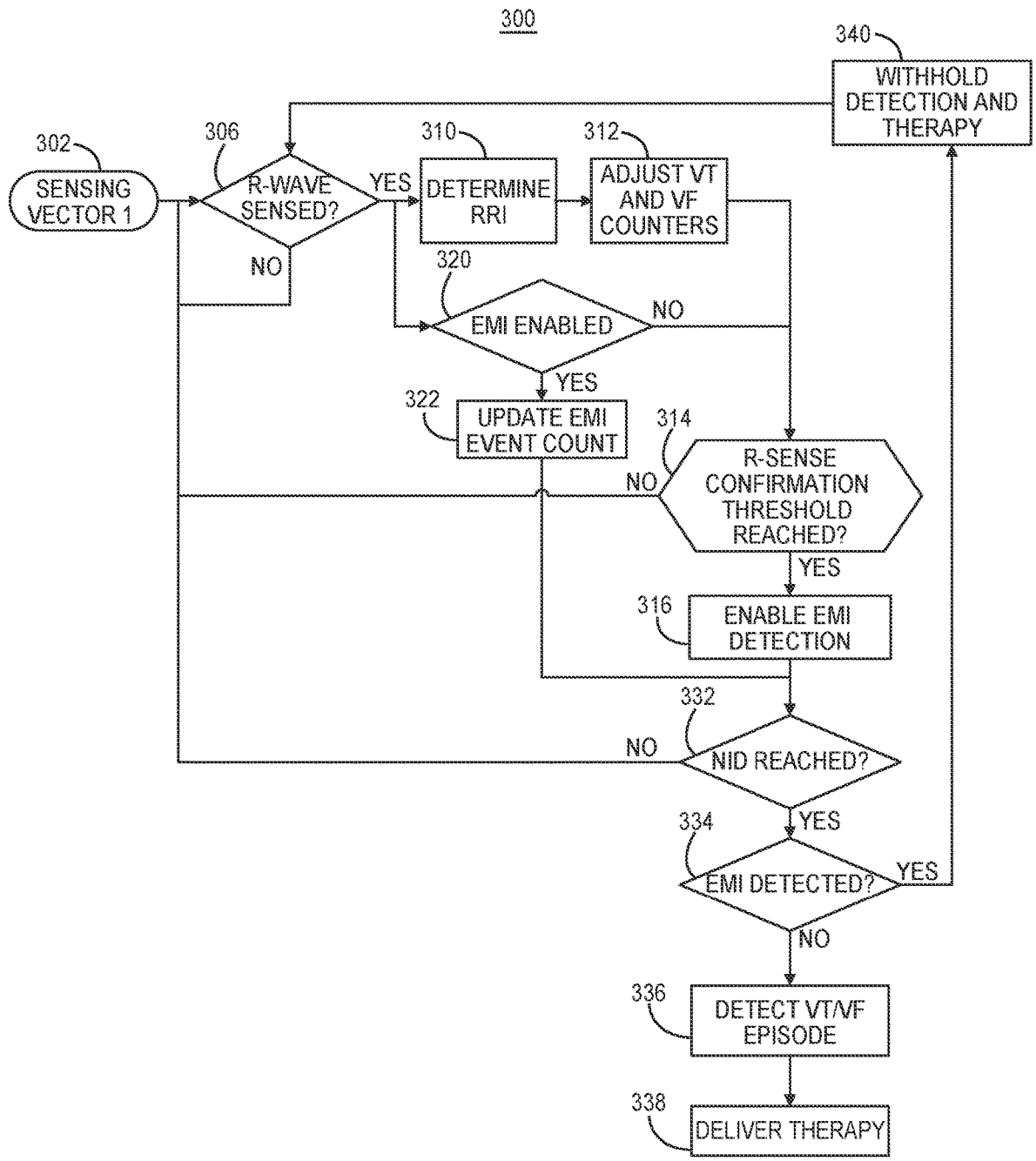
FIG. 11 is a flow chart of one method for controlling ventricular tachyarrhythmia detection and therapy using the EMI detection techniques disclosed herein.

FIG. 11 is a flow chart 300 of one method for controlling ventricular tachyarrhythmia detection and therapy using the EMI detection techniques disclosed herein. At block 302, a sensing electrode vector is selected by sensing circuit 86 for receiving a first cardiac electrical signal by first sensing channel 83. The first sensing vector selected at block 302 for obtaining a first cardiac electrical signal may be a relatively short bipole, e.g., between electrodes 28 and 30 or between electrodes 28 and 24 of lead 16 or other electrode combinations as described above. The first sensing vector may be a vertical sensing vector (with respect to an upright or standing position of the patient) or approximately aligned with the cardiac axis for maximizing the amplitude of R-waves in the first cardiac electrical signal for reliable R-wave sensing. In other examples, the first sensing vector may be a vector between one electrode 24, 26, 28 30 or 31 carried by the distal portion 25 of lead 16 and the ICD housing 15 (seen in FIG. 1A).

Sensing circuit 86 may produce an R-wave sensed event signal at block 306 in response to the first sensing channel 83 detecting an R-wave sensing threshold crossing by the first cardiac electrical signal outside of a blanking period. The R-wave sensed event signal may be passed to control circuit 80. In response to the R-wave sensed event signal, timing circuit 90 of control circuit 80 determines an RRI at block 310 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 312.

If the RRI is shorter than a tachycardia detection interval (TDI) but longer than a fibrillation detection interval (FDI), i.e., if the RRI is in a tachycardia detection interval zone, a VT interval counter is increased at block 312. If the VT interval counter is configured to count consecutive VT intervals for detecting VT, the VT interval counter may be reset to zero if the RRI is longer than the TDI. If the RRI is shorter than the FDI, the VF counter is increased. The VF counter may be a probabilistic VF counter that counts VF intervals in an X of Y interval such that VF may be detected when a threshold number of VF intervals are detected which are not required to be consecutive. In some examples, a combined VT/VF interval counter is increased if the RRI is less than the TDI.

After updating the tachyarrhythmia interval counters at block 312, tachyarrhythmia detector 92 compares the VT and VF interval counter values to an R-sense confirmation threshold at block 314. If a VT or VF detection interval counter has reached an R-sense confirmation threshold, "yes" branch of block 314, control circuit 80 enables EMI detection at block 316. In this example, the determination of quiet timer parameters may be performed on an event-by-event basis only after at least one of the VT or VF interval counter values has reached an R-sense confirmation threshold. In addition or alternatively to applying an R-sense confirmation threshold to the individual VT and VF counters, an R-sense confirmation threshold may be applied to a combined VT/VF interval counter. The R-sense confirmation threshold may be a value of one or more. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of intervals required to detect VT or VF.

If the R-sense confirmation threshold is not reached by any of the tachyarrhythmia interval counters at block 314, the control circuit 80 returns to block 306 and waits for the next R-wave sensed event signal. If the R-sense confirmation threshold is reached at block 314, the control circuit 80 enables EMI detection at block 316. EMI detection is enabled by determining quiet timer parameters in response to each R-wave sensed event signal for determining if the respective R-wave sensed event signal is an EMI event using the methods described above in conjunction with any of FIGS. 6 through 10. The quiet timer 81 may be operating on an event-by-event basis but quiet timer parameters may not be fetched by the control circuit 80 on an event-by-event basis for comparison to EMI event criteria as described in conjunction with the flow charts of FIGS. 6, 7 and 10. In other examples, the quiet timer 81 is not operating until the R-sense confirmation threshold is reached and EMI detection is enabled at block 316.

Before a tachyarrhythmia interval counter reaches a number of intervals to detect (NID) tachyarrhythmia ("no" branch of block 332), control circuit 80 responds to each R-wave sensed event signal at block 306 by determining the RRI at block 310 and by updating the EMI event count at block 322 after EMI detection is enabled ("yes" branch of block 320). The EMI event count is updated at block 322 by determining if EMI event criteria are met by the quiet timer parameters obtained since the preceding R-wave sensed event signal, e.g., as described in conjunction with FIGS. 7, 8A and 8B above or as described in conjunction with FIGS. 9 and 10 above. If EMI event criteria are met, for example if the quiet timer status register is "1," the time out register is "0," and/or the quiet timer counter value or quiet timer ON time register is equal to or greater than an EMI threshold, the currently sensed R-wave may be identified as an EMI event. The EMI event counter is updated at block 322. If EMI event criteria are not met, the R-wave sensed at block 306 is not identified as an EMI event, and the EMI event counter, which may be an X out Y counter, is updated accordingly.

After updating the EMI event count at block 322, control circuit determines if the NID is reached at block 332. In one example, the NID required to detect VT may be a count of 16 consecutive VT intervals, which are RRIs that fall into a predetermined VT interval range or zone. The NID to detect VF may be a count of 30 VF intervals out of the last 40 RRIs where the VF intervals are RRIs that fall into a predetermined VF interval range or zone. If an NID is reached, control circuit 80 checks if EMI is being detected at block 334 by comparing the updated EMI event count to EMI detection criteria. For example, if two out of the most recent eight R-wave sensed events are identified as EMI events, EMI is detected at block 334. Detection of VT or VF is withheld at block 340. No therapy is delivered. The process returns to block 306 to wait for the next sensed R-wave and continues determining RRIs for updating detection interval counters (block 312) and determining quiet timer parameters for identifying EMI events (block 322).

If an NID is reached at block 332 and EMI detection criteria are not satisfied at block 334, a VT or VF episode is detected at block 336. ATP and/or a shock therapy may be delivered at block 338 to terminate the detected tachyarrhythmia according to programmed therapy protocols.

Figure 12:
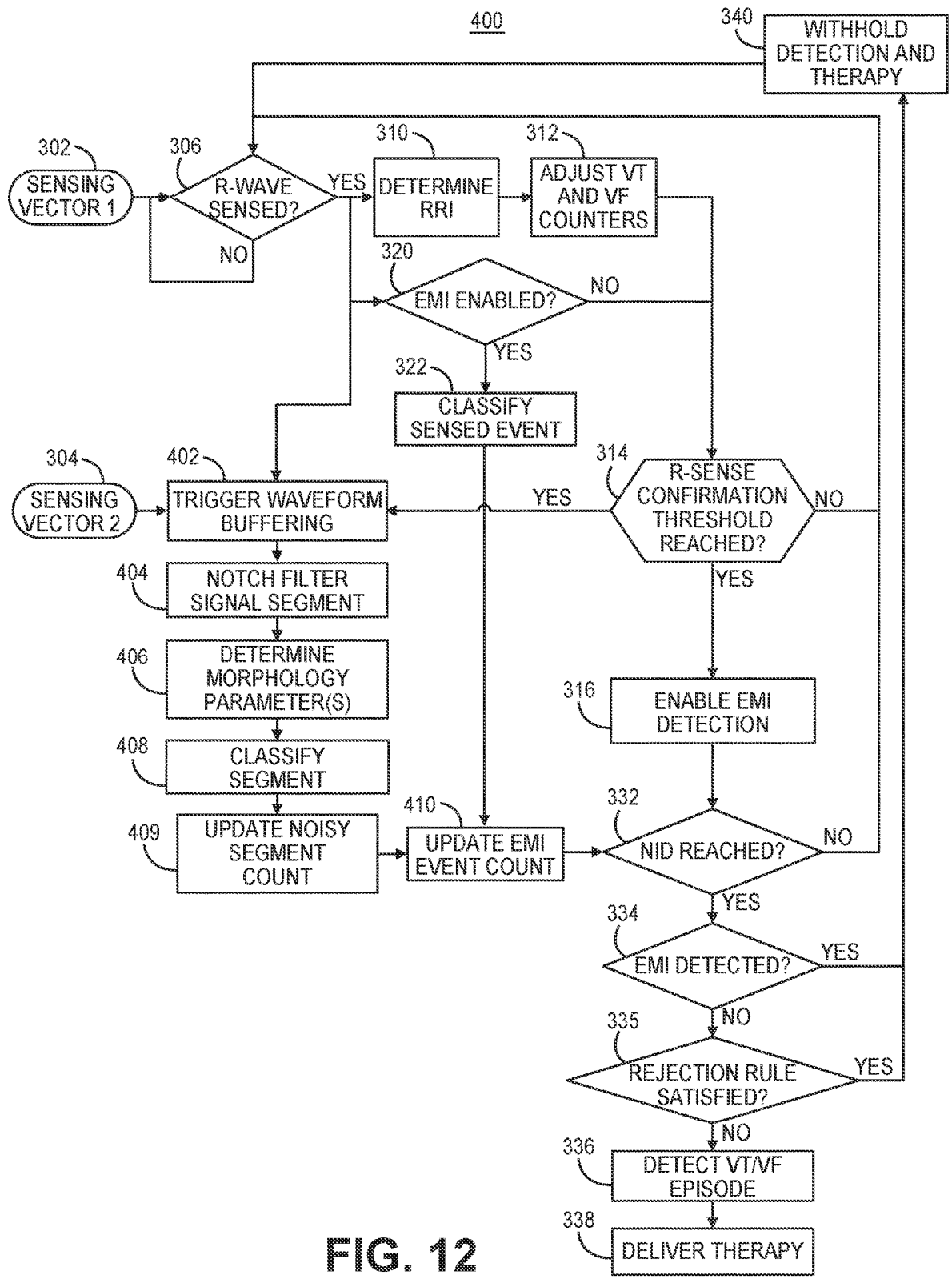
FIG. 12 is a flow chart of a method for detecting EMI and withholding tachyarrhythmia detection according to another example.

FIG. 12 is a flow chart 400 of a method for detecting EMI and withholding tachyarrhythmia detection according to another example. Operations performed in identically-numbered blocks in flow chart 400 of FIG. 12 may generally correspond to like-numbered blocks shown in FIG. 11 and described above. In the process of flow chart 400, the second sensing channel 85 is used to acquire a second cardiac electrical signal via a second sensing vector at block 304. At blocks 302 and 304, two different sensing electrode vectors are selected by sensing circuit 86 for receiving a first cardiac electrical signal by first sensing channel 83 and a second cardiac electrical signal by second sensing channel 85.

As described above, sensing circuit 86 may produce an R-wave sensed event signal at block 306 in response to the first sensing channel 83 detecting an R-wave sensing threshold crossing by the first cardiac electrical signal. The R-wave sensed event signal may be passed to control circuit 80 for determining the RRI (310), adjusting VT and VF detection interval counters (block 312), and determining if the sensed R-wave is an EMI event (block 322) when the R-sense confirmation threshold has been reached (block 314) and EMI detection has been enabled (block 316).

In addition to determining the RRI in response to the R-wave sensed event signal produced by the first sensing channel 83, control circuit 80 is triggered at block 402 to store a segment of the second cardiac electrical signal received from the second sensing channel 85 in a circulating buffer of memory 82 if the R-sense confirmation threshold has been reached at block 314. A digitized segment of the second cardiac electrical signal may be sampled over a time segment defined relative to the sample point time of the R-wave sensing threshold crossing and corresponding R-wave sensed event signal received from sensing circuit 86. The digitized segment may be 100 to 500 ms long, for instance. In one example, the buffered segment of the second cardiac electrical signal is at least 92 sample points obtained at a sampling rate of 256 Hz, or approximately 360 ms, of which 68 sample points may precede and include the sample point at which the R-wave sensed event signal was received and 24 sample points may extend after the sample point at which the R-wave sensed event signal was received. In other examples, the second cardiac electrical signal segment may be buffered at block 402 in response to each R-wave sensed event signal from the first sensing channel 83, but the segment may be discarded and not analyzed if the R-sense confirmation threshold is not reached by any of the interval counters at block 314.

If the R-sense confirmation threshold is reached at block 314, the control circuit 80 may apply a notch filter to the buffered, second cardiac electrical signal segment at block 404. The notch filter applied at block 404 may correspond to the filter described in the above-incorporated provisional U.S. Patent Application No. 62/367,166. The notch filtering performed at block 404 significantly attenuates 50-60 Hz electrical noise, muscle noise, other EMI, and other noise/artifacts in the stored, second cardiac electrical signal segment. Control circuit 80 may be configured to perform multiple analyses on the notch-filtered segment, to confirm the sensed R-wave or reject the sensed R-wave based on morphology analysis.

In one example, notch filtering performed at block 404 is implemented in firmware as a digital filter. The output of the digital notch filter may be determined by firmware implemented in the second sensing channel 85 according to the equation:

$$Y(n)=(x(n)+2x(n-2)+x(n-4))/4$$

where x(n) is the amplitude of the nth sample point of the digital signal received by the notch filter 76 (FIG. 5), x(n−2) is the amplitude of the n−2 sample point, and x(n−4) is the amplitude of the n−4 sample point for a sampling rate of 256 Hz. Y(n) is the amplitude of the nth sample point of the notch-filtered, digital second cardiac electrical signal. At a frequency of 60 Hz, the attenuation of the magnitude of Y(n) is −40 decibels (dB). At a frequency of 50 Hz, the attenuation is −20 dB, and at 23 Hz, which may be typical of an R-wave of the cardiac electrical signal, the attenuation is limited to −3 dB. Notch filtering at block 404 may therefore provide highly attenuated 50 and 60 Hz noise, muscle noise, other EMI, and other electrical noise/artifacts while passing lower frequency cardiac signals in the second cardiac electrical signal output of sensing channel 85.

The sample point numbers indicated in the equation above for determining a notch-filtered signal may be modified as needed when a different sampling rate other than 256 Hz is used, and the resulting frequency response may differ somewhat from the example given above. In other examples, other digital filters may be used for attenuation of 50 and 60 Hz. For example, for a sampling rate of 256 Hz, a filtered signal Y(n) may be determined as Y(n)=(x(n)+x(n−1)+x(n−2)+x(n−3))/4 which may have relatively less attenuation at 50 and 60 Hz but acts as a low-pass, notch filter with relatively greater attenuation at higher frequencies (greater than 60 Hz).

Analysis of the buffered signal segments may begin when the R-sense confirmation threshold is reached and may include any of the analyses disclosed in the above-incorporated U.S. Patent Application No. 62/367,166, U.S. Patent Application No. 62/367,170, U.S. Patent Application No. 62/367,221 and U.S. patent application Ser. No. 15/140,802 (Zhang, et al.). The morphology parameters may be determined for detecting noise, T-wave oversensing, and/or verifying R-wave morphology.

In one example, tachyarrhythmia detector 92 may determine one or more gross morphology parameters from the notch-filtered waveform segment at block 406. Gross morphology parameters may include, but are not limited to, a low slope content, a noise pulse count, a normalized rectified amplitude, a maximum signal width, or other noise metrics. Other examples of gross morphology parameters that may be determined are generally disclosed in U.S. Pat. No. 7,761,150 (Ghanem, et al.) and U.S. Pat. No. 8,437,842 (Zhang, et al.), both incorporated by reference in their entirety. The gross morphology parameters may be determined using the entire second cardiac signal segment stored at block 402 or a portion of the stored segment. In one example, at least 92 sample points, approximately 360 ms, are analyzed for determining the gross morphology parameters, which may be a portion of or the entire stored segment. The portion of the signal segment analyzed for determining gross morphology metrics extends beyond an expected QRS signal width so that at least a portion of the segment being analyzed corresponds to an expected baseline portion. In this way, at least one gross morphology parameter determined, such as the noise pulse, is correlated to non-cardiac signal noise that may be occurring during the baseline portion, such as non-cardiac myoelectric noise or EMI. Gross morphology parameters, therefore, may refer to parameters that represent the morphology of the analyzed portion of the cardiac signal segment as a whole and not limited to the morphology of the event sensed as an R-wave.

In one example, tachyarrhythmia detector 92 determines three morphology parameters at block 406 for classifying the second cardiac electrical signal segment as either a noisy segment or a potential shockable segment. The three morphology parameters may include a baseline noise parameter, an amplitude parameter, and a signal width parameter. The baseline noise parameter may be determined as a count of signal pulses during the notch-filtered second cardiac electrical signal segment. In one example, a first order differential signal is determined from the notch-filtered second cardiac electrical signal segment. In one example, the first order differential signal is determined using sample points over at least a 360 ms segment of the second cardiac electrical signal. The 360 ms segment may include sample points preceding and following the R-wave sensed event signal. The first order differential signal may be computed by computing successive differences, A(n)-A(n−1), between sample points, where n is the sample point number, ranging from 1 to 92 in the example given above, A(n) is the amplitude of the nth sample point and A(n−1) is the amplitude of the immediately preceding n−1 sample point.

Zero crossings of the first order differential signal are set by identifying consecutive sample points of the differential signal having opposite polarity. For example a positive sample point followed by a negative sample point is identified as a zero crossing, and a negative sample point followed by a positive sample point is identified as a zero crossing. Control circuit 80 compares the absolute values of the two signal sample points identified as a zero crossing. The sample point of the differential signal having the smaller absolute value amplitude is set to zero amplitude to clearly demark each zero crossing with two consecutive zero crossings defining a baseline noise pulse.

The differential signal with zero crossings set may be rectified and a noise pulse amplitude threshold may be determined from the rectified differential signal. For example, the noise pulse amplitude threshold may be determined based on the maximum amplitude of the rectified differential signal over the entire segment being analyzed, e.g., over 360 ms in the example given above. The noise pulse amplitude threshold may be set to a portion or percentage of the maximum amplitude. For instance, the noise pulse amplitude threshold may be set to be one-eighth of the maximum amplitude of the rectified differential signal in one example.

Signal pulses within the rectified, differential signal segment are identified and counted. If the sample point amplitude between two consecutive zero crossings crosses the noise pulse amplitude threshold, a signal pulse is counted. In some examples, a signal pulse is counted only when its pulse width is less than a threshold width, (e.g., less than six sample points). The control circuit 80 counts all pulses exceeding the noise pulse amplitude threshold in the segment. The signal pulse count value may be determined as the baseline noise parameter at block 406. Other techniques that may be implemented for determining a baseline noise parameter at block 406 are generally disclosed in U.S. Pat. No. 8,435,185 (Ghanem, et al.), incorporated herein by reference in its entirety.

An amplitude parameter may be determined at block 406 from the notch-filtered second cardiac electrical signal segment. Control circuit 80 determines the maximum absolute amplitude of the rectified, notch-filtered signal segment. The amplitudes of all sample points of the notch-filtered, rectified signal segment are summed and normalized by the maximum absolute amplitude. The normalized rectified amplitude (NRA) may be determined as four times the summed amplitudes divided by the maximum absolute amplitude. The higher this NRA, the more likely the second cardiac signal segment contains a valid R-wave of a VT or VF episode. The second cardiac signal segment may be classified as a potential shockable event that should be used in counting tachyarrhythmia detection intervals when the amplitude parameter is greater than a shockable amplitude threshold. If the second cardiac signal segment is classified is a potential shockable event based on the amplitude parameter, this classification may overrule an EMI event classification in some examples.

A signal width parameter may be determined at block 406 using the notch-filtered, rectified signal segment that is also used for determining the signal amplitude parameter. In other examples, however, the differential signal with set zero crossings used to determine the baseline noise parameter as described above may be used to determine the signal amplitude and signal width parameters instead of the notch-filtered, rectified signal segment. In order to determine the signal width parameter, control circuit 80 may first identify signal pulses in the signal segment having a peak amplitude that is greater than or equal to a pulse amplitude threshold.

A maximum signal width may then be determined from among these identified signal pulses.

The pulse amplitude threshold used to identify these signal pulses may be based on the maximum absolute amplitude of the notch-filtered, rectified signal segment. This pulse amplitude threshold may be a different threshold than the noise pulse amplitude threshold used for counting signal pulses for obtaining a baseline noise parameter. For example, the pulse amplitude threshold used for determining the signal width parameter may be set to half the maximum absolute amplitude of the rectified, notch-filtered signal segment whereas the noise pulse amplitude threshold used to determine a count of signal pulses may be set to one-eighth the maximum amplitude of the rectified, differential signal segment.

The maximum signal width may be determined only from signals reaching a peak amplitude criterion. For example, the maximum peak of each pulse is determined, and all pulses having a maximum peak that is greater than or equal to the pulse amplitude threshold, e.g., greater than half the maximum absolute amplitude, are identified. Of these identified signal pulses, the signal pulse having the greatest pulse width is identified. Tachyarrhythmia detector 92 may determine the signal width for the identified pulses as the number of sample points (or corresponding time interval) between a pair of consecutive zero crossings of the rectified, notch-filtered signal. This greatest pulse width is determined as the maximum pulse width of the second cardiac electrical signal segment and used as the signal width parameter for classifying the signal segment at block 408.

At block 408, tachyarrhythmia detector 92 fetches the gross morphology parameters for comparison to potential shockable beat criteria and to noise detection criteria. For example, the signal amplitude parameter, NRA in the example given above, may be compared to a potential shockable beat amplitude threshold. When the NRA is determined as described above, the potential shockable beat amplitude threshold may be set between 100 and 150, and to 140 in some examples. If the NRA is greater than the threshold, the signal segment is likely to include a true R-wave of a VT or VF episode and is therefore a potential shockable beat (if it is occurring at a VT or VF interval).

The pulse width parameter is compared to a potential shockable beat width threshold. In one example, the potential shockable beat width threshold is set to 20 sample points when the sampling rate is 256 Hz. If the NRA and the maximum pulse width for the signal segment are both greater than the respective amplitude and width thresholds, the segment is identified as a potential shockable beat. Both the amplitude parameter and the signal width parameter may be required to exceed a respective amplitude threshold and width threshold in order to identify the segment as a potential shockable beat. In other examples, only one of the amplitude parameter or the signal width parameter may be required to exceed its respective threshold in order to identify the segment as a potential shockable beat.

The baseline noise parameter is compared to a first noise threshold if the segment is identified as a potential shockable beat. For example, if the signal pulse count determined as the baseline noise parameter is greater than the first noise threshold, e.g., greater than 12, the second cardiac electrical signal segment is classified as a noisy segment at block 408. If the signal pulse count is less than the first noise segment threshold, the segment remains classified as a potential shockable beat at block 408.

If the segment is not identified as a potential shockable beat based on the signal amplitude and/or signal width parameters, the baseline noise parameter may be compared to a second noise threshold at block 408. The second noise threshold may be lower than the first noise threshold. If the segment is not identified as a potential shockable beat, less stringent criteria, e.g., a lower noise threshold, may be applied for classifying the segment as a noisy segment. In one example, the second noise threshold is six when the baseline noise parameter is determined as the signal pulse count as described above. If the baseline noise parameter meets or exceeds the second noise threshold, the second cardiac electrical signal segment is classified as a noisy segment at block 408. If the segment does not meet the potential shockable beat criteria or the noisy segment criteria, the segment may remain unclassified at block 408 in some instances.

Control circuit 80 updates a noisy segment count at block 409 to track the number of noisy segments that are identified out of a predetermined number of most recent buffered cardiac signal segments, e.g., out of the most recent eight cardiac signal segments. The number of segments identified as being noisy may be compared to a VT/VF detection rejection rule at block 335.

At block 410, control circuit 80 may update the EMI event count using both the morphology parameters of the second cardiac electrical signal determined at block 406 and the quiet timer parameter-based classification of the sensed event made at block 322. In some examples, if the second cardiac electrical signal segment meets potentially shockable beat criteria applied at block 408, the R-wave sensed event is not counted as an EMI event, even if the R-wave sensed event is identified as an EMI event at block 322 based on the quiet timer parameters. For instance, if the signal amplitude parameter of the second cardiac signal segment exceeds an amplitude threshold and the signal width parameter exceeds a width threshold, the second cardiac signal segment is classified as a potentially shockable segment at block 408. The R-wave sensed event is not counted as an EMI event at block 410. If the signal amplitude parameter and the signal width parameter do not meet or exceed their respective thresholds, R-wave sensed event is counted as an EMI event at block 410 if the quiet timer parameters meet EMI event criteria at block 322.

If the NID is reached at block 332, the value of the EMI counter is compared to an EMI detection threshold at block 334. For example if two out of the most recent eight sensed events are counted as EMI events, EMI is detected at block 334. The VT or VF detection is withheld at block 340. In order to detect VT or VF, the NID is required to be reached when EMI detection criteria are not satisfied. If VT or VF is detected, therapy is delivered at block 338.

In other examples, two different EMI event counts may be updated at block 410. One EMI event count may be updated taking into account the classification of potentially shockable beats of the second cardiac electrical signal segment at block 408 and the EMI event identification at block 322. A second EMI count may be updated based only on the classification of the sensed event at block 322 based on quiet timer parameters. Both EMI event count values may be required to equal or exceed an EMI detection threshold in order to withhold the VT or VF detection.

If EMI is not detected at block 334, tachyarrhythmia detector 92 may determine if other VT/VF detection rejection rules are satisfied at block 335 based on morphology analysis of the second cardiac electrical signal segments. For example, the noisy segment count updated at block 409 may be compared to count threshold value at block 335. If the number of noisy segments exceeds a threshold value, a gross morphology rejection rule is satisfied at block 335. The VT or VF detection is rejected and therapy is withheld at block 340. The methods for detecting EMI and withholding VT/VF detection and therapy as disclosed herein may be implemented in conjunction with other VT/VF detection rejection rules applied at block 335. Other VT/VF detection rejection rules are generally disclosed in the above-incorporated U.S. Patent Application No. 62/367,166, U.S. Patent Application No. 62/367,170, U.S. Patent Application No. 62/367,221 and U.S. patent application Ser. No. 15/140,802 (Zhang, et al.). Additional analyses may be performed for determining morphology parameters, comparing the parameters to rejection rules, which when satisfied cause the VT or VF detection based on the NID being reached to be withheld.

For example, additional analysis may include detecting R-waves from the second cardiac electrical signal segments during post-processing for confirming an R-wave sensed in real time from the first cardiac electrical signal and updating an R-wave confirmation rejection rule as generally disclosed in U.S. Patent Application 62/367,166. Briefly, an amplitude ratio of the maximum peak amplitude of the signal segment to the maximum peak amplitude of a most recent confirmed R-wave sensed event may be determined. The amplitude ratio is compared to a ratio threshold for confirming the R-wave sensed event that triggered storage of the current second cardiac signal segment. The amplitude ratio is determined, e.g., from a look up table of amplitude ratio values, based on the time interval from the most recent preceding confirmed R-wave sensed event to the maximum peak amplitude of the current signal segment. If the amplitude ratio exceeds the ratio threshold, the currently sensed R-wave is confirmed. If not, the currently sensed R-wave is not confirmed and a count of unconfirmed R-waves is updated for use in determining if an R-wave confirmation rejection rule is satisfied at block 335. If satisfied, at least a portion of the R-waves sensed from the first cardiac electrical signal that led to an NID being reached are not confirmed and the VT/VF detection may be withheld.

Other analysis performed at block 335 may include determining a morphology matching score for updating a beat morphology rejection rule, determining T-wave oversensing parameter for updating a T-wave oversensing rejection rule, and determining other noise parameters for updating a noise rejection rule, all described in the above-incorporated pending applications. Briefly, the morphology matching score may be determined by performing wavelet transform or other morphology matching analysis on a portion of the stored segment to determine if the stored second cardiac electrical signal segment includes a waveform that matches a sinus R-wave and is therefore unlikely a VT or VF beat. The beat morphology rejection rule may be satisfied at block 335 when a minimum number of morphology match scores out of a predetermined number of most recent morphology match scores exceed a match score threshold. A relatively high match score, exceeding a selected match score threshold, indicates the unknown beat matches the known R-wave template and is therefore a normal R-wave.

In some examples, TWOS parameters may be determined from a first order differential signal 69 received from first sensing channel 83. Alternatively or additionally, the second cardiac electrical signal from sensing channel 85, before or after notch filtering, may be used for determining TWOS parameters for detecting TWOS based on morphology analysis of the stored second cardiac electrical signal segments. Techniques generally disclosed in U.S. Pat. Application No. 62/367,221 may be used for determining T-wave oversensing parameters and updating a TWOS rejection rule at block 335 when a threshold number of R-wave sensed events are determined to be TWOS.

Other noise parameters may be determined using the second cardiac electrical signal segments by analyzing peak amplitudes of a group of the signal segments as generally disclosed in U.S. Patent Application No. 62/367,170. A noise rejection rule may be updated at block 335 and if satisfied by a threshold number of noise detections made based on the signal segment amplitude analysis, a VT/VF detection may be withheld at block 340. As such, the EMI detection criteria applied at block 334 for rejecting the NID-based VT or VF detection may be one of multiple VT/VF detection rejection criteria applied by tachyarrhythmia detector 92 for rejecting the NID-based VT or VF detection.

Figure 13:
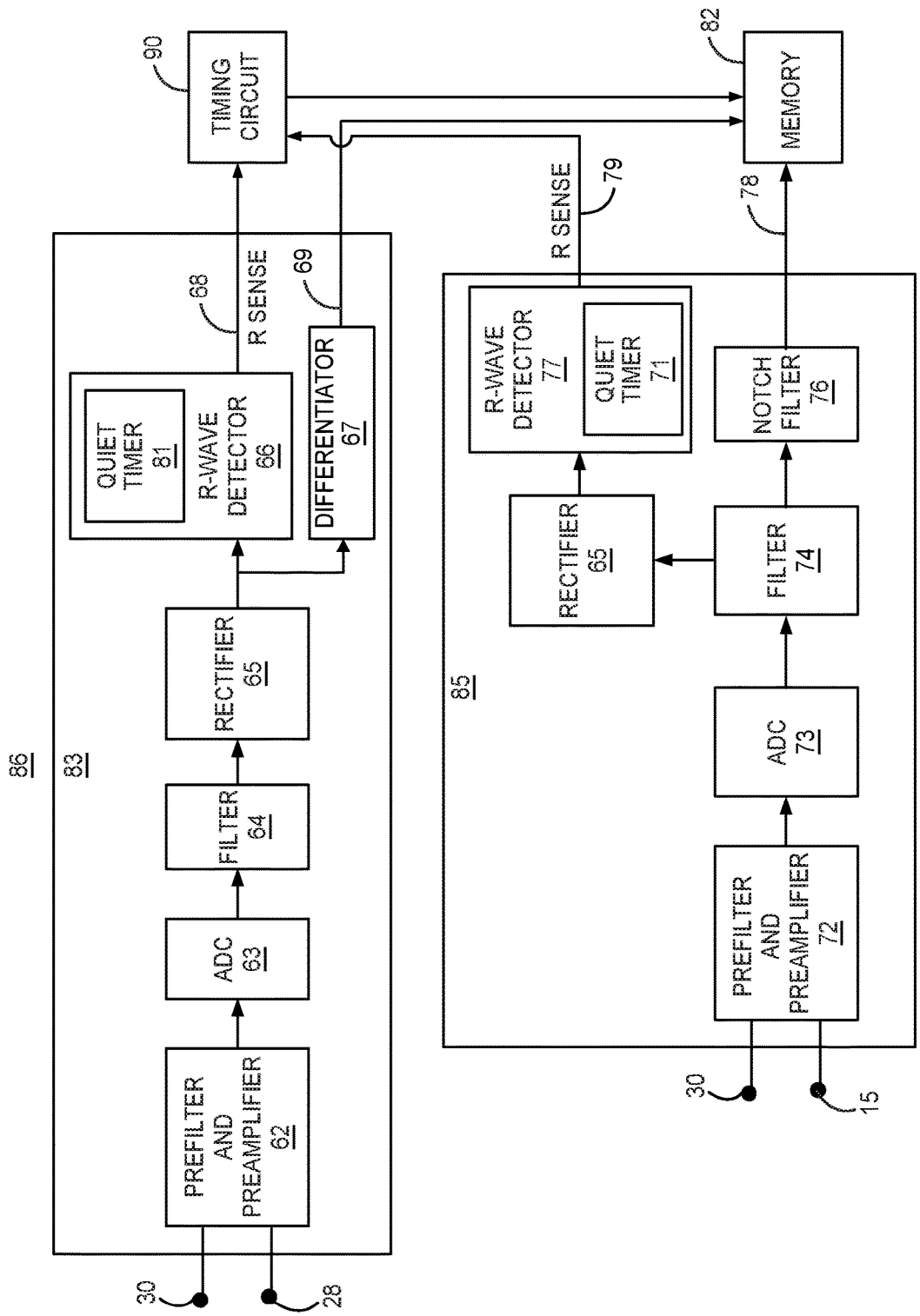
FIG. 13 is a diagram of circuitry included in the sensing circuit of FIG. 4 according to another example.

FIG. 13 is a diagram of circuitry included in the sensing circuit 86 of FIG. 4 according to another example. In FIG. 13, identically-numbered components of sensing channels 83 and 85 correspond to like-numbered components described in conjunction with and shown in FIG. 5. In the example of FIG. 5, first sensing channel 83 is configured to sense R-waves by R-wave detector 66 in real time and produce R-wave sensed event signals 68 that are passed to timing circuit 90 as the R-waves are sensed. Second sensing channel 85 is configured to pass the filtered, digitized output signal 78 to memory 82 for storage of second cardiac electrical signal segments as triggered by R-wave sensed event signals 68 from first sensing channel 83 without performing real-time R-wave sensing from the second cardiac electrical signal.

In the example of FIG. 13, second sensing channel 85 is configured to pass the digitized filtered output signal 78 to memory 82 for storage of second cardiac electrical signal segments as described above. Sensing channel 85 is additionally configured to perform real-time R-wave sensing from the second cardiac electrical signal. In this case, second sensing channel 85 includes rectifier 75 for rectifying the digitized and bandpass filtered signal output of filter 74. The rectified signal is passed from rectifier 75 to R-wave detector 77. R-wave detector 77 may include a sense amplifier, comparator or other R-wave detection circuitry configured to apply an auto-adjusting R-wave sensing threshold to the rectified signal for sensing an R-wave in response to a positive-going R-wave sensing threshold crossing.

Second sensing channel 85 may produce R-wave sensed event signals 79 that are passed to timing circuit 90 in real time for use in determining RRIs based on the second cardiac electrical signal. RRIs may be determined as the time interval or sample point count between consecutively received R-wave sensed event signals 79. Timing circuit 90 may pass RRIs determined from R-wave sensed event signals 79 from second sensing channel 85 to tachyarrhythmia detector 92 for use in updating second VT and VF interval counters based on RRIs determined from real-time sensing of R-waves by the second sensing channel 85.

Second sensing channel R-wave detector 77 may include a quiet timer 71 that operates during a predetermined EMI monitoring interval, e.g., a post-sense blanking period. Quiet timer 71 may operate in the same manner as quiet timer 81 of sensing channel 83 and may be configured to operate according to any of the techniques described above in conjunction with FIGS. 6 through 10. Quiet timer parameters may be determined by control circuit 80 that represent the behavior of the quiet timer 81 since a preceding sensed R-wave for identifying a currently sensed R-wave as an EMI event. Control circuit 80 may be configured to detect EMI based on quiet timer parameters determined from the activity of either one or both of the quiet timers 71 and 81.

Figure 14:
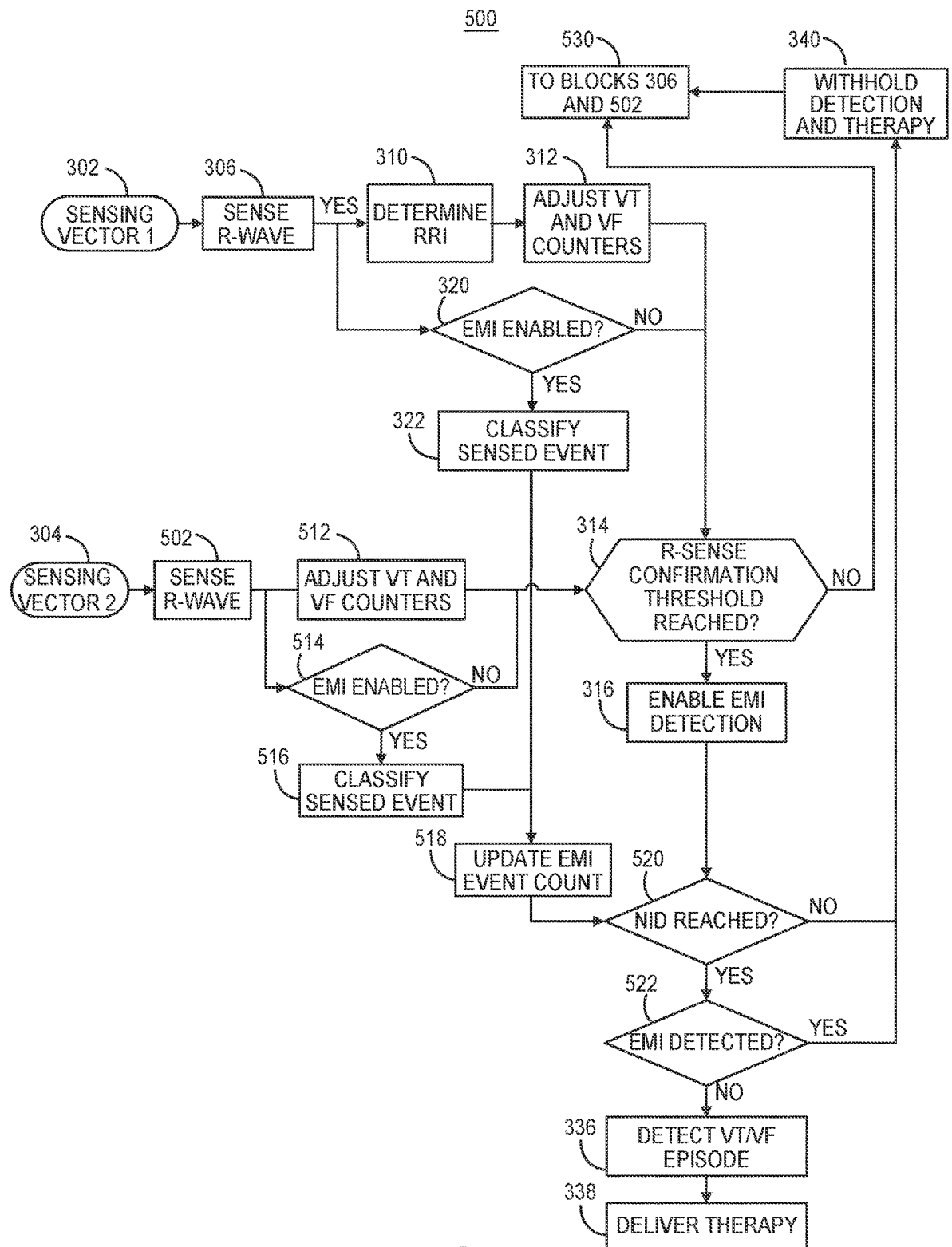
FIG. 14 is a flow chart for detecting EMI for withholding tachyarrhythmia detection according to another example.

FIG. 14 is a flow chart 500 for detecting EMI for withholding tachyarrhythmia detection according to another example that includes detection of EMI in both first and second cardiac electrical signals received by ICD 14. Identically-numbered blocks in FIG. 14 may generally correspond to like-numbered blocks in FIG. 12. When an R-wave is sensed (block 306) from the first sensing vector 302 by the first sensing channel 83, the RRI is determined (block 310) for updating VT and VF detection interval counters (block 312). If EMI detection is enabled (block 320) based on an R-sense confirmation threshold being reached (block 314) by the VT and VF detection interval counters, the sensed R-wave is classified as an EMI event (or not) based on quiet timer parameters using the techniques described above.

R-waves are not sensed by the second sensing channel 85 in real time in the example of FIG. 12. In flow chart 500 of FIG. 14, R-waves may be sensed from the second sensing vector 304 in real time by the second sensing channel 85, when R-wave detector 77 is included in the second sensing channel 85 as shown in FIG. 13. The second sensing channel 85 is configured to sense R-waves from the second cardiac electrical signal received via the second sensing vector 304, and, as such, tachyarrhythmia detector 92 may update second VT and VF detection interval counters at block 512 based on real-time sensing of an R-wave at block 502.

At block 314, control circuit 80 determines if the R-sense confirmation threshold is reached. The R-sense confirmation threshold may be compared to the first and/or second VT and VF detection interval counters updated at respective blocks 312 and 512. If the R-wave sensing confirmation threshold is not reached by any of the VT or VF detection interval counters, ICD 14 returns to block 306 and block 502 to continue R-wave sensing as indicated at block 530. ICD 14 may continue sensing R-waves on each sensing channel 83 and 85, respectively, without comparing quiet timer parameters to EMI event criteria for detecting EMI events.

In some examples, if at least one VT or VF detection interval counter reaches the R-sense confirmation threshold at block 314, EMI detection is enabled for the respective channel or for both channels 83 and 85. For instance, if one of the first or second VT detection interval counters reaches a value of two or one of the first or second VF detection interval counters reaches a value of three, EMI detection is enabled at block 316 for both sensing channels 83 and 85. In other examples, EMI detection may be enabled for only the respective first sensing channel 83 or second sensing channel 85 having a detection interval counter that reaches the R-sense confirmation threshold. After enabling EMI detection at block 316, ICD 14 returns to blocks 306 and 502 (as indicated at block 530) to sense the next R-waves by each respective sensing channels 83 and 85.

When EMI detection is enabled for the second sensing channel 85 (as determined at block 514), control circuit 80 is configured to obtain quiet timer parameters in response to an R-wave sensed event signal. As described above with respect to quiet timer 81 in conjunction with FIGS. 6 though 10, the quiet timer parameters may represent the behavior of the quiet timer 71 since a preceding R-wave sensed event or during the most recent post-sense blanking period that expired before the current R-wave sensed event signal. The quiet timer parameters may be determined from a quiet timer status register, a quiet timer time out register indicating whether quiet timer 71 timed out, a quiet timer counter and/or a quiet timer ON time register as described above. The R-wave sensed at block 502 is identified as an EMI event at block 516 if quiet timer parameters meet EMI event criteria, e.g., according to any of the examples described above. Otherwise the R-wave sensed event remains classified as a non-EMI sensed event.

After enabling EMI event detection, the EMI event count is updated at block 518. Separate EMI event counters may be provided in control circuit 80 for separately counting each of the sensed events identified as EMI for the first and second sensing channels 83 and 85. In other examples, a single EMI event counter may be provided and is increased if an R-wave sensed event is identified as an EMI event in at least one sensing channel 83 or 85. In another example, a single EMI event counter may be provided but is only increased if an R-wave sensed by the first sensing channel 83 is identified as an EMI event and the R-wave sensed event by the second sensing channel 85 is also identified as an EMI event. It is recognized that in some instances, one sensing channel 83 or 85 may not sense an R-wave when the other sensing channel does. In this case, the sensed event may still be identified as an EMI event if EMI event criteria are satisfied and be used for updating the EMI event count accordingly.

At block 520, the tachyarrhythmia detector 92 compares the values of the VT and VF detection interval counters to respective NIDs. In some examples, the NID is reached when one VT or VF detection interval counter for one sensing channel 83 or 85 reaches its respective NID. In other examples, the VT or VF NID is reached at block 520 only when the VT or VF detection interval counter for both channels 83 and 85 reach the respective VT or VF NID.

If the NID is reached for at least one or both sensing channels as required by NID criteria, the control circuit 80 determines if EMI detection criteria are satisfied at block 522. If a single EMI event counter is provided to count events identified as EMI events, the EMI event counter value is compared to the EMI detection threshold. If two separate EMI event counters are updated at block 518 for the respective two sensing channels 83 and 85, each EMI event counter value may be compared to an EMI detection threshold. In some cases, both EMI event counter values are required to reach an EMI detection threshold, for example 2 EMI events out of 8 most recent sensed events. In other examples, EMI is detected at block 522 if at least one of the two separate EMI event counter values reaches the EMI detection threshold.

If EMI is detected at block 522, the VT or VF detection is withheld at block 340. ICD 14 continues to sense R-waves and update the VT and VF detection interval counters and EMI event count by returning to blocks 306 and 502 (as indicated by block 530). If EMI is not detected, tachyarrhythmia detector 92 detects VT or VF at block 336 and delivers the appropriate therapy at block 338.

Figure 15:
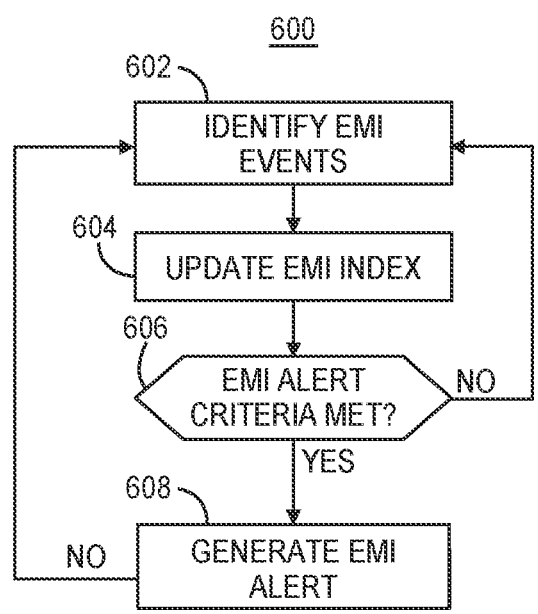
FIG. 15 is a flow chart of a method that may be performed by an extra-cardiovascular ICD for determining an EMI index and generating an EMI alert.

FIG. 15 is a flow chart 600 of a method that may be performed by ICD 14 for determining an EMI index and generating an EMI alert. ICD 14 identifies cardiac sensed events as EMI events using the methods described herein at block 602. In response to identifying an EMI event, an EMI index is updated at block 604. The EMI index may be an EMI event count determined over an EMI observation period.

In one example, the EMI events are identified at block 602 based on the quiet timer status parameter for the purposes of updating the EMI index at block 604. For instance, if the quiet timer status register is 1 at the time of an event is sensed, the event is identified as an EMI event for use in updating the EMI index at block 604. In other examples, additional quiet timer parameters may be used for identifying EMI events at block 602, such as the quiet timer time out register, quiet timer counter, and/or the quiet timer ON time register value. The quiet timer parameter criteria for identifying EMI events at block 602 for the purpose of updating an EMI index may be the same or different criteria than the EMI event criteria used to identify EMI events for detecting EMI and withholding a tachyarrhythmia detection as described in conjunction with FIGS. 6 through 10.

The EMI observation period may be a few seconds, one minute, one hour, one day, one week or other predetermined time period. The EMI index may be updated by increasing an EMI event count for each EMI event identified over the EMI observation period. The EMI index may be stored for each observation period and a trend of the EMI index over time may be stored in memory 82 for review by a clinician.

The EMI index may be compared to alert criteria at block 606. The EMI index may be compared to the alert criteria each time it is updated or at the end of the observation period. If the alert criteria are satisfied, the control circuit 80 may generate an EMI alert at block 608. In one example, a patient alert is generated at block 608, e.g., by controlling patient alert circuit 94 to generate a buzzing sensation, audible tone or other alert signal perceivable by the patient. Additionally or alternatively, a control circuit 80 generates a clinician alert for transmission by telemetry circuit 88 to an external device, e.g., via the CARELINK® system, Medtronic, Inc., Minneapolis Minn.

In some examples updating the EMI index at block 604 includes updating a patient alert EMI index and updating a clinician alert EMI index. Each of these indices may be updated over different observation periods and different EMI alert criteria may be applied to each index for generating a patient alert and for generating a clinician alert respectively. For example, the patient alert EMI index may be an EMI event count obtained over a predetermined number of sensed cardiac events, e.g., over 10 sensed cardiac events, or predetermined number of seconds, e.g., five seconds, 10 seconds, or more. Alert criteria for generating a patient alert may be a threshold number of cardiac sensed events identified as EMI events, e.g., if six cardiac sensed events are identified as EMI events during the observation period, e.g., within 10 sensed cardiac events, the patient alert may be generated at block 608. The patient may be instructed to react to the alert by moving away from an EMI environment in response to the alert.

In some examples, the observation period may be an adjustable period. For example, after generating a patient alert the observation period for updating the EMI index may be increased to avoid repetitive patient alerts within a short interval of time, allowing the patient to react to the alert, e.g., by moving away from the EMI environment. After generating the first patient EMI alert at block 608, ICD 14 continues to identify EMI events at block 602 and update the patient alert EMI index at block 604, however the observation period may be lengthened, e.g., from 10 cardiac sensed events or 10 seconds to 30 cardiac sensed events or 30 seconds or more to extend the time between patient alerts.

The clinician alert observation period may be longer than the patient alert observation period. For example, the clinician alert observation period may be over one day, one week or more. The EMI index may be compared to clinician alert criteria at block 606 for alerting the clinician that the patient has had significant EMI exposure. The clinician may react to the alert by instructing the patient to take precautionary measures to avoid or reduce EMI exposure. The clinician EMI alert criteria may require a percentage of sensed cardiac events being identified as EMI events over the observation period. For example, if 20% of sensed cardiac events are identified as EMI events over a 24-hour period, a clinician EMI alert may be generated. In other examples, the clinician EMI alert criteria may require an increasing trend in the EMI index. For example, the EMI index may be required to increase from one observation to the next by a predetermined percentage, e.g., 20%, 50% or other percentage.

In some examples, control circuit 80 may be configured to update both a patient EMI index and a clinician EMI index at block 604, but generate only one of the patient EMI alert or the clinician EMI alert. For example, the patient EMI alert may be generated in response to patient EMI alert criteria being met by the patient EMI index, but the clinician EMI index and associated trends may be stored in memory 82 for transmission to an external device via telemetry circuit 88 the next time ICD 14 is interrogated. Alternatively, the patient EMI index and associated trends may be updated and stored in memory 82 without generating a patient alert, and the clinician EMI index may be used to determine if an EMI alert should be generated at block 608. In still other examples, one or more EMI indices may be updated at block 604, and EMI index data may be stored in memory 82 without generating EMI alerts. The EMI index data is available for review by a clinician upon retrieval from ICD 14 via telemetry circuit 88.

Figure 16:
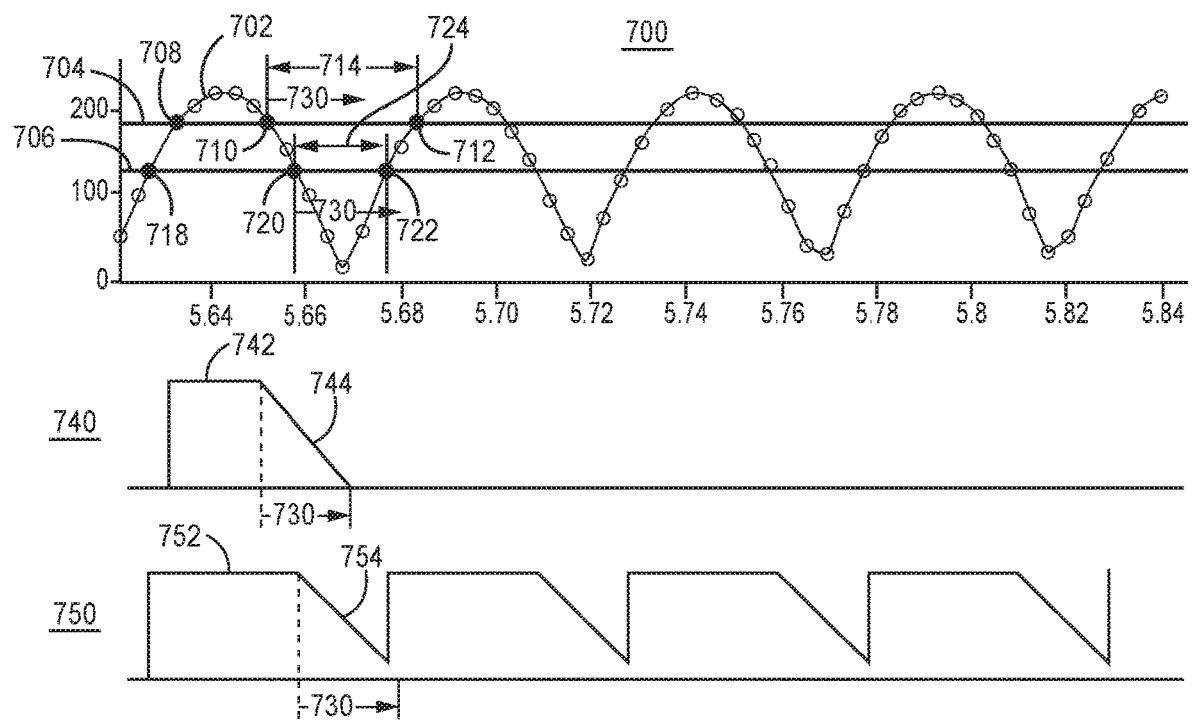
FIG. 16 is a diagram depicting a sinusoidal noise waveform and the behavior of a quiet timer under two different noise threshold conditions.

FIG. 16 is a diagram 700 depicting a rectified 10 Hz sinusoidal noise waveform 702 and the behavior of a quiet timer 81 under two different noise threshold conditions. The rectified 10 Hz waveform is an example of an EMI signal that may be present in the cardiac electrical signal received by sensing module 86. Quiet timer activity 740 shows the behavior of quiet timer 81 when the noise threshold 704 is set to approximately 75% of a maximum peak amplitude determined during the preceding post-sense blanking period (not shown). The quiet timer 81 is started when the noise waveform 702 crosses threshold 704 at point 708, as observed by quiet timer activity 740. It is assumed that noise threshold crossing at point 708 occurs outside a post-sense blanking period and is therefore a sensed event that starts the quiet timer 81. During the preceding blanking period (not shown), started in response to sensing an earlier threshold crossing by the cardiac electrical signal including noise waveform 702, the maximum peak amplitude of the cardiac electrical signal used to set the noise threshold 704 may be the maximum of 10 Hz noise signal 702 falsely sensed as an R-wave.

In response to the noise threshold crossing at point 708, the quiet timer 81 is set to and held at the quiet time interval 730 (as indicated by flat portion 742 of quiet timer activity 740) until the noise waveform 702 falls below the noise threshold 704 at point 710. The quiet timer 81 begins to count down the quiet time interval 730, as indicated by decreasing slope 744 of quiet timer activity 740, and times out prior to the noise waveform 702 reaching the noise threshold 704 at point 712 during the next half-cycle of the rectified noise waveform 702. In this example, the quiet timer 81 may be set to a quiet time interval 730 of 25 ms. This quiet time interval 730 is shorter than the portion 714 of the 10 Hz waveform 702 over which the noise waveform 702 changes from the negative-going threshold crossing 710 to the positive-going threshold crossing 712. In this example, the 10 Hz noise waveform 702 may not be detected when the noise threshold 704 is set to approximately 75% of the maximum peak amplitude When the noise threshold 706 is adjusted to approximately 50% of the maximum peak amplitude determined during the preceding post-sense blanking period, the behavior of the quiet timer 81 is represented by quiet timer activity 750. The quiet timer 81 is started when the noise waveform 702 crosses the noise threshold 706 at point 718. The quiet timer 81 is set to and held at the quiet time interval 730 (as indicated by flat portion 752) until the noise waveform 702 falls below the noise threshold 706 at point 720. The quiet timer 81 begins counting down the quiet time interval 730 as indicated by the decreasing slope 754 of quiet timer activity 750. Just prior to timing out, the noise waveform 702 crosses the noise threshold 706 at point 722, causing the quiet timer 81 to be reset to the quiet time interval. The portion 724 of noise waveform 702 between negative-going threshold crossing 720 and the next positive-going threshold crossing 722 is equal to or less than the quiet time interval of 25 ms, causing quiet timer reset. In this example, the 10 Hz noise waveform 702 is likely detected by control module 80 based on quiet timer behavior parameter(s) as described above when the noise threshold 706 is set to approximately 50% of the maximum peak amplitude. The portion 730 of the waveform 702 is approximately one-fourth of the 10 Hz cycle length or 25 ms. As such, if the quiet time interval 730 is 25 ms, the 10 Hz noise signal is detected as noise when the noise threshold is set to approximately 50% of the maximum peak amplitude of the cardiac electrical signal but is not detected as noise when the noise threshold is set to approximately 75% of the maximum peak amplitude.

Figure 17:
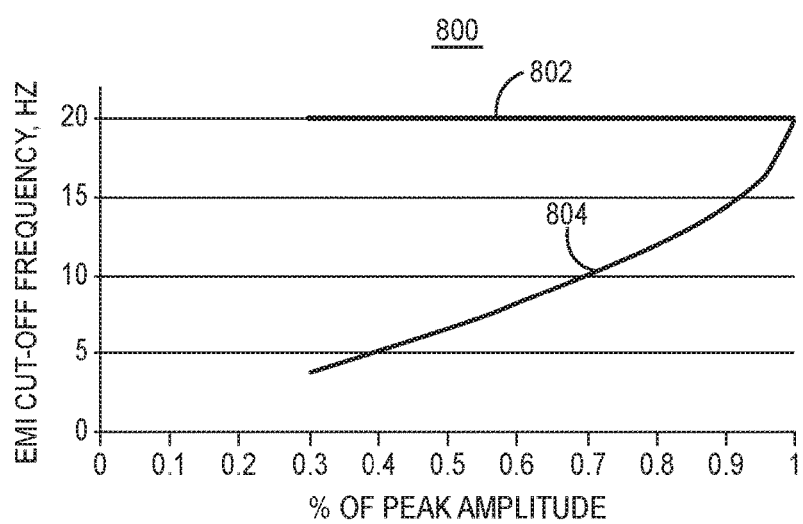
FIG. 17 is a graph of the estimated lower EMI cut-off frequency for a given quiet time interval.

FIG. 17 is a graph 800 of the estimated lower EMI cut-off frequency (y-axis) detectable by control module 80 as a function of the percentage (x-axis) of the maximum peak amplitude used to set the R-wave sensing threshold used as the noise threshold. The plot 800 of the estimated EMI cut-off frequencies is for a quiet time interval of 25 ms. If the quiet timer 81 begins counting down immediately, the EMI cut-off frequency is 20 Hz (802). If the quiet timer 81 does not begin counting down until the cardiac electrical signal falls below the noise threshold, as shown in FIG. 16, the estimated EMI cut-off frequency is shown by curve 804 as a function of the percentage used to set the starting value R-wave sensing threshold.

The control module 80 may be configured to adjust the low cut-off frequency of the detectable EMI by adjusting the quiet time interval and/or adjusting the noise threshold. As the quiet time interval is increased for a given noise threshold, the cut-off frequency is lowered. As the quiet time interval is decreased for a given noise threshold, the cut-off frequency is increased. If the noise threshold is increased, for a given quiet time interval, the cut-off frequency is increased, and if the noise threshold is decreased for the same quiet time interval, the cut-off frequency is decreased. As the noise threshold approaches 100% of the maximum peak amplitude of the cardiac signal during the post-sense blanking period, the portion of the noise waveform between a negative-going threshold crossing and the next positive going threshold crossing approaches the half cycle length of the noise waveform frequency. In that case, the cut-off frequency approaches an EMI frequency having a half-cycle length equal to the quiet time interval. By reducing the noise threshold, the detectable EMI cut-off frequency has a half cycle length that is greater than the quiet time interval.

Thus, a method and apparatus for detecting EMI in a cardiac electrical signal and withholding a ventricular tachyarrhythmia detection in response to detecting EMI by an ICD system have been presented in the foregoing description with reference to specific embodiments. In other examples, various methods described herein may include steps performed in a different order or different combination than the illustrative examples shown and described herein. It is appreciated that various modifications to the referenced embodiments may be made without departing from the scope of the disclosure and the following claims.

The invention claimed is:

1. An implantable cardioverter defibrillator (ICD) comprising:
a therapy delivery circuit configured to deliver a tachyarrhythmia therapy to a patient's heart via a pacing electrode vector coupleable to the therapy delivery circuit;
a sensing circuit configured to:
receive a first cardiac electrical signal via a sensing electrode vector coupleable to the sensing circuit;
sense a first cardiac event in response to a first crossing of a sensing threshold amplitude by the first cardiac electrical signal;
start a blanking period in response to sensing the first cardiac event; and
sense a second cardiac event in response to a second crossing of the sensing threshold amplitude by the first cardiac electrical signal after an expiration of the blanking period; and
a control circuit coupled to the sensing circuit and the therapy delivery circuit and configured to:
start a first timer set to a first time interval in response to the first cardiac electrical signal crossing a noise threshold amplitude;
during the blanking period, reset the first timer to the first time interval in response to each crossing of the noise threshold amplitude by the first cardiac electrical signal that occurs prior to the first time interval expiring without restarting the blanking period;
determine at least a first parameter of a behavior of the first timer;
in response to the sensing circuit sensing the second cardiac event, compare at least the first parameter to electromagnetic interference (EMI) event criteria;
identify the second cardiac event as an EMI event in response to the EMI event criteria being satisfied;
update an EMI event count in response to identifying the second cardiac event as an EMI event;
compare a value of the updated EMI event count to EMI detection criteria; and
withhold the tachyarrhythmia therapy in response to the value of the updated EMI event count satisfying the EMI detection criteria.

2. The ICD of claim 1, wherein the control circuit is configured to:
set the noise threshold amplitude based on an amplitude of the first cardiac electrical signal at the first crossing of the sensing threshold amplitude.

3. The ICD of claim 1, wherein the control circuit is configured to:
set the noise threshold amplitude equal to the sensing threshold amplitude; and
start the first timer in response to the first crossing of the sensing threshold amplitude by the first cardiac electrical signal.

4. The ICD of claim 1, wherein:
the control circuit is configured to
determine the first parameter based on the first timer behavior that occurs during the blanking period.

5. The ICD of claim 1, wherein the control circuit is configured to detect EMI occurring down to an EMI cut-off frequency by setting the first time interval to be equal to or less than a half cycle length of the EMI cut-off frequency.

6. The ICD of claim 5, wherein the control circuit is configured to detect EMI having a half cycle length that is greater than the first time interval by:
holding the first timer at the first time interval until the first cardiac signal falls below the noise threshold amplitude, and
counting down the first time interval after the first cardiac signal falls below the noise threshold.

7. The ICD of claim 5, wherein the control circuit is configured to adjust the EMI cut-off frequency by adjusting the noise threshold amplitude.

8. The ICD of claim 1, wherein the control circuit is configured to:
set a monitoring interval;
operate the first timer to start in response to the first cardiac electrical signal crossing the noise threshold amplitude during the monitoring interval; and
determine the first parameter based on the behavior of the first timer during the monitoring interval.

9. The ICD of claim 1, wherein the control circuit is configured to:
set a timer status parameter to a first value in response to the first timer being started;
set the timer status parameter to a second value in response to the first timer timing out;
determine the first parameter by determining a value of the timer status parameter; and
identify the second cardiac event as an EMI event in response to at least the timer status parameter being the first value at a time of the second crossing of the sensing threshold amplitude by the first cardiac electrical signal.

10. The ICD of claim 1, wherein the control circuit is configured to:
determine the first parameter by setting a timer time out parameter to a first value in response to the first timer timing out and setting the timer time out parameter to a second value in response to the timer not timing out; and
identify the second cardiac event as an EMI event in response to at least the timer time out parameter being the second value.

11. The ICD of claim 1, wherein the control circuit is configured to:
determine the first parameter by determining an on time interval extending from a start time at which the first timer is started until an end time at which one of the first timer times out or the second cardiac event is sensed; and
identify the next cardiac event as an EMI event in response to the on time interval being greater than or equal to an EMI event on time threshold.

12. The ICD of claim 1, wherein the control circuit is further configured to:
determine event intervals between consecutive cardiac events sensed by the sensing circuit;
compare the event intervals to a tachyarrhythmia detection interval;
increase a count of tachyarrhythmia detection intervals in response to each one of the determined event intervals that is less than the tachyarrhythmia detection interval; and
determine the first parameter in response to a value of the count of tachyarrhythmia detection intervals being greater than a sensed event confirmation threshold.

13. The ICD of claim 1, wherein:
the sensing circuit comprises:
a first sensing channel configured to receive the first cardiac electrical signal and sense the first cardiac event and the second cardiac event; and
a second sensing channel configured to receive a second cardiac electrical signal via a second sensing electrode vector;
the control circuit is further configured to:
determine a morphology parameter from the second cardiac electrical signal in response to the second cardiac event being sensed;
compare the morphology parameter to potential shockable beat criteria; and
identify the second cardiac event as an EMI event in response to the morphology parameter not meeting the potential shockable beat criteria and the first parameter satisfying the EMI event criteria.

14. The ICD of claim 1, wherein:
the sensing circuit comprises
a first sensing channel configured to receive the first cardiac electrical signal and sense the first cardiac event and the second cardiac event; and
a second sensing channel configured to receive a second cardiac electrical signal via a second sensing electrode vector and sense a third cardiac event in response to the second cardiac electrical signal crossing a second sensing threshold amplitude;
the control circuit is further configured to:
start a second timer set to a second time interval;
reset the second timer to the second time interval in response to each crossing of the second sensing threshold amplitude by the second cardiac electrical signal prior to the second timer timing out;
determine at least a second parameter of a behavior of the second timer;
in response to the sensing circuit sensing the second cardiac event, compare the second parameter to the EMI event criteria; and
identify the second cardiac event as an EMI event in response to the EMI event criteria being met by at least one of the first parameter or the second parameter.

15. The ICD of claim 1, wherein the control circuit is further configured to:
determine an EMI index in response to identifying the second cardiac event as an EMI event;
compare the EMI index to alert criteria; and
generate an alert in response to the EMI index satisfying the alert criteria.

16. The ICD of claim 1, wherein the control circuit is further configured to:
determine event intervals between consecutive cardiac events sensed by the sensing circuit;
compare the event intervals to a tachyarrhythmia detection interval;
increase a tachyarrhythmia detection interval count in response to each one of the determined event intervals that is less than the tachyarrhythmia detection interval;
compare the tachyarrhythmia detection interval count to a tachyarrhythmia detection threshold; and
compare the EMI event count to the EMI detection criteria in response the tachyarrhythmia detection interval count being equal to or greater than the tachyarrhythmia detection threshold.

17. The ICD of claim 1, wherein the control circuit is further configured to control the therapy delivery circuit to deliver the tachyarrhythmia therapy in response to the EMI detection criteria not being satisfied.

18. The ICD of claim 1, further comprising a housing enclosing the therapy delivery circuit, the sensing circuit and the control circuit and having a connector block for receiving an extra-cardiovascular lead carrying at least one electrode of the sensing electrode vector.

19. The ICD of claim 1, wherein the control circuit is further configured to:
after the expiration of the blanking period, reset the first timer to the first time interval in response to each crossing of the noise threshold amplitude by the first cardiac electrical signal that occurs prior to the first time interval expiring.

20. The ICD of claim 1, wherein the control circuit is further configured to:
after an expiration of the first time interval during the blanking period, withhold resetting the first timer in response to a crossing of the noise threshold amplitude by the first cardiac electrical signal during the blanking period.

21. A non-transitory, computer-readable storage medium comprising a set of instructions which, when executed by a control circuit of an implantable cardioverter defibrillator (ICD), cause the ICD to:
sense a first cardiac event by a sensing circuit in response to a first crossing of a sensing threshold amplitude by a cardiac electrical signal;
start a blanking period in response to sensing the first cardiac event;
sense a second cardiac event in response to a second crossing of the sensing threshold amplitude by the cardiac electrical signal after an expiration of the blanking period;
start a timer set to a time interval in response to the cardiac electrical signal crossing a noise threshold amplitude;
during the blanking period, reset the timer to the time interval in response to each crossing of the noise threshold amplitude by the cardiac electrical signal that occurs prior to the time interval expiring without restarting the blanking period;
determine a parameter of a behavior of the timer;
in response to sensing the second cardiac event, compare the parameter to electromagnetic interference (EMI) event criteria;
identify the second cardiac event as an EMI event in response to the EMI event criteria being satisfied;
update an EMI event count in response to identifying the second cardiac event as an EMI event;
compare a value of the updated EMI event count to EMI detection criteria; and withhold a tachyarrhythmia therapy in response to the value of the updated EMI event count satisfying the EMI detection criteria.

* * * * *